(12) United States Patent
Rathore et al.

(10) Patent No.: US 11,206,798 B2
(45) Date of Patent: Dec. 28, 2021

(54) METHODS AND COMPOSITIONS FOR MODULATING GOSSYPOL CONTENT IN COTTON PLANTS

(71) Applicant: THE TEXAS A&M UNIVERSITY SYSTEM, College Station, TX (US)

(72) Inventors: Keerti S. Rathore, College Station, TX (US); Madhusudhana R. Janga, College Station, TX (US); Devendra Pandeya, College Station, TX (US); LeAnne M. Campbell, College Station, TX (US)

(73) Assignee: THE TEXAS A & M UNIVERSITY SYSTEM, College Station, TX (US)

( * ) Notice: Subject to any disclaimer, the term of this patent is extended or adjusted under 35 U.S.C. 154(b) by 0 days.

(21) Appl. No.: 16/158,936

(22) Filed: Oct. 12, 2018

(65) Prior Publication Data

US 2019/0110428 A1 Apr. 18, 2019

Related U.S. Application Data

(60) Provisional application No. 62/571,611, filed on Oct. 12, 2017.

(51) Int. Cl.
*C12N 15/82* (2006.01)
*A01H 6/60* (2018.01)
*C07K 14/415* (2006.01)

(52) U.S. Cl.
CPC ........... *A01H 6/604* (2018.05); *C07K 14/415* (2013.01); *C12N 15/825* (2013.01); *C12N 15/8218* (2013.01); *C12N 15/8225* (2013.01); *C12N 15/8234* (2013.01); *C12N 15/8242* (2013.01); *C12N 15/8243* (2013.01); *C12N 15/8261* (2013.01); *C12N 2310/14* (2013.01)

(58) Field of Classification Search
CPC .................................................... A01H 6/604
USPC ......................................................... 800/314
See application file for complete search history.

(56) References Cited

U.S. PATENT DOCUMENTS

2007/0199098 A1 8/2007 Rathore et al.

FOREIGN PATENT DOCUMENTS

CN 104450733 A 3/2015

OTHER PUBLICATIONS

Scheffler and Romano J. Plant Regist. 6:190-194 (Year: 2012).*
Abudayyeh, et al., "C2c2 Is a Single-Component Programmable RNA-Guided RNA-Targeting CRISPR Effector," Science 353:aaf5573 (2016).
Anders, et al., "HTSeq—a Python Framework to Work with High-Throughput Sequencing Data," Bioinformatics 31 (2):166-169 (2015).
Bolger, et al., "Trimomatic: A Flexible Trimmer for Illumina Sequence Data," Bioinformatics, 30:2114-2120 (2014).
Houmard, et al., "High-Lysine Corn Generated by Endosperm-Specific Suppression of Lysine Catabolism Using RNAi," Plant Biotechnol J 15, 605-614 (2007).
International Search Report and Written Opinion for International Application No. PCT/US2018/055693 dated Jan. 23, 2019.
Kim, et al., "HISAT: A Fast Spliced Aligner with Low Memory Requirements," Nat Meth 12(4):357-360 (2015).
Larson, et al., "CRISPR Interference (CRISPRi) for Sequence-Specific Control of Gene Expression," Nat Protoc 8 (11):2180-2196 (2013).
Lee, "The Genomic Allocation of the Principal Foliar-Gland Loci in Gossypium hirsutum and Gossypium barbadense," Evolution 19:182-188 (1965).
Liu, et al., "High-Stearic and High-Oleic Cottonseed Oils Produced by Hairpin RNA-Mediated Post-Transcriptional Gene Silencing," Plant Physiology 129:1732-1743 (2002).
Love, et al., Moderated Estimation of Fold Change and Dispersion for RNA-Seq Data with DESeq2, Genome Biol 15:550(2014).
Ma, et al., "Genetic Basis for Glandular Trichome Formation in Cotton," Nat Commun 7:10456 (2016).
Palle, et al., "RNAi-Mediated Ultra-Low Gossypol Cottonseed Trait: Performance of Transgenic Lines Under Field Conditions," Plant Biotechnol J 11:296-304 (2013).
Percy, et al., "Qualitative Genetics and Utilization of Mutants in Cotton," (Fang and Percy, eds.), American Society of Agronomy, Inc. Crop Science Society of America, Inc., and Soil Science Society of America, Inc., Madison, Wisconsin pp. 155-186 (2015).
Rathore, et al., "Ultra-Low Gossypol Cottonseed: Generational Stabililty of the Seed-Specific, RNAi-Mediated Phenotype and Resumption of Terpenoid Profie Following Seed Germination," Plant Biotechnol J 10:174-183 (2012).
Schmidt, et al., Silencing of Soybean Seed Storage Proteins Results in a Rebalanced Protein Composition Preserving Seed Protein Content Without Major Collateral Changes in the Metabolome and Transcriptome, Plant Physiology 156:330-345 (2011).
Sun, et al., "Transcriptome-Wide Identification and Stress properties of the 14-3-3 Gene Family in Cotton (*Gossypium hirsutum* L.)," Functional and Integrative Genomics 11(4):627-636 (2011).
Sunilikumar, et al., "Engineering Cottonseed for Use in Human Nutrition by Tissue-Specific Reduction of Toxic Gossypol," Procedures of the National Academy of Sciences of the United States of America 103:18054-18059 (2006).
Xie, et al., "Construction of cDNA Library of Cotton Mutant (Xiangmian-18) Library During Gland Forming Stage," Colloids and Surfaces B: Biointerfaces 60(2):258-263 (2007).

(Continued)

*Primary Examiner* — Li Zheng
(74) *Attorney, Agent, or Firm* — Dentons US LLP

(57) ABSTRACT

The present disclosure provides cotton plants with reduced gossypol levels in the seed, and in further embodiments provides cotton plants with increased gossypol levels in the leaves. Also provided are methods for reducing gossypol content in seeds of a cotton plant by down-regulation of CGF2 expression, and in certain embodiments CGF1 and/or CGF3 expression, in the plant, and methods for increasing gossypol content in leaves of a cotton plant by tissue-specific overexpression of CGF2, and in certain embodiments CGF1 and/or CGF3, in the plant.

18 Claims, 6 Drawing Sheets

Specification includes a Sequence Listing.

(56) References Cited

OTHER PUBLICATIONS

Yu, et al., "CottonGen: A Genomics, Genetics and Breeding Database for Cotton Research," Nucleic Acids Research 42:D1229-D1236 (2014).

Zhao, et al., "Sequence-Specific Inhibition of microRNA via CRISPR/CRISPRi System," Science Rep 4:3943 (2014).

Zhang, et al., "Sequencing of Allotetraploid Cotton (*Gossypium hirsutum* L. acc. TM-1) Provides a Resource for Fiber Improvement," Nat Biotech 33(5):531-537 (2015).

\* cited by examiner

SEQUENCE LISTING

<160> NUMBER OF SEQ ID NOS: 122

<210> SEQ ID NO 1
<211> LENGTH: 3467
<212> TYPE: DNA
<213> ORGANISM: Gossyppium hirusutum L.

<400> SEQUENCE: 1

```
tctctccaaa atcaaccata ctcacaaatg cctacttta ttaaaaaatg acattttctt      60
caaaaattag tcttcattct ctctaattta ataggagatt tgatggagga atcacattat     120
tttcgaatga caagaaggca tgattatgag atatatgtac ggggcaacaa tttaataatg     180
acaaagttta ttatattatt acgatgaatc ttttcatttc acatcaaagt aaatgttcaa     240
tgaatttgct tctacccttt gcttcacgta cttcaaaaat aatgaaaacc tcaatataaa     300
ttgttgataa gttggtgaaa aatagtgtag tttcatgatg ttgtgtaaat taattatctc     360
gttaaaaatt ttatttatat gtattattaa gtggtgattt gaattttta atttttttta     420 ttatataaat aacctgaaat taaatgatga gtagaattaa gtaaaaattc tatagtatcc     480
atctactaaa ggttatattg tattttgtca tttctattga aaaaaatgaa taaattcatc     540
cttataagtt agagaccaaa gaacaaaatg gctatttgt taaaaattta tttcatttat     600
acttttaagt gatgatgtga ctatcgaagt aactaaatag caacatgtgg tatgccacat     660
gtacctcatg ctaatgtgac acatattacc atatcaacaa atatttaaaa attaataaaa     720
tctaaaaaat aaataagaca aatagttgta cccaagttca tcctagacgt tgttttaaaa     780
taattataaa aaattatata ttttttttaaa attaatgttg tccacataag cataaggtat     840
acgtggcaca ttatatgttg ttatttgatt gcttcgtcag ttacgtaatc atttaaaagc     900
ataaatggat gaattttta acaggacttc catttattta agtaaaaaga gtaaattaca     960
atccaactcc taattaaggt atctttatgg cacttttacc ttaattaatt ccatgtcact    1020
taaaaattcg aaatcatcac atataaatag aaattttaac aaaataatta atttacatta    1080 ttttttcta atttactatt tttttaataa aaaaacaaaa tgcaatccat attttaaaca    1140
ctgtatcaca actaaaaggg aaagtagata agtttgaaaa gtaggttgag acaagaatgt    1200
gtgatgaatt attaaaaggg taaaagataa aaaataattt tttatttgg ttcaacagtt    1260 gcctcttgag tttagtatag gaaacattta aaatggttta aatgctattc ccttgttaaa    1320
atggtttaaa ttgattttgg tattgattga ggtttaagat aaaaaagaag gaaaagagaa    1380
gaaatttgat gtaaacgcaa acaatgaggg aggaggagcc cacacacgca tcagtagtca    1440
gtcagtcact ggggctttcg ctatcacttc atgtgctagt gctgcgtaat aggtccccc    1500 ccccccccc caaaccctttc catcttctgc tatctggccc ttataaaccc aacgcccct    1560
```

-continued

```
ccaacctctc attccattcc acacctccct gttttctcct ttctgtcacc catggaagac    1620
ctcataatct ctccctcttc atcttcttct ctggtttcct tttcccagga aactccgtct    1680
ccaatccttc agcagaggct gcagtttgta attcaaagcc agcaagattt gtgggcatat    1740
gctatattat ggcagacact gaacgatgac ctgggtcgtc tgttcttggc ttggggagat    1800
ggtcatcttc aatgcactaa agatgcttct ccaaggttga gttccggctt ccacagcgaa    1860
cgaactaagg tgattaaagg aatccaagcc ctcattggag accaacatga catcgatttg    1920
tctatgatcg acggaaccga tatcactgat gtcgaatggt tctatatgat gtcaatggct    1980
cgatccttct ctgctggcga agggattcct ggcaaggctc ttagtactgg gtctttggtt    2040
tggttaactg gtgctcatga gttgcaattt tacaattgtg aaagagctag agaagcccaa    2100
atgcatggcc ttgaaacact ggtttgcata cccacttctt gtggtgttct tgaactagga    2160
tcctcagaga ttatcaggga aaactggggt ttagtccagc aagtgaaatc cctattcgaa    2220
tccgatctca ttggtctggt tccaaaacaa tcgactcctc caaatttaac cccagcttcg    2280
gtccagttcc ttaacagaaa tatctcattt gcagacatcg cataatagc gggtgttcag    2340 gaagaagacg gtgcaagcca ggatattaaa acaaagcaag agcataacaa taaccaaacc    2400
aagaaagatt cctcaaaact tgggcaacct tcttatgtgg actcagagca ttcggattct    2460
gattttccat tactagccat gaataacgtg gagaagcgaa ccccaaagaa acgaggaagg    2520
aaacccgggc tcggacgaga gacaccgttg aatcatgtgg aagcggagag gcaacgccgt    2580
gagaagctga accacagatt ctacgctctc cgagcagtag tcccgaacgt gtcgcgcatg    2640
gacaaagcat cgctcttatc tgacgctgtt tcctacatca atgatctaaa ggcgaaaatt    2700
gatgaattag agtcgcagct tcagagagag tgtaagaaag tgaaggtaga aatggttgat    2760
acaatggata ccaaagcac cactactact accacatctg aggaagagca acaggcagcc    2820
aggcccagct attcatctcc tggaactggg agtggcattg aactggaggt caagattatg    2880
gtaaatgatg caatgataag ggttcactca gagaatgtga actatccagc agctaggcta    2940
atgggtgccc ttcgtgactt ggaattccag gtccgtcatg caagcatgtc gtctgttaac    3000
gacctcatgc ttcaagacat agtggtcagg cttcctgatg ggttgagaac tgaagaaggc    3060
ctcaaatctg ctctcctcag gaggctagat ctgcagtaag gttttattat ggttatccag    3120
agtttgtatt ttaaaatgct ctatttcctc ctacttcttt cagttatttt tgttttaact    3180
tttgcttcat cttcaggttt gctttagccg tttctttgct tttctgcttg ttactatgta    3240
actctttggg agagggttct gcactgcttt cttttatcaa atgttctata tttattctag    3300
tgtctgttcc ccgagttaag gacaataata ttccttaatg gattatacac atacaaaaaa    3360
gaacggaaac aatattcgtg catgtttatc aactagaaac caaatccatg ccaaaaacat    3420
gtataataat gtctgcccct atttaaggac tcaaatatac atatttt                 3467
```

<210> SEQ ID NO 2
<211> LENGTH: 3769
<212> TYPE: DNA
<213> ORGANISM: Gossyppium hirusutum L.

<400> SEQUENCE: 2

```
actccgaaac cgacccaaat ccctatttt ctttaaaatt gacattttct tgaaaattag     60
tcttcattct gtctaattta ataggaggca tgacaatgaa ttatatgtac tgggcatgaa    120
tttaataatg acaagtttat tatattatta cttcacatca aagtaaatgt acaatgaatt    180
tgaggaaata tataacacat ctcatcatta caaataaatt tatattttc attttcatt     240
```

```
tttcattttc ctcatgtact tctcaaataa taaaaacctt aatataaatg tttgataagt    300
aatttatatt aaaaagtaat ttgtatttta tatctctact aaaaaaaaag tgtaaattaa    360
ccatttcgtt acaaattctg tccagtaagt ggtgatttgg attttttcaaa ggcttttat    420 tatgcaagta acctgaactt aaaggatgag tagaattaaa taaaaatttc atagtatcct    480
tatactaagg gttagattgc atttttattct ctctattaaa aaaaatgaac aaattaattc    540
ctgtaagtta gagaccaagg aacaaaatga ccatttttgtt aaaaattcca tccatttata    600
cttttaagtg acgatgtgac taacgaagca actaaatagc gacatgtgtt atgccacatg    660
tacctcatgc taatgtgaca cattttacca tattaataaa atctagaaaa taaataagac    720
aaacagttgt ccaagttcat cctaaacgtt gttttaaaat aattacaaaa aattatttaa    780
actttataaa aaaaattata tattttttta aattaatagt tgtccacata agcataaggt    840
acacgaggca cagcacactc ctatttgatt gtttcgtgag tcacttaatc atttaaaagc    900
aaaaatggat ggattttttta aacagaatga ctaatttact ttttgaccaa atgcatagag    960
attaatttgt cacttaacaa catatatgaa tggggatttt aacaaaatga tcaatttaca   1020
ttattttttc taatttaccc atattttttaa caaaaaaaat acaaaacaca atccatattt   1080
taaacattgt atcacaatta aaagggaaag tagataagtt tgagaagaat gtgtgatgaa   1140
ctattaaaag ggtaaaagac aaaaaataat ttttttatttg gttcaacagt aaaaaccact   1200
ggcctcttga gtttagtata ggaaacattt aaaatggttt aaatgctaaa tgctattcca   1260
tggtttaaat tgattttggt attgattgag gtttaagata aaaagaagg aaaagaaaag   1320 aaatttgatg taaacgcaaa caatgaggga ggaggagccc acacaggcat cagtagtcgg   1380
tcagtcactg gggctttcgc catcacttca tgtgctagtg ctgcgtaata gtccccccccc   1440 cccccccaac cttcatcttc tgcgatctgg cccttataaa cccaacccccc ctccaacctc   1500 tcattccatt cccaacctct ctgtttttctc ctttctgtca cccatggaag tcctcataat   1560
gtctccctct tcatgttctt ctctggtttc cttttcccag gaaactccgt cttcaacct    1620 tcagcagagg ctgcagtttg taatccaaag ccagcaagat ttgtgggcat atgctatatt   1680
ttggcagaca ctaaacgatg acctgggtaa tctgttcttg gcttggggag atggtcatct   1740
tcaatgcact aaagatgctt ctccaaggtt gagttccagc ttccacagcg aacgaactaa   1800
ggtgatgaaa ggaatccaag ccctcattgg agaccaccat gacgtcgata tgtctatgat   1860
cgacggaacc gatatcactg atgtcgaatg gctctatatg atgtcaatga ctcgatcctt   1920
ctctgctggc gaagggattc ctggcaaggc tcttagtact gggtctttgg tttggttaac   1980
tggtgctcat gagttgcaat tttacaattg tgaaagagct agagaagccc aaatgcatgg   2040
acttgaaaca ctggtttgca tacccacttc ttgtggcgtt cttgaactag gatcctccga   2100
gattatcagg gaaaactggg gtttagtcca gcaagtgaaa tccctattcg aatccgatct   2160
cattggtctg gttccaaaac aatcgactcc tccaaattta accccagctt cgatccagtt   2220
tcttgacaga aatatctcat ttgcagacat cggcataata gcgggtgttc aggaagaaga   2280
cgatgcaagc caggatatta aaacaaagca agagcacagc aataaccaaa ccaagaaaga   2340
ttcctcaaaa cttgggcaac cttcttatgt ggactcagag cattcagatt ctgatttttcc   2400 attactagcc atgaataacg tggagaagcg aaccccaaag aaacgaggaa ggaaacccgg   2460
cctcggacga gagacaccgt tgaaccatgt ggaagcggag aggcaacgcc gtgagaagct   2520
gaaccacaga ttctacgctc tccgagcagt agtcccgaac gtgtcgcgca tggacaaagc   2580
```

| atcgctctta tctgacgctg tttcctacat caatgatcta aaggcgaaaa ttgatgaatt | 2640 |
| agagtcgcag cttcagagag agcgtaagaa agtgaaggta gaaatggttg atacaatgga | 2700 |
| taaccaaagc accactacta ctaccacatc tgaggaagag caacaggcaa ccaggcccag | 2760 |
| ctattcatct cctggaactg ggagtggcat tgaactggag gtcaagatta tggtaaatga | 2820 |
| tgcaatgatt agggttcact cagagaatgt gaactatcca gcagctaggc taatgggtgc | 2880 |
| ccttcgtgac ttggaattcc aggtccatca tgcaagcatg tcgtctgtta acgacctcat | 2940 |
| gcttcaggac attgtggtca ggcttcctga tgggttgaga actgaagaag gcctcaaatc | 3000 |
| tgctcttctc aggaggctag atctgcagta aggtttaatt atggttatcc agagtttgta | 3060 |
| ttttaaaatg ctctatttcc tcctacttat ttttatccct tccgtttctt tcttctttca | 3120 |
| gtttattttg ttttaacttt tgcttcatct tcaggtttgc tttagccgtt tcttttcttt | 3180 |
| tctgcttctt actatgtaac tcttgggga ggggttctg cgctgctttc ttttatcaaa | 3240 |
| tgttctacat ttattctagc gtctgttccc cgagttcagg aaaatcatat tccttaatgg | 3300 |
| atatacacat acaaaaaaga acgaaaacaa tattcgtgca tgtttatcag ctagaaacaa | 3360 |
| agtccatgcc aaaaacatat ataatcatgt ctgcccgtta ttaaggactc aaatatagat | 3420 |
| attttttgttc ttacatatca aatcagatta ctattgatga acctcaaaat ctaggacttg | 3480 |
| aagccaacgg aggatgctat ggagacggga caatcgttgc ggaattgtgc aaaacagagg | 3540 |
| accgtatacc actatttacc acgtataaag agaagcttat atatatggta attgctcagg | 3600 |
| gatcagtcca cgaagaaaac ctatatcttt tcttgaaatg aaaaagcaaa ataaaaaatt | 3660 |
| tgtgagaaat atttggaaaa agaaaattta aagttttgg acgttcctaa atttggctct | 3720 |
| taaaaattta atgatgacaa atctctacaa attttttata ttacaaaac | 3769 |

<210> SEQ ID NO 3
<211> LENGTH: 4264
<212> TYPE: DNA
<213> ORGANISM: Gossyppium hirusutum L.

<400> SEQUENCE: 3

| caatattacc ttggctagta atgaacttaa ttagggcttc aatcttctct tcaggcataa | 60 |
| aagaatgttt aggaattggt ggattgttca acaaagtgtt gacttcagca atcacttgta | 120 |
| gtaacatcca tagccttcaa tgaggtttct ccctctacct cagtagtaac tataaaaaat | 180 |
| atcatttgcc ttttcaataa cagtcacttt gatgacaatt ttttttaggc aaagattaga | 240 |
| gcatctttgt aacaagctct aagtttgagt attcttcacc aaaggcaaaa acctaatttt | 300 |
| aaatgtcata aagctttgca tagaatttag ataaggtctt attgtcatac attgttaaag | 360 |
| tttcaaatct cgtagtcagc atttgaagtt tggattactt cacaattggt cctttataag | 420 |
| tagtttcaag aatagtctaa gcttctctag caaatgatca tttagatatt gacctaaaat | 480 |
| cttgaggatt aactctagag aaaattacct taaagtctta gagtttgcat tagccaatttt | 540 |
| ctcttcatca ttagtctaag ttagtttagg tttgagattt ctcacaccat atacactagt | 600 |
| tattagtagc tcctaaccag tcaaaattga gtgccaagat ttttcatcca tgaacttgat | 660 |
| aaagcatcat ccttaccttc tactaggcat agtttgtacc atccaacatg ggggaacttg | 720 |
| gggctattag tccttccatc ttaattgcaa atcaaaaata ggatcacaac ttagtacatt | 780 |
| aagtgtctag ctctgatacc aaatatggat tcttttgaaat ttgccttgca attttttcatc | 840 |
| caattgtaac tagatgaagt gactaatagt tatgaaacga gagatggaaa aaaagagttt | 900 |
| ggtttcgcag ttcaaaaact ttctacattt gtagagcttt acccaaagag taatctacta | 960 |

```
taaatcaata tgtataagac gttatttaag ttcaactcac tcactaagtt gcaaccctac    1020
tcctatactt caatctagat cactttccaa ctaagtatag cttagctaca aattgatgta    1080
caaaacaatt tacgtacaca agtatgcatt ggaaataagt tcctcaatga acaagttaag    1140
tgctctctct aatgctctta accttcaaac aagttgcctc ttaaataagt gtaattaacg    1200
tgttaaaata caatcaatgt aaatatctaa ttcttcaaaa ggagccctag aaaatgtctt    1260
caataaagaa tatacttgta gagatcttct cgatattaaa tttattgtag atctaatctc    1320
tcaaataaga gaacttctaa tcacatcgag agtattcaca aagttcatgc tagacttgat    1380
tcttacacga tctgtcttaa tagattgcaa aaaaccttca aggatataca tttaaaagtt    1440
ccaacaattt taattaaaat atggtaatca cataagatat cttacaatat tttgctagat    1500
gtggtgttgc ctcacaccct aagagaccc taacaatata tgcataacat atcttaaagt    1560
atatatttga cattggattt cccaaaattt tctaaggtgt cctatcatga aatgtttggt    1620
gctaggtgtt tgaaacatga aagaaatcaa gactctttcg aagctgattg gggcttcttt    1680
gtgcataata agtcaataat ttgattttga cccgagcaac cggcaagtgg gacgactccc    1740
ccccaaacat tatttaagaa ggttccataa tgttcaaaac tagcagctag cttctctctg    1800
taagtttgat tgacgatttc atgccactgt acacaccaaa attgaatgat taacactaat    1860
ctttgatttc tttcccgagc ttgatccaca cttagccagc ttcgtcaaag atgatgaacg    1920
tcgacgacgt ccaaggtgtt aacgataaca aggccgatca cgaagatatt caacttcctg    1980
ggttccggtt tcatcctact gatgaagagc tcgtagggtt ttatcttaaa cgcaaagttg    2040
aaaagaaacc cctaagattc gagcttatca aacagattga tatttacaaa tttgatccct    2100
gggatctccc gagtatgttc tcagctcctc ctcgttcatt tttattatat atgtttgcag    2160
atagtgagat tccaatatta aatttacggt ttgattgaat aaagcaggcg tagatcataa    2220
aataaaaatt aaaaaaatgg aaggataatc aaaacccaat ttcattaaaa ttttcctatt    2280
ttgtgatgtg aatgaaaata taaacccttta ttttctttaa gttgatgatg tgtgttggtg    2340
atgaatgaaa tagcagaagc tagcatggtg gggggaggag gagagagtga atcgtacttc    2400
ttctgcaaac gaggaaggaa atacaggaac agcgtgagac caaacagggt aacagggtct    2460
ggttttggaa aagcaaccgg cattgacaag cctgtttatg ctcaaacagg tgatcatcaa    2520
ggccttgcct gcattgggtt aaagaaaacc ttagtgtatt accgtggagc cgccggaaaa    2580
gggaccaaaa ccgattggat gatgcacgag tttcgtcttc cttatcccca tgagagtacc    2640
actgtcgtcg ccttttccaa tcccaaattt gctgcacaag aagctgtaag tataaaatac    2700
tgctcaagtt gggttaatca atgttatttt atttaagggt taatttcatc agaagtccct    2760
gattaacttc aaaatgttct gattgagtca tgataatatc aatattgtat caatcagttc    2820
attttattag cctagcagtt aatttaggca ttaaatacca attcagatat aatatagaat    2880
atatttaaag cacatggatg atcaaactgt aaacacatgt gtacctcttg cttcgacaaa    2940
ttagatattt taaggaaaac aaataatgtc aataaaatta aagaggacta tttgtttta    3000 aggcatcata ttcaaattgt atgtatagta ggcacacacg tatttaccgt tcattatatc    3060
caaaatgcct gagtacgaaa tgcctagagt gataggatgt tgatactttg aggatttgat    3120
tgtaacattt tgaagttttt ggattgattt agaatttaag caatagttta acccctttatg    3180 taaataactt ctgatacgat aataataatt gtctggaatt acaggaagta tggaccatat    3240
gtcgaatctt caagcgaaat tcatcactca aaaaacacaa acaagattgg agacaagtca    3300
```

-continued

| | |
|---|---|
| cagcaaaacg agcttcactg acaacagcgc caacctctca acatgtagt gtggagtcca | 3360 |
| aatccaacgt tcaagggaag tacattacct tcggttctcc atttatagta gattatcatc | 3420 |
| atcataacga cgaggagaag ccatcaatgc ttgtgaatca tcataatata agtggaaaga | 3480 |
| accaaagcca atggcatgtt acagatagaa tgagtagtgc tgcaatggct caaataccatt | 3540 |
| catcaatggc ggcatcatct tctagctttt caaacgatga tttcttcact gaggccaatt | 3600 |
| gggatgagct gaaatcagtt gtggagtttg ctcttgaacc ctttcctatg taaatatata | 3660 |
| taatatgctt tatagggttg cacttttttt tttaattttg atgatgaggg aatattatta | 3720 |
| attaataatt agttgctaat tttatattta ataatggaat atttttataga gactgacatg | 3780 |
| gatgtactcc agttttttttt tctttttttc tttttgtaag tatctttctt tattttttatt | 3840 |
| ttttgaaact tcgttttatt ttatttcttt taccttaatt caatattatt atgaatttga | 3900 |
| gaatcttgga tttatatttc atatgctata ttaattaatt ggtatttaat atgattatat | 3960 |
| actagacaaa aatatatgaa tattaagttc acaagtattt ataaaaattc tcaaatttta | 4020 |
| atttttaagat tatttttgtat ttaaatattt ttttagaaat ttatgatttt taatttttttt | 4080 |
| atagaaattt atgattctttt ttattggaat tataacaaaa atttattaat aatttactca | 4140 |
| aaaatgaagtc attatatatg gttttttttc taatggtgta tactaaaatt tattaattat | 4200 |
| gattctatttt tgcattgatg gatgtaatttt catcaaaata ataattatat attttctac | 4260 |
| aaag | 4264 |

<210> SEQ ID NO 4
<211> LENGTH: 3968
<212> TYPE: DNA
<213> ORGANISM: Gossyppium hirusutum L.

<400> SEQUENCE: 4

| | |
|---|---|
| atgaggtttc tccccctacc tcagtagcaa ctatagaaaa tatcatttgc cttctcaata | 60 |
| acagtcactt tgatgacaaa tttttaggc aaagatcgac gtatcttgt aacaagcttt | 120 |
| aagtttgagt attcttcacc aaaggcaaaa acctaatttt agatgtcata aagctttgca | 180 |
| tagaatttag ataaggtctt attgtcatgc attgttaaag tctcaaatct cgtagtcagc | 240 |
| atttgaattt ggattgcttc acaattggtc ctttataagt agtttcaaga atagtctaag | 300 |
| cttctctagc aaatgatcat ttaagatatt gacctaaaat cttgaggatc aactctagag | 360 |
| aaaattacct taaagtcttg gagtttgcat tggccaattt ctcatcatca ttggtctaag | 420 |
| ttactttagg tttgagattt ctcacactat atacactagt tattggtagc tcctaaccag | 480 |
| tcaaaattga gtgctaagat ttttcatcca tgaacttgat aaaagcatca tccttacctt | 540 |
| ctagtaggca tagtttgttc catccaacat gggggggactt gggactaata gtccttccat | 600 |
| ctcaattgca aatcaataat aggatctcta cttagtacac caagtgtcta gctctgatac | 660 |
| taaatgtgga tttttgaat tttgccttgc aattttttcat tcaattgtaa ctagatcaag | 720 |
| tgactaatag ttataaaatg agagatggac aaaaagagtt tggtctcgta gtttgaaaac | 780 |
| tttctacatt tgcagagctt tacccaaaga gtaatctaca ataaatcaat atgtataaga | 840 |
| cgtgatttaa gttcaactca ctcactaagt tgcaacccta ctcctatact tcaatctaga | 900 |
| tcactttccc actaagtata acttagctat aaattgatga attaaacaat ttacttacac | 960 |
| aagtatgcat tggaaataag tttctcaatg aacaagttaa gtgctctctc tcatgctctt | 1020 |
| aaacttaaaa caagttgcct cttaaataag tgtaattagc gtgttaaaat acaatcaatg | 1080 |
| taaatatcta atcttcaaa agtagcccta gaaaatgtct tcaataaga atatacttgc | 1140 |

```
agaaatcttc ttgatattaa atttattgta gatctaatct ctcaaataag agaactttct    1200
gatcacatca agagtattca caaagtccat gcttgacttg attcttgcac tatctatcct    1260
tactaatgga ttgctaaaaa ccttcaagga tatacattta aaagttccaa caattttaat    1320
taaaatatgc taatcacata agatagctta cattaatatt ttgctagatg tggtgttgcc    1380
tcacatcctt aagagaccct aacaatatat gtagagcata tcttaaagta tatatttgac    1440
attggatttc ccaaaatttt ctaaggtgtc ctattatgat atgtttggtg ctaggtgttt    1500
gaaacatgaa agaaatcaag actctttcga agctgattgg ggcttctttg tgcataataa    1560
gtcaataatt tgactttgac ccgagcaacc ggcaagtggg acgactcccc ccctaaacat    1620
tatttaagaa ggttccataa tgttcaaagg tagcagctag cttctctctg taagtttgat    1680
tgacgatttc atgccactgt acacaccaaa attgaatgat taacactaat ctttgatttc    1740
tttcccgagc ttgatccaca cttagccaga ttcgtcaaag atgatgaccg tcgacgacgt    1800
ccaaggtgtt aacgataaca aggccgatca cgaagatatt caacttcctg ggttccggtt    1860
tcatcctact gatgaagagc tcgtagggtt ttatcttaaa cgcaaagttg aaaagaaacc    1920
cctaagattc gagcttatca aacagattga tatttacaaa tttgatccct gggatctccc    1980
aagtatgttc tcagctcctc ttctttcatt tttattatat atgtttgcag atagtgagat    2040
tccaatatta aatttacggt ttgattgaat aaagcaggcc tagatcataa aatagaaatt    2100
ttaaaaatgg aaaggataac caaaacccaa tttcattaaa gttttccaat tttgtggtgt    2160
gaatgaaaat ataagctttt attttcttta agttgatgat gtgtgttggt gatgaatgaa    2220
atagcagaag ctagcatggt gggggagga ggagagagtg aatcgtactt cttctgcaaa    2280
cgaggaagga aatacaggaa cagcgtgaga ccaaacaggg taacagggtc tggttttggg    2340
aaagcaaccg gcattgacaa gcctgtttat gctcaaacag gtgatcatca aggccttgcc    2400
tgcattgggt taaagaaaac cttagtgtat taccgtggag ccgccggaaa agggaccaaa    2460
accgattgga tgatgcacga gtttcgtctt ccttatcccc atgagagcac cactgtcgtc    2520
gccttttcca atcccaaatt tgctgcacaa gaagctgtaa gtataaaata ttgctcaagt    2580
tgggttaatc aatgttattt tgtttaaggg ttaatttcat tagaagtccc tgattaactt    2640
caaaatgttc tgattgagtc atgataaaat caatatcgta tcaatcagtt tattttatta    2700
gcctagcagt taatttaggt gttaaatacc aattcagata taatatcgag tatatttaaa    2760
gcacatggat gatcaaactg taaacacatg tgtacctctt gcttcgtcaa cttagatatg    2820
atattttaag gaaaacaaat aatgtcaata aaatgtaaga ggactatttg tttttaaggc    2880
atcagattca aattgtatgt atagtaggca cacacgtatt taccgttcat tatatccaaa    2940
atgtccgagt acgaaatgcc tagagtgata ggatgttgat actttgagga tttgattgta    3000
acattttgaa gtttttggat cgatttagaa tttaagcaat aatttaaccc ttcatgtaaa    3060
taacttgtga tacgatagta ataattatcg ggaattacag gaagtatgga ccatatgtcg    3120
aatcttcaag cgaaattcat cactcaaaaa acacaaacaa gattggagac aaatcacagc    3180
aaaacgagct tcactgacaa cagcaccaac ctcccaaaca tgtagtgtgg aatccaaatc    3240
caacgttcaa gggaagtaca ttaccttcgg ttctccattt atagtagatt atcatcaata    3300
tcataacgac gaggagaagc catcaacgct tgtgaatcat cataatatca gtggaaagaa    3360
ccaaagccaa tggcatgtta cagatagaat gagtagtgct gcaacggctc aaataccttc    3420
atcaatggcg gcatcatctt ctagcttttc aaatgatgat ttcttcactg aggccaattg    3480
```

-continued

```
ggatgagctg aaatcagttg tggagtttgc tcttgaaccc tttcctatgt aaatatatat    3540
aatatgcttt ataggggttgc actttttttt tttaattttg atgatgaggg aatattatta    3600
attaataatt agttgctaat tttatattta ataatggaat attttataga gactgacatg    3660
gatgtactcc agttttttt tctttttttg taagtatctt tctttatttt tatttttga    3720 aacttcgttt tattttattt cttttacctt aattcaatat tattatgaat ttgagaatct    3780
tggattaata tttcatatgc tatattaatt aattggtatt taatatgatt atatactaga    3840
gacaaatata tgaatataaa gttcacaagt atttataaaa attctcaaat tttaatttta    3900
agattctttt gtatttcaat attttttag aattttatga ttttagtttt tttttataga    3960
aatttatg                                                              3968
```

<210> SEQ ID NO 5
<211> LENGTH: 3914
<212> TYPE: DNA
<213> ORGANISM: Gossyppium hirusutum L.

<400> SEQUENCE: 5

```
acgaaataag aaacaaatat tctcttttat gagagagaaa ctgagcaaat gactttgtaa      60
ttagaagaat aagttgttaa aagaaggtaa agaaattgta ttgaaaacta ttcctcaaga     120
tcttcctatt tattgcataa gtgttttct tctcccttc aatatttgtg atgccttaca      180
gaaaatgatg aatttctttt gatggggtc agacatagag ggaaatagga aaacacacta      240
agcatcatgg acaaatttgt gcaagccata aagatgtgt tgtatgagta tccaaaattt      300
aagatgcttt aatcttgtta tgcttggcaa atagagttgg tggattataa acaatcccaa      360
tcctcttcag agtcaaatat tcaaagctaa atagttcccg aattgtgggt ttcttgaatc      420
tagtgaagga ttgattgttg aaaacttaga ccatgtttta atgatgtata tcaaagctca      480
atttgtattg catattgttg ggttaaggct attgcaagat tcaaccttgg agtttctcta      540
ttaccacctt aatatgcaag atgataatga gctgagttgg tggttaggtg tagcatggag      600
tatatggaca cataggaacc agtttattta gaataaaaaa agatcataat gtagtccaaa      660
ttgttcaatt tgaatattct tacatggagg cttggtaggg agctcacacg acgatgactc      720
gtattcaacc ttccaggtta agttgttcta cttctaagta gagttggtgt aaatcgctag      780
gtaatgggtt caaatttaac atcgatatgg ttatttttat aagaatgttg ccacgagctg      840
atcgactatc attcataatg aaaatggtga ttttgacaaa ggtcgcacag gttttatcca      900
agcaactatg gctccaaaag ttacacatga ttgttatttg aaaggcattg ctttagttga      960
agtcgttgca aattgagaga gtgatcattg agacggattg tttgattgta ccgcaagatt     1020
taacgagtaa aaaaaggtta tctctatgat gggtttgatt attgaaggct gtctcatgtt     1080
gaaagctttt ttttttttca atttatgtcc ttatgttgaa tgagtagaaa cattgataag     1140
atcgctcatg ctcttgcaag ggtagcttta tgtcatgcaa atccttatgt ttagaattct     1200
tctcctagtt gcatgtcttc cattcttatt taagatgttc gtactctttt atctaatgag     1260
gagtcgagtg tataggataa gcccattagc ttaagaaaat aattttccaa tccttatttt     1320
gggtaatttt gtttgtttca ttccgatttg ataataatct attttcttct ttccttaaaa     1380
aaaaaggcta ggaagagtta tttgaataaa ttaacaaagt tgaagagcta atttaataga     1440
ttaacatttg tatcaaatat taaaacaaca aggtagttaa ttgggagttg agttggggtt     1500
aaaggtgaca cgataagctg aataattaac aaaatatgga tgggaatggt cctaatatct     1560
aaaaatagtt aaaaatcatg ggaaatagaa aaaagacaga taaagatgat tcacgaaatc     1620
```

```
gccccataat aactggtgtg aattaagtta agatcatgag tggaggggtt aagacgccaa    1680
cagaagcacc gcaactccac atcaaataga gtaaaccatc catgccataa agaacaaaaa    1740
agaagaagaa aattcagacc ggtcatcatc cttatttgga gagaatctgg aacaggagat    1800
ttccacgtga taatgatgtc aagatttgac tgacaatagg accatgaggt tgatggtcct    1860
ttatttcccc ggaaaattat actttgtttt ctccaaagca cttcacttaa taattatagt    1920
tttcctcttt tttctcatct gctccatggg gtttatagcc acctagtgac gactttgatc    1980
atcactcttt ttcctctttta tttattcttc ttgctgctga gtccgctttg gttagttttt    2040
cttttttctc tttgaaaaac ggtagtacac actatcatat tcaataatgt cttcctcttc    2100
ttcgtcttct cttattacct taggtcaaga tgcctcacct actttgcaac aacgcctcca    2160
tttcatcgtc caaagtaggc ctgaatggtg ggtatactcc attttctggc aagcttcaag    2220
ggatgttgat ggtcgcgttg ttttgtcatg gggcgatggc tattttcgag ggacccgaga    2280
tggtacggga aaatccatca ataggctgag ccccttccaaa ttggggtcca gtttcgagag    2340
gaaaaggtcg ggaaaagatc aggtgcaagc ttattttaat gaagtgatgg acgtggaccg    2400
tatggtagat ggcgatgtga ctgattatga gtggtactat accgtatcca tgacccgatc    2460
attcgctgta ggtgatggga ttcttgggaa ggctttcgga tcaggctccc atatttggtt    2520
gggtggagac catgaactcc aattgtacca gtgtgagcgt gttagagaag ctcgaatgcg    2580
agggattcaa acattagttt gtcttcctac atccttcggg gttgtcgaat tgggatcttc    2640
tgatatcatc atggaagact ggggcaccct tcaactcact aaatcgatat tcagttctgg    2700
gatcaacaac agcctgggtt caaatcaacc tgcccatgat tcccaacccc aaatctcaac    2760
cccaagtatt cctttttgttg atttttggaat ggtttcaggt gatcaaaagg agcggattct    2820
tgaagacaaa caacaagtcg agcccaagaa agaaactaca ggtttaggcc gttcgtcatc    2880
ggaatctgat ggggatttcg cctctgcaga caccgagttc aatgccagcg gccggtcgaa    2940
aaagagaggt agaaaaccag ggaatgggaa agaatcccct ataaaccacg ttgaagcaga    3000
aaggcaacga cgtgagagac tgaaccatcg tttctacgca cttcgttccg tggttccaaa    3060
cgtatccaag atggacaaag cctcattact ttcagatgca gtagcctaca tcaaggaact    3120
aagatcaaaa atcgataaac tagaggctca actcctagta caatctgaaa atccaagtt    3180 gaaccccatc aatgttttcg aaaaccaaac taccaaatcc gcattcgaca ataccatgaa    3240
acaatcctct acttattggc caaagacagt ggaagttgat gtgaagatag taggatccga    3300
agctatgatt cgggttcgaa gtccagatat cgatcatcca gctgcacgat tgatggatgc    3360
acttcgagac ctagagctac cagttcacca tgccagtgta tcaaacgtca atgatcttat    3420
gctacaggat gttgttgtca gagtccctac tggaatattc ataaccgacg agatgcttag    3480
tactgcaatc cttcagagat gcacgttgaa ttaggtagct agctaggtag ccctgcagtg    3540
agatgcactt ttttttcttt ttgccttctt ttgtttttt gtttgatcaa tgtttcttgt    3600
tttattcgtg cattagttct ttaacatttc ctatatatgt tctacgtata gataggtttc    3660
aattacgacc tgctttttatc agatttcatc atttcattgg cttttaaacaa ctttgctata    3720 tgcatgtttc ctcacaaaca caaacattgg ggcttgaaca atgtggaaac tggctacaat    3780
atagaaataa taattactaa acttaggagc taacttgaat tttaattgtc gaagttaagt    3840
tccaaataat aatttaacca cataagataa catcaattac acagcccgaa atccaggccg    3900
ccagtagcct gtgc                                                     3914
```

<210> SEQ ID NO 6
<211> LENGTH: 9015
<212> TYPE: DNA
<213> ORGANISM: Gossyppium hirusutum L.

<400> SEQUENCE: 6

| | | | | | |
|---|---|---|---|---|---|
| acgaaataag | aaacaaatat | tctcttttat | gagagagaaa | ctgagcaaat | gactttgtaa | 60 |
| ttagaagaat | aagttgttaa | aagaaggtaa | agaaattgta | ttgaaaacta | ttcctcaaga | 120 |
| tcttcctatt | tattgcataa | gtgtttttct | tctcccttc | aatatttgtg | atgccttaca | 180 |
| gaaaatgatg | aatttctttt | gatggggtc | agacatagat | ggaaatagga | aaacacacta | 240 |
| agcatcatgg | acaaatttgt | gcaagccata | gaagatgtgt | tgtatgagta | tccaaaattt | 300 |
| aagatgcttt | aatcttgtta | tgcttggcaa | atagagttgg | tggattataa | acaatcccaa | 360 |
| tcctcttcag | agtcaaatat | tcaaagctaa | atagttcccg | aattgtgggt | ttcttgaatc | 420 |
| tagtgaagga | ttgattgttg | aaacttaga | ccatgtttta | atgatgtata | tcaaagctca | 480 |
| atttgtattg | catattgttg | ggttaaggct | attgcaagat | tcaaccttgg | agtttctcta | 540 |
| ttaccaccct | aatatgcaag | atgataatga | gctgagttgg | tggttaggtg | tagcatggag | 600 |
| tatatggaca | cataggaacc | agtttatta | gaataaaaaa | agatcataat | gtagtccaaa | 660 |
| ttgttcaatt | tgaatattct | tacatggagg | cttggtaggg | agctcacacg | acgatgactc | 720 |
| gtattcaacc | ttccaggtta | agttgttcta | cttctaagta | gagttggtgt | aaatcgctag | 780 |
| gtaatgggtt | caaatttaac | atcgatatgg | ttattttat | aagaatgttg | ccacgagctg | 840 |
| atcgactatc | attcataatg | aaaatggtga | ttttgacaaa | ggtcgcacag | gttttatcca | 900 |
| agcaactatg | gctccaaaag | ttacacatga | ttgttatttg | aaaggcattg | ctttagttga | 960 |
| agtcgttgca | aattgagaga | gtgatcattg | agacggattg | tttgattgta | ccgcaagatt | 1020 |
| taacgagtaa | aaaaaggtta | tctctatgat | gggtttgatt | attgaaggct | gtctcatgtt | 1080 |
| gaaagctttt | tttttcaat | ttatgtcctt | ctgttgaatg | agtagaaaca | ttgataagat | 1140 |
| cgctcatgct | cttgcaaggg | tagctttatg | tcatgcaaat | ccttatgttt | agaattcttc | 1200 |
| tcctagttgc | atgtcttcca | ttcttattta | agatgttcct | actctttat | ctaatgagga | 1260 |
| gtcgagtgta | taggataagc | ccattagctt | aagaaaataa | ttttccaatc | cttattttgg | 1320 |
| gtaattttgt | ttgtttcatt | ccgatttgat | aataatctat | tttcttcttt | ccttaaaaaa | 1380 |
| aaaggctagg | aagagttatt | tgaataaatt | aacaaagttg | aagagctaat | ttaatagatt | 1440 |
| aacatttgta | tcaaatatta | aaacaacaag | gtagttaatt | gggagttgag | ttggggttaa | 1500 |
| aggtgacacg | ataagctgaa | taattaacaa | atatggatg | ggaatggtcc | taatatctaa | 1560 |
| aaatagttaa | aaatcatggg | aaatagaaaa | aagacagata | aaagatgatc | acgaaatcgc | 1620 |
| cccataataa | ctggtgtgaa | ttaagttaag | atcatgagtg | gaggggttaa | gacgccaaca | 1680 |
| gaagcaccgc | aactccacat | caaatagagt | aaaccatcca | tgccataaag | aacaaaaaag | 1740 |
| aagaagaaaa | ttcagaccgg | tcatcatcct | tatttggaga | gaatctggaa | caggagattt | 1800 |
| ccacgtgata | atgatgtcaa | gatttgactg | acaataggac | catgaggttg | atggtccttt | 1860 |
| atttccccgg | aaaattatac | tttgtttct | ccaaagcact | tcacttaata | attatagttt | 1920 |
| tcctcttttt | tctcatctgc | tccatggggt | ttatagccac | ctagtgacga | ctttgatcat | 1980 |
| cactcttttt | cctctttatt | tattcttctt | gctgctgagt | ccgctttggt | tagttttct | 2040 |
| tttttctctt | tgaaaacgg | tagtacacac | tatcatattc | aataatgtct | tcctcttctt | 2100 |
| cgtcttctct | tattaccta | ggtcaagatg | cctcacctac | tttgcaacaa | cgcctccatt | 2160 |

| | |
|---|---|
| tcatcgtcca aagtaggcct gaatggtggg tatactccat tttctggcaa gcttcaaggg | 2220 |
| atgttgatgg tcgcgttgtt ttgtcatggg gcgatggcta ttttcgaggg acccgagatg | 2280 |
| gtacgggaaa atccatcaat aggctgagcc cttccaaatt ggggtccagt ttcgagagga | 2340 |
| aaaggtcggg aaaagatcag gtgcaagctt attttaatga agtgatggac gtggaccgta | 2400 |
| tggtagatgg cgatgtgact gattatgagt ggtactatac cgtatctgtt gcggaaagga | 2460 |
| tcgattcgag aactccgata tgactacaag taaattgacc ggaacgaaaa ataaagtgaa | 2520 |
| cacaaggatt tacgtggttc ggctttaatg cctacgtcca cgggcagagg cgaaaagaaa | 2580 |
| tttcactata acaagatgaa gattacaagt gttttacact caagacacaa cccgagaacc | 2640 |
| tcacaactct caacccctat agaaaacccg aaagctaaaa tcctagcttt caagaacaa | 2700 |
| gctttgctct ctcttggttt gggatgatga atatggctaa tgaacctctc tatttataag | 2760 |
| agagttcaag gacataattg tccaaaactt tggcaaagat ttgtggttga aaatggacac | 2820 |
| caacaaccat ccactaatcc actaccacca acaacccact accaacaaca caatccact | 2880 |
| accaattta agccatttct taacaaatct ccaccttggc ttgaaattta ccaagctgaa | 2940 |
| catcatagta aattcctcga actggatcac ctcttccaaa cgcctctctg gcgctaatca | 3000 |
| atcccgaata cctatcaagt ccaagcaatg cttgaactta tatgcaggga tcaccttagt | 3060 |
| taacatatct gcaggattct tctcggtagc aaccttgctg ataacaatgt caccttgcgt | 3120 |
| aacatgttcc cgaacaaaat gatatctgac atcaatgtgt ttggtccgtt catgaaacat | 3180 |
| ctgattttta gtcagatgta tggcactctg gctatcgcaa atacaacag tgaaatcctg | 3240 |
| ttgtaaaccc aaactgctta ctagaccttt catccacaat gcttctttca ctgcttctgc | 3300 |
| taacgccata tattccgcct cagtcgtaga taaggctacg gtagactgta acacagcttt | 3360 |
| ccaactaatg gctcctccag aataagtgaa aacataaccc gtcagagatc ttcttttgtc | 3420 |
| cagatctcca gcataatcag agtccacata gcccgtgaca ctgctagtgc agtcactctg | 3480 |
| atcatatacc aagcataaat ctgcagaacc tctcaagtac ctgagaatcc atttcacggc | 3540 |
| ctgccagtgt tccttgccag acaactcat gtatctgctg accacactaa ctgcatgtga | 3600 |
| aatgtctgga cgagtgcaaa ccattgcata catcacgctt ccaactgcac tcgagtatgg | 3660 |
| aatgtgagac atttgctgct tttcttcatc agattgtggt gacaactctg cagagagttt | 3720 |
| gaaatgtggt gccaacggag tactcacagt tttcgcttta tccatgccga agcgttgaag | 3780 |
| aaccttttca atgtagttct tctgcgacac acgaagcttg cccgccttgc gatctctgtg | 3840 |
| aatatccatg cccaaaattt tcttggcagc acccagatcc ttcatctcga actcaccact | 3900 |
| caactgcgac tttaacttgt tgatttccga catgttttg gaagcaatta acatgtcatc | 3960 |
| aacatacagc aacaaataaa tgtgcgaacc atctgagagc ttccgatgat agacacaagc | 4020 |
| atcatagtca catcttgtgt aaccatgctg aatcatgaag ctatcaaacc gcttgtacca | 4080 |
| ctgccttggg gattgtttca atccatataa agacttcttt aatagacaga catggtcttc | 4140 |
| tttaccagga actgtaaaac cctctggttg acgcatgtag attgtttcct cgagctcacc | 4200 |
| atgcaagaac gccgtttta cgtcaagctg ctcaagttct agatcagact tggccaccat | 4260 |
| ggcaagtaat acacgaatgg aagaatgctt tacgactggg gagaaaactt cattgtagtc | 4320 |
| aatcccctct ttctgagtga agcctttagc aaccaatcgt gccttgaatc tagttgcttc | 4380 |
| aaccccctagg atgccttcct tttcttgaa gacccatttg caaccaacta tcttctggtt | 4440 |
| acttggcggc ttaaccaact cccaagtatg gttcttgtga agagattcta tctcctcact | 4500 |

```
catagcaatt gcccactgtg ccgattcatc acacgtgaca gcctcattat aactggaagg    4560
ttctatacca atggactccg ccacactgag cgcgaaagac accagattag cgtaacgcgg    4620
atttggtttg atttgtctct tcgttcttcc agtggcaatg ctatatggtt tttcttgagg    4680
tgactcatct tcatcggaat cttgcacctc aacttgatca tcctggactg aagtaccttc    4740
cgtaggaatt ggagcgtcca cctgacactc cacctgcttc tcaacaccgt gatctcccat    4800
tctatctgac tcctccttt cccgggaatt tgtggtggat cgaagcatgg atgactcatc    4860
aaaagtcaca tctctgctga tgatgaactt ggacgaaacc ggatcaggac accacaacct    4920
gtatcctttc accccttggc cgtatccaag aaatatgcat tcttcgccc tcggtttgag    4980 ttttccctca tttacatgag catacgcagg gcagccaaac actcttaaac cagagtaatc    5040
agcaggagaa ccagaccata cttcctcagg agtcttcagc tcaatagctg ttgatggaga    5100
tctgttaacc aaataacaag cagtattaac agcttcagcc caaaattctt caccgagccc    5160
agcatttgat cgcatgcaac gagctcgctc caagagagtt ctattcatgc gttctgcaac    5220
tccattttgt tgtggtgttc gacgaacagt gcggtgtctc actattcctt cattttgca    5280 gaactcattg aattcacctg agcaaaactc caagccatta tccgtccgga atcgcttgat    5340
cttctttcct gtttgatttt cgatcaaagc tttaaattgc ttgaagttga tgagaacctc    5400
atacttgctc ttcagaaaat acacccaaac cttctcgag taatcatcga taaaggtaag    5460
cagatatctg taaccaccct tagaaattgt cggagaaggc ccccaaaggt cagaatggaa    5520
gtaatccact gtgccttttg tcttgtgaat cccagtgctg aactttaccc gagtctgctt    5580
accgaagacg cagtgctcac agaaattcaa ctttcctgta cactgcccag acaataatcc    5640
tcgtttgctt agcaccgata agcctctctc gctcatatgc ccgagccgca tatgccataa    5700
cttcgtggtg tcagaatcta gatcatctga tgatgacact cccgcaacac ctgtaaccga    5760
ggaaccatcg aggaagtaaa ggccccgctc caaattacca cgtatcacag tcaaagcacc    5820
cgagaatacc ttgagaactc caccttcagc agagtaccga aagcctttct tgtccaacgt    5880
actcaaagag atcaaatttt tcttcatttc tggaatgtgc cgaacatcag ttagagttct    5940
aacaataccg tcaaacatct ttatacgaac tgtgccaatc cccatgactt gacatgcgtg    6000
gtcatttccc attagtactg aaccagaatg cttctcgtat gttgagaatg catcttcga    6060 agtacttata tgaaatgtag ctcccgtatc aagaatccat ctcccaccag cgtaagagtc    6120
ggatactgca agaacgatct cggcatcact tgaagaatct gcatcagcta cattcgcacg    6180
atcattttgt tgctcctgtg attctgattt ctccttcctt tcggacaat ctaccttcat    6240 gtgcccgtac ttcttacagt agtagcactg tattctcttc ttggactgcg atctaggatg    6300
gcttttactt gaacttccac cctttgcctt ggatcttcct cgagcaacca agccttcgcc    6360
ttcattgttt tcgaccacct taccagtgat tttcttcctc aactcactgg aacttaaggc    6420
atttttcacc tcctctagag tcaggtcatc acgaccgtac atcattgtat caacaaaatt    6480
ctcatacgag ggaggcaaag aacacaaaac aattattgct tggtcctcat catcgatttt    6540
gttatcgata ttattcaaat ccatgataat ggaattgaat ttatccaggt gctgggaaac    6600
aggtgtacct tcctccatct tcagggcata gagtctttgc ttgaggtaga gccggttcgt    6660
caatgacttc gtcatgtact tgctctctaa ccggagccac aaaccggacg cggttttctc    6720
atccgctact tctcgtagca cttcatctcc tagacatagc agaatagcac tatgtgctct    6780
ttctagcatg tcatcctttt gctcttccga aagcgtgctg ggtaatttat ctttaccaga    6840
caatgctttt agcaatcctt gttgaaccag cactgcccgc atcttgatgc gccataaact    6900
```

```
gaaactatttt tcccggtaa atttctcgac atcatactta gtcgatgaaa cacttgtagc    6960
cataatttgg aacctttgaa tgaatgataa tattttcttc ctgatgtgaa agatcagaca    7020
aagctgcagt cacagggcaa ttcagaaaat attatcactc cttcaactac gctctgatac    7080
caatttgttg cggaaaggat cgattcgaga actccgatat gactacaagt aaattgaccg    7140
gaacgaaaaa taaagtgaac acaaggattt acgtggttcg ctttaatgc ctacgtccac     7200 gggcagaggc gaaaagaaat ttcactataa caagatgaag attacaagtg ttttacactc    7260
aagacacaac ccgagaacct cacaactctc aaccccta ta gaaaacccga aagctaaaat    7320
cctagctttc aaagaacaag ctttgctctc tcttggtttg ggatgatgaa tatggctaat    7380
gaacctctct atttataaga gagttcaagg acataattgt ccaaaacttt ggcaaagatt    7440
tgtggttgaa aatggacacc aacaaccatc cactaatcca ctaccaccaa caacccacta    7500
ccaacaacaa caatccacta ccaattttaa gccatttctt aacagtatcc atgacccgat    7560
cattcgctgt aggtgatggg attcttggga aggcttccgg atcaggctcc catatttggt    7620
tgggtggaga ccatgaactc caattgtacc agtgtgagcg tgttagagaa gctcgaatgc    7680
gagggattca acattagtt tgtcttccta catccttcgg ggttgtcgaa ttgggatctt     7740
ctgatatcat catggaagac tggggcaccc ttcaactcac taaatcgata ttcagttctg    7800
ggatcaacaa cagcctgggt tcaaatcaac ctgcccatga ttcccaaccc caaatctcaa    7860
ccccaagtat tccttttgtt gattttggaa tggtttcagg tgatcaaaag gagcggattc    7920
ttgaagacaa caacaagtc gagcccaaga aagaaactac aggtttaggc cgttcgtcat     7980
cggaatctga tggggatttc gcctctgcag acaccgagtt caatgccagc ggccggtcga    8040
aaaagagagg tagaaaacca gggaatggga aagaatcccc tataaaccac gttgaagcag    8100
aaaggcaacg acgtgagaga ctgaaccatc gtttctacgc acttcgttcc gtggttccaa    8160
acgtatccaa gatggacaaa gcctcattac tttcagatgc agtagcctac atcaaggaac    8220
taagatcaaa aatcgataaa ctagaggctc aactcctagt acaatctgaa aaatccaagt    8280
tgaaccccat caatgttttc gaaaaccaaa ctaccaaatc cgcattcgac aataccatga    8340
aacaatcctc tacttattgg ccaaagacag tggaagttga tgtgaagata gtaggatccg    8400
aagccatgat tcgggttcga agtccagata tcgatcatcc agctgcacga ttgatggatg    8460
cacttcgaga cctagagcta ccagttcacc atgccagtgt ttcaaacgtc aatgatctta    8520
tgctacagga tgttgttgtc agagtcccta ctggaatatt cataaccgac gagatgctta    8580
gtactgcaat ccttcagaga tgcacgttga attaggtagc tagctaggta gccctgcagt    8640
gagatgcact tttttttcttt tttgccttct tttgttttttt tgtttgatca atgtttcttg    8700
ttttattcgt gcattagttc tttaacattt cctatatatg ttctacgtat agataggttt    8760
caattacgac ctgcttttat cagatttcat catttcattg gctttaaaca actttgctat    8820
atgcatgttt cctcacaaac acaaacattg gggcttgaac aatgtggaaa ctggctacaa    8880
tatagaaata ataattacta aacttaggag ctaacttgaa tttttaattgt cgaagttaag    8940 ttccaaataa taatttaacc acataagata acatcaatta cacagcccga aatccaggcc    9000
gccagtagcc tgtgc                                                     9015
```

<210> SEQ ID NO 7
<211> LENGTH: 6200
<212> TYPE: DNA
<213> ORGANISM: Gossyppium hirusutum L.

```
<400> SEQUENCE: 7
cttccctata acaccccaat ccacgtaggt caactgaagt gttacacata tagaaaacag      60
acatgcataa tttgattttt agttcaactt aaatacatat taacttaact aggtgacctc     120
agaaaacttc tacaaaacac aagtttattt aaaaatatac accatagaat aaaagtaaat     180
ggatttaaat atttttcgatg aaatactctc ctttgaataa aatactaatg gtaacgatta     240
cttataaaac attctggtgt atacaagtag aaataatttt gtaaatgaga acttaacaaa     300
ctttaacaaa tccctcaagg ggtcacattc ttataaagat gtaattgaat gagaaagcta     360
tttattatag attaatattt agaaaatttt aacatgccgc ccccaaaaca tatgcatgtt     420
acaaaaaaaa caaatgaagc ctactgtaga gaatgcttct tttggcttag tcccttcaag     480
aagcccataa caaagatcac ctggaaggaa ggaaagaaaa tgggtaagtt taaaataact     540
tagtaagttc cacaaaggaa aactcaacac ttaaataaga acagattcac actacaagtt     600
cataacacag actaatacat tagactctat acgctgagac atatgggcgt atactcttat     660
ctcattggcg aacacttaac cttggcgtat aacctttcga gcatacccac atatatagag     720
cataccatct ttcatgaaat tgggcataca cttatatcct ttcccctaca tagcactaaa     780
acttaaacag aattgatgct tctgcgttaa cataatcttt tttcataagt acttttgtat     840
cacaacctct ctttaggtga actcatactt actttcaaaa cttattaggg cgagttcaat     900
atatccctca tcatttctta atgaatacat tatgatctcg atacgtcaat aggaatcaaa     960
catacttcct taattattaa tcattctttt catctcaact gatatatgca tcacacaaac    1020
atacacaata tcgtattagc ttattccttt caatacaaaa tatatcttat aacaaataca    1080
gagacaaatt gtcttactac ttcataacct tccttaggtt gacctcgaat tttacatatc    1140
agaacagatc ttttgtatca tatcatttcg aacacctatg tattcttgtg agttcagggc    1200
tatttgctat ggttaacaac taacatgtcc tatagtaggc agcacccata acgttaggct    1260
agttagcaac tagtatgccc taccaaaact taacacccac accaacttgt tagtaactaa    1320
catacccccac caatggtcgc caaactattt aacaactaac atgtcctact agtggcctat    1380
catatatccc tatctggtta gcaattaaca tgccctacca gtggtcacac atttctgcca    1440
ttctagtttg caattaacat gccctaccag tggctcatct tatccggata ttgagttcat    1500
atccgtaagg aagtcatttc tatatcatgc cacgattatg catatataac acaggcaatt    1560
acataaaata gaacacaaca tagaaaagaa tcacatggtc tggatcctca tagatgattt    1620
taagaaaatt gttatttat cactactacc gcatgcacac ctctttcttt cttttttgata    1680
acttgttact ttttttccca cgaactcctc ttaacaagat ttcaaagtat aacatagcaa    1740
aagaaagaga aggaaaaacc ccactacaaa ggttttcact gatatttata tctcacagct    1800
tcctcactta gggataatat gtggctaaca tgcaaggcta actcaattct atcctaacca    1860
acataattat tataggtcat tatacataaa aaaataatca taaaactttg gtatttctaa    1920
ttggatccca attaaagcac aactagaact gaatagaaat tacatgtgca caaacaaaca    1980
atatttacat ccacaatccc acaatccttt actggcttac ataaagagaa ggtcttaaca    2040
cacaaacttt tcaaaagaaa cactgattgg cggttcttta aagtaaccac gccaaaacaa    2100
cttagacttc acccaaaata caaatcttaa caggcttacc tataaattat acagtctgcc    2160
acacacagcg tacaactata caattaccac tctgacgaat aaaacataaa tcagtcttac    2220
cttgacttaa atcttagcta actttttagca catacaaacc atcaacaaga ctacgttgga    2280
cagggtatta cattccctct ttattggacg aaataagaaa caaatattct cttttctgag    2340
```

```
agagaaattg ggcaaatgac tttgtaatta aaggaataag ttgttgaaag aaggtaaaga    2400
aattgtattg aaaactattg ctcaggatct tcctatttat tgcataagtg tctttctttt    2460 cctttcaac atttgtgatg ccttacagaa aatgatgaat ttcctttgat ggggtcagac    2520
atagatggta ataagaaaac acactaagca tcatgggaaa atttgtgcaa gccttagaag    2580
atgtgttgta tgagtttcca aaatttaaga tgctttaatc ttgttatgct tggcaaatag    2640
cgttgatgga ttataaacaa tcccaatcct cttccgagtc aaatattcaa agctaaatag    2700
ttcccgaatt gtaggtttct tgaatctagt gaaggattga ttgttgaaga cttagaccat    2760
gttttaatga tgtatagcaa agcttaattt gtattgcatg ttgttgggtt aaggccaatg    2820
caagattcaa ccctgtagtt tctttgctac taccttaata tgcaagacgc taatgagctg    2880
agttggtatt taagtgtagc atgaagcata tggacacata ggaaccgatt tatttggaat    2940 aaaaaagat gacaatgtag tttaaattgt tcaatttgaa tattcttaca cgaggcttgg    3000
tagggagctc acacgacgat gactcgtgtt caacctacca ggttaagttg ttctacttct    3060
aagtagtgtt ggtgcaaatt gctaggtaat aggttcaaat gtaacaccga tatggttatt    3120
tttataagaa tgttgtcacg agctaatcgg ctatcattca taatgagaat ggtgattttg    3180
acaaaggtcg cacaggtttt atccaagcaa ctatgactct agaagttata aatgattgtt    3240
gtttgagagg cattgcttta gttgaagtcg ttgcaaattg agagagtgat cattgagacg    3300
aattgtttga ttgtagcgca agacttaacg agtaaaagca aggttatctc tatggtgggt    3360
ttgattattg aagactgtct catgttgaat gagttggatt agtagaaaca ttgataagac    3420
cgctcatgct cctgctgttg caagggtagc tttatgtcat gcaaatcctt atgtttagaa    3480
ttcttctctt agttgcatgt cttccattct tatttaagat gttcctactt ttttatctaa    3540
tgagtgtata gtataagcca ttagcttaag aaattaattt tccaatcctt attttggtgg    3600
ctttgtttgt ttccttccga tttggtaata atctattttc ttctttccct cgaaaaaaca    3660
aaggctaggg agagttattt gaataaatta acaaagttga agagctaatt taatagatta    3720
acatttgtac caaatattaa aacaaggtag ttaattggga gttgagttgg ggttaaaggt    3780
gacacgataa gcagaataat taacaaaata tggatgggaa tggtcctaaa tctaaaaata    3840
gttaagaatc gtgggaaata gaaaaaagac aaataaaaga tgatcacgaa atcgccccgt    3900
aataactggt gtgaattaag ttaaaatcat gagtggaggg gttaagacgc caacagaagc    3960
atcgcaactc cacatcaaat agagtaaacc atccatgcga taaagaacaa aaaagaagaa    4020
gaaaattcag accggtcatc atccttattt ggagagaatc tggaacagga gatttccacg    4080
tgataatgat gtcaagattt gactgacaat aggaccatga ggttgatggt cctttatttc    4140 cccgaaaat tatactttgt tttctccaaa gcacttcact tattaattat tgttttcctc    4200
ttttttctca gctgctccat ggggtttata gccacctagt gacgactttg atcatcactc    4260
tttttcctct ttatttattc ttcttgctgc tgagtccgct ttggttactt tttctttttt    4320
ctctttgaaa aacagtagta cacactatca tattcaataa tgtcttcctc ttcttcgtct    4380
tctcttatta ccttaggtca agatgcctca cccacttgca acaacgcctc catttcatcg    4440
tccaaagtag gcctgaatgg tgggtatact ccatttctg gcaagcttca agggatgttg    4500
atggtcgcgt tgttttgtca tggggcgatg gctattttcg agggacccga gatggtacgg    4560
gaaaatccat caataggctg agcccttcca aattggggtc cagtttcgag aggaaaaggt    4620
cgggaaaaga tcaggtgcaa gcttatttta atgaagtgat ggacgtggac cgaatggtag    4680
```

```
atggcgatgt gactgattat gagtggtact ataccgtatc catgacccga tcattcgctg    4740
taggtgacgg gattcttggg aaggctttcg gatcaggctc ccatatttgg ttgggtggag    4800
accatgaact ccaattgtac caatgtgagc gtgttagaga agctcgaatg cgagggattc    4860
aaacattagt ttgtcttcct acatccttcg gggttgtcga attgggatct tctgatatca    4920
tcatggaaga ctggggcacc cttcaactca ctaaatcgat attcagttct gggatccaca    4980
acagcctggg ttcaaatcaa cctgcccatg attcccaacc ccaaatctca accccaagta    5040
ttccttttgt tgattttgga atggtttcag gtgatcaaaa ggagcggatt cttgaagaca    5100
aacaacaagt cgagcccaag aaagaaacca caggtttagg ccgttcgtca tcggaatctg    5160
atggggattt cgcctctgca gacaccgagt tcaatgccgg cggccggtcg aaaaagagag    5220
gtagaaaacc agggaatggg aaagaatccc ctataaacca cgttgaagca gaaaggcaac    5280
gacgtgagag actgaaccat cgtttctacg cacttcgttc cgtggttcca aacgtatcca    5340
agatggacaa agcctcatta ctttcggatg cagtagccta catcaaggaa ctaagatcaa    5400
aaatcgataa actagaggct caactcctag tacaatctga aaaatccaag ttgaacccca    5460
taaatgtttt cgaaaaccaa actaccaaat ccgcattcga caataccatg aaacaatcct    5520
ctacttattg gccaaagaca gtggaagttg atgtgaagat agtaggatcc gaagccatga    5580
ttcgggttcg aagtccagat atcgatcatc cagctgcacg attgatggat gcacttcgag    5640
acctagagct accagttcac catgccagtg tatcaaacgt caatgatctt atgctacaag    5700
atgttgttgt cagagtccct actggaatat tcataaccga cgagatgctt agtactgcaa    5760
tccttcagag atgcacgttg aattaggtag ctagctaggt agccctgcag tgagatgcac    5820 ttttctttt tttgccttct tttgttttt tgtttgatca atgtttcttt cttgttttat    5880
tcgtgcatta gttatttaac atttcctata tatgttctac gtagatagag gtttctatta    5940
caacctgctt ttatcagatt tcatcatttc attggcttta aacagctttg ctatatgcat    6000
gtttcctcac aaacacaaac actggggctt gaacaatgtg gaaactggct acaatataaa    6060
aataattact aaacttagga gctaacttga attttaattg tcgaagttaa gttccaaata    6120
aaaatttaaa cacataagat aacatcaatt acacagcctg aaatccaggc cgcgattaga    6180
ctgtgcttga tgatgatcac                                                6200
```

<210> SEQ ID NO 8
<211> LENGTH: 6153
<212> TYPE: DNA
<213> ORGANISM: Gossyppium hirusutum L.

<400> SEQUENCE: 8

```
cttccctata acaccccaat ccacgtaggt caactgaagt gttacacata tagaaaacag      60
acatgcataa tttgattttt agttcaactt aaatacatat taacttaact aggtgacctc     120
agaaaacttc tacaaaacac aagtttattt aaaaatatac accatagaat aaaagtaaat     180
ggatttaaat attttcgatg aaatactctc ctttgaataa aataataatg gtaacaatta     240
cttataaaac attctggtgt atacaagtag aaataatttc gtaaatgaga acttaacaaa     300
ctttaacaaa tccctcaagg ggtcacattc ttataaatat gtaattgaat gagaaagcta     360
tttattatag attaatattt agaaaatttt aacatgccgc ccccaaaaca tatgcatgtt     420
acaaaaaaaa aaacaaatga agcctactgt agagaatgct tcttttggct tagtcccttc     480
aagaagccca taacaaagat cacctggaag gaaggaaaga aaatgggtaa gtttaaaata     540
acttagtaag ttccacaaag gaaaactcaa cacttaaata agaacagatt cacactacaa     600
```

```
gttcataaca cagaccaata cattagactc tatacgctga acatatggg cgtatactct    660 tatctcattg gcgaacactt aaccttggcg tataacctt cgagcatacc cacatatata    720
gagcatacca tctttcatga aattgggcat acacttatat ccttcctcta catagcacta    780
aaacttaaac agaattgatg cttctgcgtt aacataatct tttttcataa gtacttttgt    840
atcacaacct ctctttaggt gaactcatac ttactttcaa aacttattag ggcgagttca    900
atatatccct catcatttct taatgaatac attatgatct cgatacgtca ataggaatca    960
aacatacttc cttaattatt aatcattctt ttcatctcaa ctgatatatg catcacacaa   1020
acatacacaa tatcgtatta gcttattcct ttcaatacaa atatatcttt ataacaaata   1080
cagagacaaa ttgtcttact acttcataac cttccttagg ttgacctcga attttacata   1140
tcagaacaga tcttttgtat catatcattt cgaacaccta tgtattcttg tgagttcagg   1200
gctatttgct atggttaaca actaacatgt cctatagtag gcagcaccca taacgttagg   1260
ctagttagca actagtatgc cctaccaaaa cttaacaccc acaccaactt gttagtaact   1320
aacatacccc accaatggtc gccaaactat ttaacaacta acatgtccta ctagtggcct   1380
atcatatatc cctatctggt tagcaattaa catgccctac cagtggctca tcttatccgg   1440
atattgagtt catatccgta aggaagtcat ttctatatca tgccacgatt atgcatatat   1500
aacacaggca attacataaa atagaacaca acacagaaaa gaatcacatg gtctggatcc   1560
tcatagatga ttttaagaaa attgttattt tatcactact accgcatgca cactctcttc   1620 tttcttttg ataacttgtt acttttttc ccacgaactc ctcttaacaa gatttcaaag   1680
tataacatag taaaagaaag agaaggaaaa accccactac aaaggttttc actgatattt   1740
atatctcaca gcttcctcac ttagggataa tatgtggcta acatgcaagg ctaactcaat   1800
tctatcctaa ccaacataat tattataggt cattatacat aaaaaaaata atcataaaac   1860
tttggtattt ctaattggat cccaattaaa gcacaactag aactgaatag aaatcacatg   1920
tgcacaaaca aacaatattt acatccagaa tcccacaatc ctttactggc ttacataaag   1980
agaaggtctt aacacacaaa cttttcaaaa gaaacactga ttggcggttc tttaaagtaa   2040
ccacgccaaa acaacttaga cttcacccaa aatacaaatc ttaacaggct tacctataaa   2100
ttatacagtc tgccacacac agcgtacaac tatacaatta ccactctgac gaatacaaca   2160
taaatcagtc ttaccttgac ttaaatctta gctaactttt agcacataca aaccatcaac   2220
aagactacgt tggacagggt attacattcc ctctttattg gacgaaataa gaaacaaata   2280
ttctcttttc tgagagagaa attgggcaaa tgactttgta attaaaggaa taagttgttg   2340
aaagaaggta agaaaattgt attgaaaact attgctcagg atcttcctat ttattgcata   2400
agtgtctttc ttttccttt caacatttgt gatgccttac agaaaatgat gaatttcctt   2460
tgatggggtc agacatagat ggtaataaga aaacacacta agcatcatgg gaaaatttgt   2520
gcaagcctta aagatgtgt tgtatgagtt tccaaaattt aagatgcttt aatcttgtta   2580
tgcttggcaa atagcgttga tggattataa acaatcccaa tcctcttccg agtcaaatat   2640
tcaaagctaa atagttcccg aattgtaggt ttcttgaatc tagtgaagga ttgattgttg   2700
aagacttaga ccatgttta atgatgtata gcaaagctta atttgtattg catgttgttg   2760
ggttaaggcc aatgcaagat tcaaccctgt agtttctttg ctactacctt aatatgcaag   2820
acgctaatga gctgagttgg tatttaagtg tagcatggag catatggaca catatgaacc   2880
gatttatttg gaataaaaaa agatgacaat gtagtttaaa ttgttcaatt tgcatattct   2940
```

-continued

```
tacacgaggc ttggtaggga gctcacacga cgatgactcg tgttcaacct accaggttaa    3000
gttgttctac ttctaagtag tgttggtgca aattgctagg taataggttc aaatgtaaca    3060
ccgatatggt tattttata agaatgttgt cacgagctaa tcggctatca ttcataatga    3120
gaatggtgat tttgacaaag gtcgcacagg ttttatccaa gcaactatga ctctagaagt    3180
tataaatgat tgttgtttga gaggcattgc tttagttgaa gtcgttgcaa attgagagag    3240
tgatcattga gacgaattgt ttgattgtag cgcaagactt aacgagtaaa agcaaggtta    3300
tctctatggt gggtttgatt attgaagact gtctcatgtt gaatgagttg gattagtaga    3360
aacattgata agaccgctca tgctcctgct gttgcaaggg tagctttatg tcatgcaaat    3420
ccttatgttt agaattcttc tcttagttgc atgtcttcca ttcttattta agatgttcct    3480 actttttat ctaatgagtg tatagtataa gccattagct taagaaatta attttccaat    3540
ccttattttg gtagctttgt tgtttccttt ccgatttggt aataatctat ttcttcttt    3600 ccctcgaaaa aacaaggct agggagagtt atttgaataa attaacaaag ttgaagagct    3660
aatttaatag attaacattt gtaccaaata ttaaaacaag gtagttaatt gggagttgag    3720
ttggggttaa aggtgacacg ataagcagaa taattaacaa aatatggatg gaatggtcc    3780 taaatctaaa aatagttaag aatcgtggga aatagaaaaa agacaaataa aagatgatca    3840
cgaaatcgcc ccgtaataac tggtgtgaat taagttaaaa tcatgagtgg aggggttaag    3900
acgccaacag aagcatcgca actccacatc aaatagagta aaccatccat gcgataaaga    3960
acaaaaaaga agaagaaaat tcagaccggt catcatcctt atttggagag aatctggaac    4020
aggagatttc cacgtgataa tgatgtcaag atttgactga caataggacc atgaggttga    4080
tggtccttta ttccccgga aaattatact ttgttttctc caaagcactt cacttattaa    4140
ttattgtttt cctctttttt ctcagctgct ccatggggtt tatagccacc tagtgacgac    4200
tttgatcatc actctttttc ctctttattt attcttcttg ctgctgagtc cgctttggtt    4260
acttttctct ttttctcttt gaaaacagt agtacacact atcatattca ataatgtctt    4320
cctcttcttc gtcttctctt attaccttag gtcaagatgc ctcacccact tgcaacaacg    4380
cctccatttc atcgtccaaa gtaggcctga atggtgggta tactccattt tctggcaagc    4440
ttcaagggat gttgatggtc gcgttgtttt gtcatggggc gatggctatt ttcgagggac    4500
ccgagatggt acgggaaaat ccatcaatag gctgagccct tccaaattgg ggtccagttt    4560
cgagaggaaa aggtcgggaa aagatcaggt gcaagcttat tttaatgaag tgatggacgt    4620
ggaccgaatg gtagatggcg atgtgactga ttatgagtgg tactataccg tatccatgac    4680
ccgatcattc gctgtaggtg acgggattct tgggaaggct ttcggatcag gctcccatat    4740
ttggttgggt ggagaccatg aactccaatt gtaccaatgt gagcgtgtta gagaagctcg    4800
aatgcgaggg attcaaacat tagtttgtct tcctacatcc ttcggggttg tcgaattggg    4860
atcttctgat atcatcatgg aagactgggg caccctttcaa ctcactaaat cgatattcag    4920
ttctgggatc aacaacagcc tgggttcaaa tcaacctgcc catgattccc aaccccaaat    4980
ctcaacccca gtattccctt ttgttgattt tggaatggtt tcaggtgatc aaaaggagcg    5040
gattcttgaa gacaaacaac aagttgagcc caagaaagaa accacaggtt taggccgttc    5100
gtcatcggaa tctgatgggg atttcgcctc tgcagacacc gagttcaatg ccggcggccg    5160
gtcgaaaaag agaggtagaa aaccaggaa tgggaaagaa tccctataa accacgttga    5220 agcagaaagg caacgacgtg agagactgaa ccatcgtttc tacgcacttc gttccgtggt    5280
tccaaacgta tccaagatgg acaaagcctc attactttcg gatgcagtag cctacatcaa    5340
```

```
ggaactaaga tcaaaaatcg ataaactaga ggctcaactc ctagtacaat ctgaaaaatc    5400
caagttgaac cccataaatg ttttcgaaaa ccaaactacc aaatccgcat tcgacaatac    5460
catgaaacaa tcctctactt attggccaaa gacagtggaa gttgatgtga agatagtagg    5520
atccgaagcc atgattcggg ttcgaagtcc agatatcgat catccagctg cacgattgat    5580
ggatgcactt cgagacctag agctaccagt tcaccatgcc agtgtatcaa acgtcaatga    5640
tcttatgcta caagatgttg ttgtcagagt ccctactgga atattcataa ccgacgagat    5700
gcttagtact gcaatccttc agagatgcac gttgaattag gtagctagct aggtagccct    5760
gcagtgagat gcacttttc tttttttgcc ttcttttgtt tttttgtttg atcaatgttt    5820
ctttcttgtt ttattcgtgc attagttatt taacatttcc tatatatgtt ctacgtatag    5880
ataggtttct attacaacct gcttttatca gatttcatca tttcattggc tttaaacagc    5940
tttgctatat gcatgtttcc tcacaaacac aaacactggg gcttgaacaa tgtggaaact    6000
ggctacaata taaaaataat tactaaactt agagctaact tgaattttaa ttgtcgaagt    6060
taagttccaa ataaaaattt aaacacataa gataacatca attacacagc ctgaaatcca    6120
ggccgcgatt agactgtgct tgatgatgat cac                                 6153

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
cggaattcct gggatctccc gaaagctagc                                      30

<210> SEQ ID NO 10
<211> LENGTH: 38
<212> TYPE: DNA
<213> ORGANISM: Artificial Sequence
<220> FEATURE:
<223> OTHER INFORMATION: Primer

<400> SEQUENCE: 10
acgcgagctc ctcattctat ctgtaacatg ccattggc                             38

<210> SEQ ID NO 11
<211> LENGTH: 32
<212> TYPE: DNA
<213> ORGANISM: Artificial Sequence
<220> FEATURE:
<223> OTHER INFORMATION: Primer

<400> SEQUENCE: 11
cggaattcat gagacgaaac tgcaacttgg ag                                   32

<210> SEQ ID NO 12
<211> LENGTH: 34
<212> TYPE: DNA
<213> ORGANISM: Artificial Sequence
<220> FEATURE:
<223> OTHER INFORMATION: Primer

<400> SEQUENCE: 12
acgcgagctc gtaaggagag gtagcttgga ttcg                                 34

<210> SEQ ID NO 13
```

```
<211> LENGTH: 33
<212> TYPE: DNA
<213> ORGANISM: Artificial Sequence
<220> FEATURE:
<223> OTHER INFORMATION: Primer

<400> SEQUENCE: 13
cggaattcat gtcttcctct tcttcgtctt ctc                                    33

<210> SEQ ID NO 14
<211> LENGTH: 33
<212> TYPE: DNA
<213> ORGANISM: Artificial Sequence
<220> FEATURE:
<223> OTHER INFORMATION: Primer

<400> SEQUENCE: 14
acgcgagctc cgatttagtg agttgaaggg tgc                                    33

<210> SEQ ID NO 15
<211> LENGTH: 34
<212> TYPE: DNA
<213> ORGANISM: Artificial Sequence
<220> FEATURE:
<223> OTHER INFORMATION: Primer

<400> SEQUENCE: 15
gctctagaat gtgcaaaggt ttacaacaag gaag                                   34

<210> SEQ ID NO 16
<211> LENGTH: 35
<212> TYPE: DNA
<213> ORGANISM: Artificial Sequence
<220> FEATURE:
<223> OTHER INFORMATION: Primer

<400> SEQUENCE: 16
tcccccgggg ggttgttgaa gactcggttt ccgtg                                  35

<210> SEQ ID NO 17
<211> LENGTH: 31
<212> TYPE: DNA
<213> ORGANISM: Artificial Sequence
<220> FEATURE:
<223> OTHER INFORMATION: Primer

<400> SEQUENCE: 17
gctctagatc aaatgttctt ccctatctcg g                                      31

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18 tcccccggg tcagaaggga gtgtaaatct gca                                     33

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
```

```
gctctagaat ggaagtcctc ataatgtctc cctc                              34
```

<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20

```
tcccccgggg ccagaccaat gagatcggat tc                                32
```

<210> SEQ ID NO 21
<211> LENGTH: 31
<212> TYPE: DNA
<213> ORGANISM: Artificial Sequence
<220> FEATURE:
<223> OTHER INFORMATION: Primer

<400> SEQUENCE: 21

```
cggaattcat ggttggagct ggtgtcctca g                                 31
```

<210> SEQ ID NO 22
<211> LENGTH: 33
<212> TYPE: DNA
<213> ORGANISM: Artificial Sequence
<220> FEATURE:
<223> OTHER INFORMATION: Primer

<400> SEQUENCE: 22

```
acgcgagctc caacagggaa gtagcacaag gcc                               33
```

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23

```
gctctagaat ggaagatgtg gagatggaga                                   30
```

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24

```
tcccccgggg cttcaaagtt gtctttggca tg                                32
```

<210> SEQ ID NO 25
<211> LENGTH: 31
<212> TYPE: DNA
<213> ORGANISM: Artificial Sequence
<220> FEATURE:
<223> OTHER INFORMATION: Primer

<400> SEQUENCE: 25

```
gctctagaat gggcaggaaa tgctcacatt g                                 31
```

<210> SEQ ID NO 26
<211> LENGTH: 33
<212> TYPE: DNA

<213> ORGANISM: Artificial Sequence
<220> FEATURE:
<223> OTHER INFORMATION: Primer

<400> SEQUENCE: 26 tcccccggg aatcaatgca tccgtactgc aac                          33

<210> SEQ ID NO 27
<211> LENGTH: 34
<212> TYPE: DNA
<213> ORGANISM: Artificial Sequence
<220> FEATURE:
<223> OTHER INFORMATION: Primer

<400> SEQUENCE: 27
gctctagaat ggaagaacta atcatctctc catc                        34

<210> SEQ ID NO 28
<211> LENGTH: 33
<212> TYPE: DNA
<213> ORGANISM: Artificial Sequence
<220> FEATURE:
<223> OTHER INFORMATION: Primer

<400> SEQUENCE: 28 tcccccggg gatccaagtt caagaacacc acg                          33

<210> SEQ ID NO 29
<211> LENGTH: 30
<212> TYPE: DNA
<213> ORGANISM: Artificial Sequence
<220> FEATURE:
<223> OTHER INFORMATION: Primer

<400> SEQUENCE: 29
gctctagaat gagcatggtc catggcacca                             30

<210> SEQ ID NO 30
<211> LENGTH: 35
<212> TYPE: DNA
<213> ORGANISM: Artificial Sequence
<220> FEATURE:
<223> OTHER INFORMATION: Primer

<400> SEQUENCE: 30 tcccccggg tatcttaacg atggctgcat gaacc                        35

<210> SEQ ID NO 31
<211> LENGTH: 34
<212> TYPE: DNA
<213> ORGANISM: Artificial Sequence
<220> FEATURE:
<223> OTHER INFORMATION: Primer

<400> SEQUENCE: 31
ctctccaaaa tcaaccatac tcacaaatgc ctac                        34

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
ctccatggca tcctcaagtc acag                                   24

<210> SEQ ID NO 33
<211> LENGTH: 23
<212> TYPE: DNA
<213> ORGANISM: Artificial Sequence
<220> FEATURE:
<223> OTHER INFORMATION: Primer

<400> SEQUENCE: 33
atcttctcac tccgaaaccg acc                                              23

<210> SEQ ID NO 34
<211> LENGTH: 25
<212> TYPE: DNA
<213> ORGANISM: Artificial Sequence
<220> FEATURE:
<223> OTHER INFORMATION: Primer

<400> SEQUENCE: 34
tggaagaaac aagatcggat gtggc                                            25

<210> SEQ ID NO 35
<211> LENGTH: 31
<212> TYPE: DNA
<213> ORGANISM: Artificial Sequence
<220> FEATURE:
<223> OTHER INFORMATION: Primer

<400> SEQUENCE: 35
ggctgtcaga tgtagtaaaa tcagtattgg t                                     31

<210> SEQ ID NO 36
<211> LENGTH: 32
<212> TYPE: DNA
<213> ORGANISM: Artificial Sequence
<220> FEATURE:
<223> OTHER INFORMATION: Primer

<400> SEQUENCE: 36
caaatatata tgggtctgat atgcatgtct cc                                    32

<210> SEQ ID NO 37
<211> LENGTH: 31
<212> TYPE: DNA
<213> ORGANISM: Artificial Sequence
<220> FEATURE:
<223> OTHER INFORMATION: Primer

<400> SEQUENCE: 37
caaagtgttg atttcagcaa taacttgtag c                                     31

<210> SEQ ID NO 38
<211> LENGTH: 32
<212> TYPE: DNA
<213> ORGANISM: Artificial Sequence
<220> FEATURE:
<223> OTHER INFORMATION: Primer

<400> SEQUENCE: 38
cgtaacaaaa tggttttcgt atgttacgta tc                                    32

<210> SEQ ID NO 39
<211> LENGTH: 37
<212> TYPE: DNA
<213> ORGANISM: Artificial Sequence
<220> FEATURE:

<223> OTHER INFORMATION: Primer

<400> SEQUENCE: 39
catcccatac aaactattaa caagattacg tcggatg 37

<210> SEQ ID NO 40
<211> LENGTH: 27
<212> TYPE: DNA
<213> ORGANISM: Artificial Sequence
<220> FEATURE:
<223> OTHER INFORMATION: Primer

<400> SEQUENCE: 40
gtgatcatca tcaagcacag gctactg 27

<210> SEQ ID NO 41
<211> LENGTH: 28
<212> TYPE: DNA
<213> ORGANISM: Artificial Sequence
<220> FEATURE:
<223> OTHER INFORMATION: Primer

<400> SEQUENCE: 41
caaaccatca acaagactac gttggaca 28

<210> SEQ ID NO 42
<211> LENGTH: 36
<212> TYPE: DNA
<213> ORGANISM: Artificial Sequence
<220> FEATURE:
<223> OTHER INFORMATION: Primer

<400> SEQUENCE: 42
ctaatttaag tgatcatcat caagcacagt ctaatc 36

<210> SEQ ID NO 43
<211> LENGTH: 22
<212> TYPE: DNA
<213> ORGANISM: Artificial Sequence
<220> FEATURE:
<223> OTHER INFORMATION: Primer

<400> SEQUENCE: 43
ccagcttcgg tccagttcct ta 22

<210> SEQ ID NO 44
<211> LENGTH: 30
<212> TYPE: DNA
<213> ORGANISM: Artificial Sequence
<220> FEATURE:
<223> OTHER INFORMATION: Primer

<400> SEQUENCE: 44
gaggaatctt tcttggtttg gttattgtta 30

<210> SEQ ID NO 45
<211> LENGTH: 26
<212> TYPE: DNA
<213> ORGANISM: Artificial Sequence
<220> FEATURE:
<223> OTHER INFORMATION: Primer

<400> SEQUENCE: 45
aaccccagct tcgatccagt ttcttg 26

```
<210> SEQ ID NO 46
<211> LENGTH: 29
<212> TYPE: DNA
<213> ORGANISM: Artificial Sequence
<220> FEATURE:
<223> OTHER INFORMATION: Primer

<400> SEQUENCE: 46
aggaatcttt cttggtttgg ttattgctg                                    29

<210> SEQ ID NO 47
<211> LENGTH: 25
<212> TYPE: DNA
<213> ORGANISM: Artificial Sequence
<220> FEATURE:
<223> OTHER INFORMATION: Primer

<400> SEQUENCE: 47
cagatagaat gagtagtgct gcaat                                        25

<210> SEQ ID NO 48
<211> LENGTH: 22
<212> TYPE: DNA
<213> ORGANISM: Artificial Sequence
<220> FEATURE:
<223> OTHER INFORMATION: Primer

<400> SEQUENCE: 48
ggcctcagtg aagaaatcat cg                                           22

<210> SEQ ID NO 49
<211> LENGTH: 25
<212> TYPE: DNA
<213> ORGANISM: Artificial Sequence
<220> FEATURE:
<223> OTHER INFORMATION: Primer

<400> SEQUENCE: 49
cagatagaat gagtagtgct gcaac                                        25

<210> SEQ ID NO 50
<211> LENGTH: 27
<212> TYPE: DNA
<213> ORGANISM: Artificial Sequence
<220> FEATURE:
<223> OTHER INFORMATION: Primer

<400> SEQUENCE: 50
caattggcct cagtgaagaa atcatca                                      27

<210> SEQ ID NO 51
<211> LENGTH: 25
<212> TYPE: DNA
<213> ORGANISM: Artificial Sequence
<220> FEATURE:
<223> OTHER INFORMATION: Primer

<400> SEQUENCE: 51
tgtgaagata gtaggatccg aagct                                        25

<210> SEQ ID NO 52
<211> LENGTH: 24
<212> TYPE: DNA
<213> ORGANISM: Artificial Sequence
<220> FEATURE:
<223> OTHER INFORMATION: Primer
```

```
<400> SEQUENCE: 52
gtagggactc tgacaacaac atcc                                          24

<210> SEQ ID NO 53
<211> LENGTH: 25
<212> TYPE: DNA
<213> ORGANISM: Artificial Sequence
<220> FEATURE:
<223> OTHER INFORMATION: Primer

<400> SEQUENCE: 53
tgtgaagata gtaggatccg aagcc                                         25

<210> SEQ ID NO 54
<211> LENGTH: 24
<212> TYPE: DNA
<213> ORGANISM: Artificial Sequence
<220> FEATURE:
<223> OTHER INFORMATION: Primer

<400> SEQUENCE: 54
gtagggactc tgacaacaac atct                                          24

<210> SEQ ID NO 55
<211> LENGTH: 26
<212> TYPE: DNA
<213> ORGANISM: Artificial sequence
<220> FEATURE:
<223> OTHER INFORMATION: Oligonucleotide

<400> SEQUENCE: 55
gttatttgat tgcttcgtca gttacg                                        26

<210> SEQ ID NO 56
<211> LENGTH: 24
<212> TYPE: DNA
<213> ORGANISM: Artificial sequence
<220> FEATURE:
<223> OTHER INFORMATION: Oligonucleotide

<400> SEQUENCE: 56
gtttcctata ctaaactcaa gagg                                          24

<210> SEQ ID NO 57
<211> LENGTH: 24
<212> TYPE: DNA
<213> ORGANISM: Artificial sequence
<220> FEATURE:
<223> OTHER INFORMATION: Oligonucleotide

<400> SEQUENCE: 57
ttactgcaga tctagcctcc tgag                                          24

<210> SEQ ID NO 58
<211> LENGTH: 23
<212> TYPE: DNA
<213> ORGANISM: Artificial sequence
<220> FEATURE:
<223> OTHER INFORMATION: Oligonucleotide

<400> SEQUENCE: 58
gagcgtagaa tctgtggttc agc                                           23

<210> SEQ ID NO 59
<211> LENGTH: 24
```

```
<212> TYPE: DNA
<213> ORGANISM: Artificial sequence
<220> FEATURE:
<223> OTHER INFORMATION: Oligonucleotide

<400> SEQUENCE: 59
gcaactcatg agcaccagtt aacc                                           24

<210> SEQ ID NO 60
<211> LENGTH: 22
<212> TYPE: DNA
<213> ORGANISM: Artificial sequence
<220> FEATURE:
<223> OTHER INFORMATION: Oligonucleotide

<400> SEQUENCE: 60
tcctgggaaa aggaaaccag ag                                             22

<210> SEQ ID NO 61
<211> LENGTH: 27
<212> TYPE: DNA
<213> ORGANISM: Artificial sequence
<220> FEATURE:
<223> OTHER INFORMATION: Oligonucleotide

<400> SEQUENCE: 61
tgtcacatta gcatgaggta catgtgg                                        27

<210> SEQ ID NO 62
<211> LENGTH: 24
<212> TYPE: DNA
<213> ORGANISM: Artificial sequence
<220> FEATURE:
<223> OTHER INFORMATION: Oligonucleotide

<400> SEQUENCE: 62
taaggtacac gaggcacagc acac                                           24

<210> SEQ ID NO 63
<211> LENGTH: 25
<212> TYPE: DNA
<213> ORGANISM: Artificial sequence
<220> FEATURE:
<223> OTHER INFORMATION: Oligonucleotide

<400> SEQUENCE: 63
agagagtgaa tcgtacttct tctgc                                          25

<210> SEQ ID NO 64
<211> LENGTH: 22
<212> TYPE: DNA
<213> ORGANISM: Artificial sequence
<220> FEATURE:
<223> OTHER INFORMATION: Oligonucleotide

<400> SEQUENCE: 64
atgatgaacg tcgacgacgt cc                                             22

<210> SEQ ID NO 65
<211> LENGTH: 26
<212> TYPE: DNA
<213> ORGANISM: Artificial sequence
<220> FEATURE:
<223> OTHER INFORMATION: Oligonucleotide

<400> SEQUENCE: 65
```
tcgcttgaag attcgacata tggtcc    26

<210> SEQ ID NO 66
<211> LENGTH: 28
<212> TYPE: DNA
<213> ORGANISM: Artificial sequence
<220> FEATURE:
<223> OTHER INFORMATION: Oligonucleotide

<400> SEQUENCE: 66
gcaaccctac tcctatactt caatctag    28

<210> SEQ ID NO 67
<211> LENGTH: 22
<212> TYPE: DNA
<213> ORGANISM: Artificial sequence
<220> FEATURE:
<223> OTHER INFORMATION: Oligonucleotide

<400> SEQUENCE: 67
gctagatgtg gtgttgcctc ac    22

<210> SEQ ID NO 68
<211> LENGTH: 33
<212> TYPE: DNA
<213> ORGANISM: Artificial sequence
<220> FEATURE:
<223> OTHER INFORMATION: Oligonucleotide

<400> SEQUENCE: 68
caagaatagt ctaagcttct ctagcaaatg atc    33

<210> SEQ ID NO 69
<211> LENGTH: 25
<212> TYPE: DNA
<213> ORGANISM: Artificial sequence
<220> FEATURE:
<223> OTHER INFORMATION: Oligonucleotide

<400> SEQUENCE: 69
actggagtac atccatgtca gtctc    25

<210> SEQ ID NO 70
<211> LENGTH: 24
<212> TYPE: DNA
<213> ORGANISM: Artificial sequence
<220> FEATURE:
<223> OTHER INFORMATION: Oligonucleotide

<400> SEQUENCE: 70
agttctggga tcaacaacag cctg    24

<210> SEQ ID NO 71
<211> LENGTH: 24
<212> TYPE: DNA
<213> ORGANISM: Artificial sequence
<220> FEATURE:
<223> OTHER INFORMATION: Oligonucleotide

<400> SEQUENCE: 71
ggccaaagac agtggaagtt gatg    24

<210> SEQ ID NO 72
<211> LENGTH: 25
<212> TYPE: DNA
<213> ORGANISM: Artificial sequence

```
<220> FEATURE:
<223> OTHER INFORMATION: Oligonucleotide

<400> SEQUENCE: 72
atgtcttcct cttcttcgtc ttctc                                  25

<210> SEQ ID NO 73
<211> LENGTH: 33
<212> TYPE: DNA
<213> ORGANISM: Artificial sequence
<220> FEATURE:
<223> OTHER INFORMATION: Oligonucleotide

<400> SEQUENCE: 73
ggtttcttga atctagtgaa ggattgattg ttg                         33

<210> SEQ ID NO 74
<211> LENGTH: 29
<212> TYPE: DNA
<213> ORGANISM: Artificial sequence
<220> FEATURE:
<223> OTHER INFORMATION: Oligonucleotide

<400> SEQUENCE: 74
ttgcaaattg agagagtgat cattgagac                              29

<210> SEQ ID NO 75
<211> LENGTH: 24
<212> TYPE: DNA
<213> ORGANISM: Artificial sequence
<220> FEATURE:
<223> OTHER INFORMATION: Oligonucleotide

<400> SEQUENCE: 75
catgagtgga ggggttaaga cgcc                                   24

<210> SEQ ID NO 76
<211> LENGTH: 25
<212> TYPE: DNA
<213> ORGANISM: Artificial sequence
<220> FEATURE:
<223> OTHER INFORMATION: Oligonucleotide

<400> SEQUENCE: 76
tgacactgct agtgcagtca ctctg                                  25

<210> SEQ ID NO 77
<211> LENGTH: 28
<212> TYPE: DNA
<213> ORGANISM: Artificial sequence
<220> FEATURE:
<223> OTHER INFORMATION: Oligonucleotide

<400> SEQUENCE: 77
gacacaagca tcatagtcac atcttgtg                               28

<210> SEQ ID NO 78
<211> LENGTH: 29
<212> TYPE: DNA
<213> ORGANISM: Artificial sequence
<220> FEATURE:
<223> OTHER INFORMATION: Oligonucleotide

<400> SEQUENCE: 78
taactggaag gttctatacc aatggactc                              29
```

<210> SEQ ID NO 79
<211> LENGTH: 30
<212> TYPE: DNA
<213> ORGANISM: Artificial sequence
<220> FEATURE:
<223> OTHER INFORMATION: Oligonucleotide

<400> SEQUENCE: 79
caaataacaa gcagtattaa cagcttcagc                                              30

<210> SEQ ID NO 80
<211> LENGTH: 25
<212> TYPE: DNA
<213> ORGANISM: Artificial sequence
<220> FEATURE:
<223> OTHER INFORMATION: Oligonucleotide

<400> SEQUENCE: 80
atatgccata acttcgtggt gtcag                                                   25

<210> SEQ ID NO 81
<211> LENGTH: 24
<212> TYPE: DNA
<213> ORGANISM: Artificial sequence
<220> FEATURE:
<223> OTHER INFORMATION: Oligonucleotide

<400> SEQUENCE: 81
ttcttggact gcgatctagg atgg                                                    24

<210> SEQ ID NO 82
<211> LENGTH: 23
<212> TYPE: DNA
<213> ORGANISM: Artificial sequence
<220> FEATURE:
<223> OTHER INFORMATION: Oligonucleotide

<400> SEQUENCE: 82
gcaatccttg ttgaaccagc act                                                     23

<210> SEQ ID NO 83
<211> LENGTH: 29
<212> TYPE: DNA
<213> ORGANISM: Artificial sequence
<220> FEATURE:
<223> OTHER INFORMATION: Oligonucleotide

<400> SEQUENCE: 83
aagccatttc ttaacaaatc tccaccttg                                               29

<210> SEQ ID NO 84
<211> LENGTH: 25
<212> TYPE: DNA
<213> ORGANISM: Artificial sequence
<220> FEATURE:
<223> OTHER INFORMATION: Oligonucleotide

<400> SEQUENCE: 84
agctcaattt ggggagttta cttgc                                                   25

<210> SEQ ID NO 85
<211> LENGTH: 28
<212> TYPE: DNA
<213> ORGANISM: Artificial sequence
<220> FEATURE:
<223> OTHER INFORMATION: Oligonucleotide

<400> SEQUENCE: 85
gtaagttcca caaaggaaaa ctcaacac                                28

<210> SEQ ID NO 86
<211> LENGTH: 25
<212> TYPE: DNA
<213> ORGANISM: Artificial sequence
<220> FEATURE:
<223> OTHER INFORMATION: Oligonucleotide

<400> SEQUENCE: 86
cataaccttc cttaggttga cctcg                                   25

<210> SEQ ID NO 87
<211> LENGTH: 26
<212> TYPE: DNA
<213> ORGANISM: Artificial sequence
<220> FEATURE:
<223> OTHER INFORMATION: Oligonucleotide

<400> SEQUENCE: 87
gaatcacatg gtctggatcc tcatag                                  26

<210> SEQ ID NO 88
<211> LENGTH: 21
<212> TYPE: DNA
<213> ORGANISM: Artificial sequence
<220> FEATURE:
<223> OTHER INFORMATION: Oligonucleotide

<400> SEQUENCE: 88
agaaacactg attggcggtt c                                       21

<210> SEQ ID NO 89
<211> LENGTH: 26
<212> TYPE: DNA
<213> ORGANISM: Artificial sequence
<220> FEATURE:
<223> OTHER INFORMATION: Oligonucleotide

<400> SEQUENCE: 89
ggaatgtaat accctgtcca acgtag                                  26

<210> SEQ ID NO 90
<211> LENGTH: 26
<212> TYPE: DNA
<213> ORGANISM: Artificial sequence
<220> FEATURE:
<223> OTHER INFORMATION: Oligonucleotide

<400> SEQUENCE: 90
cgatattgtg tatgtttgtg tgatgc                                  26

<210> SEQ ID NO 91
<211> LENGTH: 68
<212> TYPE: DNA
<213> ORGANISM: Artificial sequence
<220> FEATURE:
<223> OTHER INFORMATION: Oligonucleotide

<400> SEQUENCE: 91
tcgagctcgg tacccgggga tcctctagag tcgacctgca gcaaaccatc aacaagacta    60
cgttggac                                                            68

<210> SEQ ID NO 92
<211> LENGTH: 91
<212> TYPE: DNA
<213> ORGANISM: Artificial sequence
<220> FEATURE:
<223> OTHER INFORMATION: Oligonucleotide

<400> SEQUENCE: 92
gaaggagaaa aactagaaat ttaccctcag atctaccata agctttattg aatatgatag     60
tgtgtactac tgttttcaa agagaaaaaa g                                    91

<210> SEQ ID NO 93
<211> LENGTH: 66
<212> TYPE: DNA
<213> ORGANISM: Artificial sequence
<220> FEATURE:
<223> OTHER INFORMATION: Oligonucleotide

<400> SEQUENCE: 93
tcgagctcgg tacccgggga tcctctagag tcgacctgca gcttccctat aacaccccaa     60
tccacg                                                               66

<210> SEQ ID NO 94
<211> LENGTH: 20
<212> TYPE: DNA
<213> ORGANISM: Artificial sequence
<220> FEATURE:
<223> OTHER INFORMATION: Oligonucleotide

<400> SEQUENCE: 94
gctcaaacag gtgatcatca                                                 20

<210> SEQ ID NO 95
<211> LENGTH: 21
<212> TYPE: DNA
<213> ORGANISM: Artificial sequence
<220> FEATURE:
<223> OTHER INFORMATION: Oligonucleotide

<400> SEQUENCE: 95
gattggaaaa ggcgacgaca g                                               21

<210> SEQ ID NO 96
<211> LENGTH: 20
<212> TYPE: DNA
<213> ORGANISM: Artificial sequence
<220> FEATURE:
<223> OTHER INFORMATION: Oligonucleotide

<400> SEQUENCE: 96
aattggggtc cagtttcgag                                                 20

<210> SEQ ID NO 97
<211> LENGTH: 20
<212> TYPE: DNA
<213> ORGANISM: Artificial sequence
<220> FEATURE:
<223> OTHER INFORMATION: Oligonucleotide

<400> SEQUENCE: 97
agtgatggac gtggaccgta                                                 20

<210> SEQ ID NO 98
<211> LENGTH: 21

<212> TYPE: DNA
<213> ORGANISM: Artificial sequence
<220> FEATURE:
<223> OTHER INFORMATION: Oligonucleotide

<400> SEQUENCE: 98
gcttctctaa cacgctcaca c                                    21

<210> SEQ ID NO 99
<211> LENGTH: 31
<212> TYPE: DNA
<213> ORGANISM: Artificial sequence
<220> FEATURE:
<223> OTHER INFORMATION: Oligonucleotide

<400> SEQUENCE: 99
gtactcaagt tgatgatgtg tgttggtgat g                         31

<210> SEQ ID NO 100
<211> LENGTH: 31
<212> TYPE: DNA
<213> ORGANISM: Artificial sequence
<220> FEATURE:
<223> OTHER INFORMATION: Oligonucleotide

<400> SEQUENCE: 100
tctagcaagt tgatgatgtg tgttggtgat g                         31

<210> SEQ ID NO 101
<211> LENGTH: 31
<212> TYPE: DNA
<213> ORGANISM: Artificial sequence
<220> FEATURE:
<223> OTHER INFORMATION: Oligonucleotide

<400> SEQUENCE: 101
gagtcaaagt tgatgatgtg tgttggtgat g                         31

<210> SEQ ID NO 102
<211> LENGTH: 31
<212> TYPE: DNA
<213> ORGANISM: Artificial sequence
<220> FEATURE:
<223> OTHER INFORMATION: Oligonucleotide

<400> SEQUENCE: 102
gctagtaagt tgatgatgtg tgttggtgat g                         31

<210> SEQ ID NO 103
<211> LENGTH: 31
<212> TYPE: DNA
<213> ORGANISM: Artificial sequence
<220> FEATURE:
<223> OTHER INFORMATION: Oligonucleotide

<400> SEQUENCE: 103
atgctaaagt tgatgatgtg tgttggtgat g                         31

<210> SEQ ID NO 104
<211> LENGTH: 31
<212> TYPE: DNA
<213> ORGANISM: Artificial sequence
<220> FEATURE:
<223> OTHER INFORMATION: Oligonucleotide

<400> SEQUENCE: 104
ctgcgaaagt tgatgatgtg tgttggtgat g                                31

<210> SEQ ID NO 105
<211> LENGTH: 32
<212> TYPE: DNA
<213> ORGANISM: Artificial sequence
<220> FEATURE:
<223> OTHER INFORMATION: Oligonucleotide

<400> SEQUENCE: 105
cgactgataa cattgattaa cccaacttga gc                               32

<210> SEQ ID NO 106
<211> LENGTH: 32
<212> TYPE: DNA
<213> ORGANISM: Artificial sequence
<220> FEATURE:
<223> OTHER INFORMATION: Oligonucleotide

<400> SEQUENCE: 106
tgatagataa cattgattaa cccaacttga gc                               32

<210> SEQ ID NO 107
<211> LENGTH: 32
<212> TYPE: DNA
<213> ORGANISM: Artificial sequence
<220> FEATURE:
<223> OTHER INFORMATION: Oligonucleotide

<400> SEQUENCE: 107
gtcacgataa cattgattaa cccaacttga gc                               32

<210> SEQ ID NO 108
<211> LENGTH: 32
<212> TYPE: DNA
<213> ORGANISM: Artificial sequence
<220> FEATURE:
<223> OTHER INFORMATION: Oligonucleotide

<400> SEQUENCE: 108
atgatgataa cattgattaa cccaacttga gc                               32

<210> SEQ ID NO 109
<211> LENGTH: 32
<212> TYPE: DNA
<213> ORGANISM: Artificial sequence
<220> FEATURE:
<223> OTHER INFORMATION: Oligonucleotide

<400> SEQUENCE: 109
cagtcaataa cattgattaa cccaacttga gc                               32

<210> SEQ ID NO 110
<211> LENGTH: 32
<212> TYPE: DNA
<213> ORGANISM: Artificial sequence
<220> FEATURE:
<223> OTHER INFORMATION: Oligonucleotide

<400> SEQUENCE: 110
acgtcaataa cattgattaa cccaacttga gc                               32

<210> SEQ ID NO 111
<211> LENGTH: 28
<212> TYPE: DNA
<213> ORGANISM: Artificial sequence

```
<220> FEATURE:
<223> OTHER INFORMATION: Oligonucleotide

<400> SEQUENCE: 111
gtactccttc aagggatgtt gatggtcg                                    28

<210> SEQ ID NO 112
<211> LENGTH: 28
<212> TYPE: DNA
<213> ORGANISM: Artificial sequence
<220> FEATURE:
<223> OTHER INFORMATION: Oligonucleotide

<400> SEQUENCE: 112
tctagccttc aagggatgtt gatggtcg                                    28

<210> SEQ ID NO 113
<211> LENGTH: 28
<212> TYPE: DNA
<213> ORGANISM: Artificial sequence
<220> FEATURE:
<223> OTHER INFORMATION: Oligonucleotide

<400> SEQUENCE: 113
gagtcacttc aagggatgtt gatggtcg                                    28

<210> SEQ ID NO 114
<211> LENGTH: 28
<212> TYPE: DNA
<213> ORGANISM: Artificial sequence
<220> FEATURE:
<223> OTHER INFORMATION: Oligonucleotide

<400> SEQUENCE: 114
gctagtcttc aagggatgtt gatggtcg                                    28

<210> SEQ ID NO 115
<211> LENGTH: 28
<212> TYPE: DNA
<213> ORGANISM: Artificial sequence
<220> FEATURE:
<223> OTHER INFORMATION: Oligonucleotide

<400> SEQUENCE: 115
atgctacttc aagggatgtt gatggtcg                                    28

<210> SEQ ID NO 116
<211> LENGTH: 28
<212> TYPE: DNA
<213> ORGANISM: Artificial sequence
<220> FEATURE:
<223> OTHER INFORMATION: Oligonucleotide

<400> SEQUENCE: 116
ctgcgacttc aagggatgtt gatggtcg                                    28

<210> SEQ ID NO 117
<211> LENGTH: 31
<212> TYPE: DNA
<213> ORGANISM: Artificial sequence
<220> FEATURE:
<223> OTHER INFORMATION: Oligonucleotide

<400> SEQUENCE: 117
cgactgatcg atttagtgag ttgaagggtg c                                31
```

```
<210> SEQ ID NO 118
<211> LENGTH: 31
<212> TYPE: DNA
<213> ORGANISM: Artificial sequence
<220> FEATURE:
<223> OTHER INFORMATION: Oligonucleotide

<400> SEQUENCE: 118
tgatagatcg atttagtgag ttgaagggtg c                              31

<210> SEQ ID NO 119
<211> LENGTH: 31
<212> TYPE: DNA
<213> ORGANISM: Artificial sequence
<220> FEATURE:
<223> OTHER INFORMATION: Oligonucleotide

<400> SEQUENCE: 119
gtcacgatcg atttagtgag ttgaagggtg c                              31

<210> SEQ ID NO 120
<211> LENGTH: 31
<212> TYPE: DNA
<213> ORGANISM: Artificial sequence
<220> FEATURE:
<223> OTHER INFORMATION: Oligonucleotide

<400> SEQUENCE: 120
atgatgatcg atttagtgag ttgaagggtg c                              31

<210> SEQ ID NO 121
<211> LENGTH: 31
<212> TYPE: DNA
<213> ORGANISM: Artificial sequence
<220> FEATURE:
<223> OTHER INFORMATION: Oligonucleotide

<400> SEQUENCE: 121
cagtcaatcg atttagtgag ttgaagggtg c                              31

<210> SEQ ID NO 122
<211> LENGTH: 31
<212> TYPE: DNA
<213> ORGANISM: Artificial sequence
<220> FEATURE:
<223> OTHER INFORMATION: Oligonucleotide

<400> SEQUENCE: 122
acgtcaatcg atttagtgag ttgaagggtg c                              31
```

METHODS AND COMPOSITIONS FOR MODULATING GOSSYPOL CONTENT IN COTTON PLANTS

CROSS REFERENCE TO RELATED APPLICATIONS

This application claims the benefit of U.S. Provisional Application 62/571,611, filed Oct. 12, 2017, which is incorporated herein by reference in its entirety.

FIELD OF THE INVENTION

The present disclosure relates generally to the field of agriculture and plant genetics. More specifically, the present disclosure provides genetically modified cotton plants comprising modified gossypol content.

INCORPORATION OF SEQUENCE LISTING

The sequence listing that is contained in the file named "TAMC053US_ST25.txt," which is 74 kilobytes as measured in Microsoft Windows operating system and was created on Oct. 11, 2018, is filed electronically herewith and incorporated herein by reference.

BACKGROUND OF THE INVENTION

Cotton (*Gossypium hirsutum* L.) is an important crop in many areas of the world. An attribute of cotton not widely recognized is that for every 1 kilogram (kg) of fiber, the plant produces approximately 1.65 kg of seed. This makes cotton the third largest field crop in terms of edible oilseed tonnage in the world. However, the ability to utilize the seed and oil is hampered by the presence of a toxic terpenoid, gossypol. The presence of gossypol, a cardio- and hepatotoxic terpenoid unique to the tribe Gossypieae, in the seed glands renders cottonseed unsafe for human and monogastric animal consumption.

Therefore, eliminating the glands in the seed only, while retaining terpenoids in rest of the plant, is a highly desirable goal.

SUMMARY OF THE INVENTION

The present disclosure provides a cotton plant exhibiting artificially down-regulated CGF2 gene expression, wherein the plant exhibits reduced gossypol content in seed. In certain embodiments, the plant comprises a mutated genomic CGF2 gene. In particular embodiments the mutated genomic CGF2 gene is produced by irradiation, gene editing, T-DNA insertion, transposon insertion, or chemical mutagenesis. In other embodiments the plant comprises an RNAi, CRISPR, CRISPRi, or C2c2 construct directed against the CGF2 gene or a transcript thereof. In additional embodiments the RNAi, CRISPR, CRISPRi, or C2c2 construct comprises all or a portion of SEQ ID NO:3, a polynucleotide that encodes SEQ ID NO:4, or a complement thereof. In further embodiments the RNAi, CRISPR, CRISPRi, or C2c2 construct is operably linked to a seed-specific promoter. Seed-specific promoters that can be used in embodiments of the present disclosure include, but are not limited to, a cotton α-globulin gene B promoter. In certain embodiments the plant further exhibits artificially down-regulated CGF1 and/or CGF3 gene expression. In additional embodiments, the plant further exhibits artificially down-regulated δ-cadinene synthase gene expression.

In yet other embodiments the plant further exhibits increased CGF2 gene expression in leaves of the plant. In some embodiments the plant further exhibits increased CGF1 and/or CGF3 gene expression in leaves of the plant. In particular embodiments the CGF1, CGF2 and CGF3 gene expression is controlled by a leaf-specific or green tissue-specific promoter. In certain embodiments the plant is a *Gossypium hirsutum* cotton plant. In additional embodiments the plant is further defined as an T0 transgenic plant. In other embodiments the plant is further defined as a progeny plant of any generation of an T0 transgenic plant, wherein the transgenic plant has inherited the mutated genomic CGF2 gene from the T0 transgenic plant.

The present disclosure also provides a plant part of the presently disclosed plants, wherein the plant part comprises a cell of the plant. In certain embodiments the plant part is a protoplast, cell, meristem, root, pistil, anther, flower, embryo, stalk or petiole. Additionally, the present disclosure provides a seed that produces the presently disclosed plants.

The present disclosure further provides a method of reducing gossypol content in seed in a plant comprising down-regulating expression of a CGF2 gene in seed in the plant, wherein the gossypol content in seed of the plant is reduced when compared to a plant exhibiting normal CGF2 expression. In some embodiments, reducing expression of the CGF2 gene comprises RNAi, CRISPR, CRISPRi, or C2c2-mediated transcript destruction, gene editing, or mutation of the genomic CGF2 gene. In additional embodiments, down-regulating the expression of the CGF2 gene comprises expressing in the plant a RNA molecule complementary to all or a portion of SEQ ID NO:3 or a polynucleotide that encodes SEQ ID NO:4. In certain embodiments, expression of the RNA molecule is regulated by a seed-specific promoter, such as a cotton α-globulin gene B promoter. In some embodiments the RNA molecule is a single stranded RNA molecule, while in other embodiments the RNA molecule is a double stranded RNA molecule.

In certain embodiments of the presently disclosed methods, the CGF2 gene is mutated using irradiation, gene editing, T-DNA insertion, transposon insertion, or chemical mutagenesis. In further embodiments, expression of CGF1 and/or CGF3 expression is also down-regulated. In still further embodiments, expression of δ-cadinene synthase gene expression is also down-regulated.

In yet other embodiments of the presently disclosed methods, the plant further exhibits increased CGF2 gene expression in leaves of the plant. In certain embodiments the plant further exhibits increased CGF1 and/or CGF3 gene expression in leaves of the plant. In particular embodiments the CGF1, CGF2 and CGF3 gene expression is controlled by a leaf-specific or green tissue-specific promoter. In some embodiments the plant is a *Gossypium hirsutum* cotton plant.

The present disclosure additionally provides a plant produced by the presently disclosed methods, wherein the plant comprises reduced gossypol content in seed. In some embodiments the plant further exhibits increased CGF2 gene expression in leaves of the plant. In particular embodiments the plant is a *Gossypium hirsutum* cotton plant. The present disclosure also provides a seed that produces the presently disclosed plants.

Furthermore, the present disclosure provides a method of producing cotton seeds with reduced gossypol accumulation comprising obtaining a plant exhibiting artificially down-regulated CGF2 gene expression, wherein the plant exhibits reduced gossypol content in seed, and cultivating the plant to produce seed.

The present disclosure also provides a method of plant breeding comprising identifying a plant comprising a reduced level or function of a CGF2 gene product relative to that found in an otherwise isogenic plant that displays a wild-type level of function of a CGF2 gene product, and selecting the plant for crossing with a second plant. In certain embodiments the step of identifying comprises at least one method selected from the group consisting of PCR, single strand conformational polymorphism analysis, denaturing gradient gel electrophoresis, cleavage fragment length polymorphism analysis and/or DNA sequencing. In some embodiments, the method further comprises assaying a cotton plant for the presence of a polymorphism genetically linked to CGF2 gene with a reduced level of function of the product of the gene, and selecting at least a first crop plant comprising the polymorphism and reduced level of function of the product. In other embodiments, the method further comprises crossing the first crop plant with a second crop plant of the same species or variety to produce a progeny plant comprising the polymorphism. In additional embodiments the polymorphism comprises an insertion, a deletion, an insertion or a single nucleotide polymorphism (SNP). In yet other embodiments the plant further comprises a reduced level of function of a CGF1 and/or CGF3 and/or δ-cadinene synthase gene product relative to that found in an otherwise isogenic plant that displays a wild-type level of function of a CGF1 and/or CGF3 and/or δ-cadinene synthase gene product.

The present disclosure additionally provides a method of producing food, feed, or oil comprising obtaining a plant exhibiting artificially down-regulated CGF2 gene expression, wherein the plant exhibits reduced gossypol content in seed, cultivating the plant to obtain a plant product, and preparing food, feed, or oil from the plant or plant product. In certain embodiments the food, feed or oil comprises reduced gossypol relative to a plant lacking the down-regulated activity of a CGF2 gene product.

BRIEF DESCRIPTION OF THE SEQUENCE LISTING

SEQ ID NO:1—CGF1 gene sequence in A-Genome (Gh_A11G0909) of *Gossypium hirsutum* L. There are no sequence differences between glanded (GL; GVS4) and glandless (gl; GVS5) Stoneville 7A cotton. Promoter sequence; nucleotides 1-1585. 5'-UTR sequence; nucleotides 1586-1611. Coding sequence, nucleotides 1612-3099. 3'-UTR sequence; nucleotides 3100-3364. Terminator sequence; nucleotides 3365-3467.

SEQ ID NO:2—CGF1 gene sequence in D-Genome (Gh_D11G1055) of *Gossypium hirsutum* L. There are no sequence differences between glanded (GL; GVS4) and glandless (gl; GVS5) Stoneville 7A cotton. Promoter sequence; nucleotides 1-1515. 5'-UTR sequence; nucleotides 1516-1543. Coding sequence; nucleotides 1544-3031. 3'-UTR sequence; nucleotides 3032-3304. Terminator sequence; nucleotides 3305-3769.

SEQ ID NO:3—CGF2 gene sequence in A-Genome (Gh_A01G0267) of *Gossypium hirsutum* L. There are no sequence differences between glanded (GL; GVS4) and glandless (gl; GVS5) Stoneville 7A cotton. Promoter sequence; nucleotides 1-1803. 5'-UTR sequence; nucleotides 1804-1913. Coding sequence; nucleotides 1914-2111, 2357-2686, 3226-3653. Intron sequences; nucleotides 2112-2356, 2687-3225. 3'-UTR sequence; nucleotides 3654-3845. Terminator sequence; nucleotides 3846-4264.

SEQ ID NO:4—CGF2 gene sequence in D-Genome (Gh_D01G0278) of *Gossypium hirsutum* L. There are no sequence differences between glanded (GL; GVS4) and glandless (gl; GVS5) Stoneville 7A cotton. Promoter sequence; nucleotides 1-1651. 5'-UTR sequence; nucleotides 1652-1783. Coding sequence; nucleotides 1784-1982, 2228-2557, 3102-3532. Intron sequences; nucleotides 1983-2227, 2558-3101. 3'-UTR sequence; nucleotides 3533-3772. Terminator sequence; nucleotides 3773-3968.

SEQ ID NO:5—CGF3 gene sequence in A-Genome (Gh_A12G2172) of *Gossypium hirsutum* L. This sequence is from glanded (GL; GVS4) Stoneville 7A cotton. Promoter sequence; nucleotides 1-1949. 5'-UTR sequence; nucleotides 1950-2086. Coding sequence; nucleotides 2087-3514. 3'-UTR sequence; nucleotides 3515-3689. Terminator sequence; nucleotides 3690-3914. Promoter sequences have 2 SNPs: A in GL to C in gl at nucleotide 1113, G in GL to C in gl at nucleotide 1241. Coding sequences also have two SNPs: T in GL to C in gl at nucleotide 3304, A in GL to T in gl at nucleotide 3401.

SEQ ID NO:6—CGF3 gene sequence in A-Genome (Gh_A12G2172) of *Gossypium hirsutum* L. This sequence is from glandless (gl; GVS5) Stoneville 7A cotton. Promoter sequence; nucleotides 1-1949. 5'-UTR sequence; nucleotides 1950-2086. Coding sequence; 2087-2448, 7550-8615. 3'-UTR sequence; nucleotides 8616-8789. Terminator sequence; nucleotides 8790-9015. Transposon insert; nucleotides 2449-7549. Promoter sequences have 2 SNPs: A in GL to C in gl at nucleotide 1113, G in GL to C in gl at nucleotide 1241. Coding sequences also have two SNPs: T in GL to C in gl at nucleotide 8404 in gl, A in GL to T in gl at nucleotide 8500 in gl. Promoter sequence has two base pair deletion in the gl-TT deletion at nucleotides 1097-1098 in the gl.

SEQ ID NO:7-CGF3 gene sequence in D-Genome (Gh_D12G2351) of *Gossypium hirsutum* L. This sequence is from glanded (GL; GVS4) Stoneville 7A cotton. Promoter sequence; nucleotides 1-4263. 5'-UTR sequence; nucleotides 4264-4360. Coding sequence; nucleotides 4361-5788. 3'-UTR sequence; nucleotides 5789-6020. Terminator sequence; nucleotides 6021-6202. Promoter sequences have 15 SNPs: C in GL to A in gl at nucleotide 225 in GL, G in GL to A in gl at nucleotide 236 in GL, T in GL to C in gl at nucleotide 280 in GL, G in GL to T in gl at nucleotide 338 in GL, T in GL to C in gl at nucleotide 610 in GL, C in GL to T in gl at nucleotide 765 in GL, T in GL to C in gl at nucleotide 1581 in GL, C in GL to T in gl at nucleotide 1738 in GL, T in GL to C in gl at nucleotide 1961 in GL, C in GL to G in gl at nucleotide 1994 in GL, A in GL to C in gl at nucleotide 2202 in GL, A in GL to G in gl at nucleotide 2904 in GL, G in GL to T in gl at nucleotide 2921 in GL, A in GL to C in gl at nucleotide 2979 in GL, and G in GL to A in gl at nucleotide 3600 in GL. Coding sequences also have two SNPs: C in GL to A in gl at nucleotide 4979 in GL (CAC (His) to AAC (Asn)), C in GL to T in gl at nucleotide 5113 in GL [No amino acid change GTC (val) to GTT (val)].

SEQ ID NO:8-CGF3 gene sequence in D-Genome (Gh_D12G2351) of *Gossypium hirsutum* L. This sequence is from glandless (gl; GVS5) Stoneville 7A cotton. Promoter sequence; nucleotides 1-4217. 5'-UTR sequence; nucleotides 4218-4314. Coding sequence; nucleotides 4315-5742. 3'-UTR sequence; nucleotides 5743-5974. Terminator sequence; nucleotides 5974-6155. Promoter sequences have 15 SNPs: C in GL to A in gl at nucleotide 225 in GL, G in GL to A in gl at nucleotide 236 in GL, T in GL to C in gl at nucleotide 280 in GL, G in GL to T in gl at nucleotide 338 in GL, T in GL to C in gl at nucleotide 610 in GL, C in GL to T in gl at nucleotide 765 in GL, T in GL to C in gl at nucleotide 1581 in GL, C in GL to T in gl at nucleotide 1738 in GL, T in GL to C in gl at nucleotide 1961 in GL, C in GL to G in gl at nucleotide 1994 in GL, A in GL to C in gl at nucleotide 2202 in GL, A in GL to G in gl at nucleotide 2904 in GL, G in GL to T in gl at nucleotide 2921 in GL, A in GL to C in gl at nucleotide 2979 in GL, and G in GL to A in gl at nucleotide 3600 in GL, and 2 deletions in gl: a 1 nucleotide deletion at nucleotide 761, and a 49 nucleotide deletion at nucleotide 1424, and two insertions in gl: a 3 nucleotide insertion at nucleotide 430 and a 1 nucleotide insertion at nucleotide 1894. Coding sequences also have two SNPs: C in GL to A in gl at nucleotide 4979 in GL (CAC (His) to AAC (Asn)), C in GL to T in gl at nucleotide 5113 in GL [No amino acid change GTC (val) to GTT (val)]. Terminator sequences has one base pair deletion in the gl: G at nucleotide 6035 in GL deleted in the gl.

SEQ ID NOs:9-30—Primers used to amplify segment of the coding sequence of the target gene for cloning into TRV2 binary vector (Table 1).

SEQ ID NOs:31-42—Primers used to amplify and isolate CGF genes from both A and D genomes of GVS4 and GVS5 (Table 3).

SEQ ID NOs:43-54—Primers used to conduct qRT-PCR analyses on CGF1, CGF2 and CGF3 (Table 2).

SEQ ID NOs:55-90—Primers used to sequence CGF1, CGF2 and CGF3 genes (Table 4).

SEQ ID NOs:91-93—Primers used to amplify larger promoter fragments from CGF3 gene (Table 8).

SEQ ID NOs:94-98—sgRNA sequences for CGF2 and CGF3 genes (Table 9).

SEQ ID NOs:99-122—Primers used to amplify CGF2 and CGF3 genes (Table 10).

BRIEF DESCRIPTION OF THE DRAWINGS

The following drawings form part of the present specification and are included to further demonstrate certain aspects of the present disclosure. The present disclosure may be better understood by reference to one or more of these drawings in combination with the detailed description of specific embodiments presented herein.

FIG. 6A. ACGF3 in glanded (GVS4) cotton. FIG. 6B. ACGF3 in glandless (GVS5) cotton showing four SNPs (thin lines), one deletion (thick line) and a transposon insertion. The Copia-like, retrotransposon is 5.1 kb in size. Arrows at the end of the retrotransposon represent direct repeats. The long thin arrow indicates direction and size of an open reading frame. Functional domains are: 1: gag-polypeptide of LTR copia-type; 2: GAG-pre-integrase domain; 3: Integrase core domain; 4: Reverse transcriptase (RNA-dependent DNA polymerase); 5: Ty1/Copia family of RNaseHI in long-term repeat retroelements. FIG. 6C. DCGF3 in glanded (GVS4) cotton. FIG. 6D. DCGF3 in glandless (GVS5) cotton showing 17 SNPs (15 in the promoter and 2 in the CDS), three deletions (2 in the promoter, 1 in the terminator), and two insertions in the promoter.

DETAILED DESCRIPTION OF THE INVENTION

Figure 1:
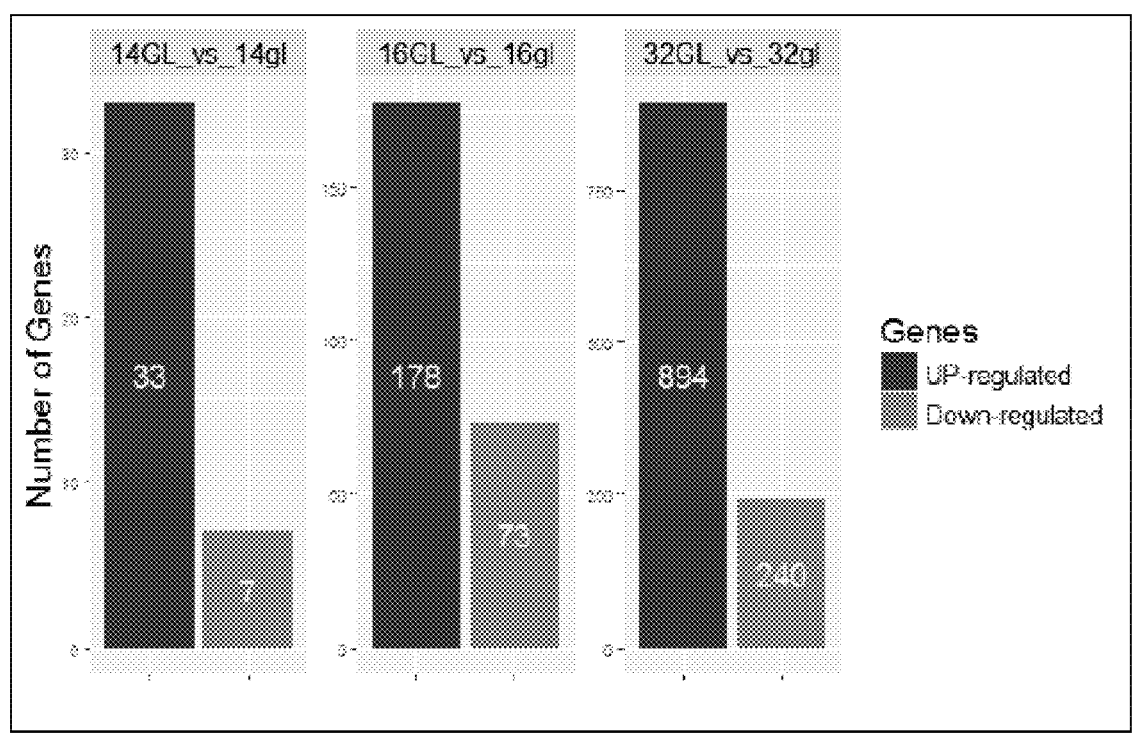
FIG. 1. Differentially expressed genes identified in pairwise comparisons between glanded (GL) and glandless (gl) embryos at 14, 16, and 32 day post-anthesis.

The present disclosure provides genes that are responsible for gland formation in cotton. An RNA-seq based approach was used to identify the genes that are responsible for gland formation. In seeds and other parts of cultivated, tetraploid cotton (*Gossypium hirsutum* L.), multicellular groups of cells lysigenously form dark glands containing toxic terpenoids such as gossypol that defend the plant against pests and pathogens. In the developing cotton embryo, gland formation occurs after 14 day-post-anthesis (dpa), therefore, 14, 16 and 32 dpa embryos from glanded (GL; GVS4) and glandless (gl; GVS5) cotton (Stoneville 7A; *Gossypium hirsutum*) were used to isolate RNA, which was used for RNA-seq analysis. Thirty three genes were identified that were downregulated in the glandless embryos at 14 dpa compared to the glanded embryos. Ten of these genes were selected to perform Virus (Tobacco Rattle Virus) Induced Gene Silencing (VIGS, a simple, yet powerful method to silence a target gene in young emerging leaves in a temporary manner) experiments on 12-day-old seedlings. Of the ten genes targeted in this manner, negative effects on gland formation were observed after silencing of three gene pairs, designated Cotton Gland Formation (CGF) genes.

The terpenoids are usually produced and stored in the glands, and the reduced levels of these compounds are most likely a result of lower gland numbers or lesser number of functional glands. Thus, based on the results from RNA-seq analysis and VIGS experiments, three genes (encoding transcription factors) have been identified that play a very important role in the formation of glands in the cotton plant. These CGF genes can be targeted, either individually or in combination, for silencing through RNAi, CRISPR interference (CRISPRi) or C2c2-mediated destruction of specific transcripts to eliminate the glands and thus gossypol from the cottonseed only. Tissue-specific silencing of a gene represents a powerful approach to examine the effects of silencing a gene in a particular tissue and the trait created by these methods is stable and heritable. The resulting plants from these modifications produce glandless seeds, while maintaining the wild-type level of glands/terpenoids in rest of the plant for protection against pests. In further aspects of the present disclosure, the use of leaf-specific or green tissue-specific promotors to overexpress the CGF1, CGF2 and/or CGF3 coding sequences leading to increased levels of glands/terpenoids in the leaves or flowers of the plant for even greater protection against pests and diseases.

Embodiments discussed in the context of methods and/or compositions of the present disclosure may be employed with respect to any other method or composition described herein. Thus, an embodiment pertaining to one method or composition may be applied to other methods and compositions of the present disclosure as well.

I. Nucleic Acids and Amino Acids

As used herein, the term "DNA" or "DNA molecule" refers to a double-stranded DNA molecule of genomic or synthetic origin, i.e., a polymer of deoxyribonucleotide bases or a polynucleotide molecule, read from the 5' (upstream) end to the 3' (downstream) end. As used herein, the term "DNA sequence" refers to the nucleotide sequence of a DNA molecule.

As used herein, the term "isolated DNA molecule" refers to a DNA molecule at least partially separated from other molecules normally associated with it in its native or natural state. In one embodiment, the term "isolated" refers to a DNA molecule that is at least partially separated from some of the nucleic acids which normally flank the DNA molecule in its native or natural state. Thus, DNA molecules fused to regulatory or coding sequences with which they are not normally associated, for example as the result of recombinant techniques, are considered isolated herein. Such molecules are considered isolated when integrated into the chromosome of a host cell or present in a nucleic acid solution with other DNA molecules, in that they are not in their native state.

As used herein, the term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an RNA molecule or internally, for example in one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

As used herein, the phrase "double stranded RNA" refers to an RNA molecule at least a part of which is in Watson-Crick base pairing forming a duplex. As such, the term is to be understood to encompass an RNA molecule that is either fully or only partially double stranded. Exemplary double stranded RNAs include, but are not limited to molecules comprising at least two distinct RNA strands that are either partially or fully duplexed by intermolecular hybridization. Additionally, the term is intended to include a single RNA molecule that by intramolecular hybridization can form a double stranded region (for example, a hairpin). Thus, as used herein the phrases "intermolecular hybridization" and "intramolecular hybridization" refer to double stranded molecules for which the nucleotides involved in the duplex formation are present on different molecules or the same molecule, respectively.

In certain embodiments of the present disclosure, nucleic acids and polypeptides are used that have at least about 80% (percent) sequence identity, about 85% sequence identity, about 90% sequence identity, about 91% sequence identity, about 92% sequence identity, about 93% sequence identity, about 94% sequence identity, about 95% sequence identity, about 96% sequence identity, about 97% sequence identity, about 98% sequence identity, and about 99% sequence identity to the CGF1, CGF2 and CGF3 nucleic acids, or protein sequences encoded by these nucleic acid sequences, as described herein. As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Methods to determine "percent sequence identity" are codified in numerous publicly available programs including, but are not limited to, GCG (also known as The Wisconsin Package™), and the BLAST programs that are publicly available from NCBI. Optimal alignment of sequences for aligning a comparison window are well known to those skilled in the art and may be conducted by tools including, but not limited to, the local homology algorithm of Smith and Waterman (*Adv. Appl. Math.* 2:482-489, 1981), the homology alignment algorithm of Needleman and Wunsch (*J. Mol. Biol.* 48:443-453, 1970), and the search for similarity method of Lipman and Pearson (*Science* 227:1435-1441, 1985).

As used herein, the term "gene" refers to a nucleic acid sequence that encodes an RNA, for example, nucleic acid sequences including, but not limited to, structural genes encoding a polypeptide. The term "gene" also refers broadly to any segment of DNA associated with a biological function. As such, the term "gene" encompasses sequences including but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation from one or more existing sequences.

As is understood in the art, a gene typically comprises a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

As used herein, the terms "polypeptide," "protein," and "peptide," which are used interchangeably herein, refer to a polymer of 20 or more amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted. As used herein, the terms "protein," "polypeptide," and "peptide" are used interchangeably herein when referring to a gene product. The term "polypeptide" encompasses proteins of all functions, including enzymes. Thus, exemplary polypeptides include gene products, naturally occurring proteins, homologs, orthologs, paralogs, fragments, and other equivalents, variants and analogs of the foregoing.

The term "fragment," when used in reference to a reference nucleic acid or polypeptide, refers to a nucleic acid or polypeptide in which nucleotides or amino acid residues are deleted as compared to the reference nucleic acid or polypeptide itself, but where the remaining nucleotide or amino acid sequence is usually identical to the corresponding positions in the reference nucleic acid or polypeptide. Such deletions can occur at the 3' or 5' end of the reference nucleic acid, or both, or at the amino-terminus or carboxy-terminus, or both, of the reference polypeptide. The length of the nucleic acid fragments are typically dependent on the function for which such fragments will be used. For example, when such fragments are to be used as PCR primers or probes, the nucleic acid fragments are typically at least about 12 to about 15 contiguous nucleotides in length, although in certain embodiments of the present disclosure the nucleotide fragments can be about 20, about 25, about 30, about 35, about 40, about 45 or about 50 contiguous nucleotides in length, or more. The term "oligonucleotide" typically refers to such short nucleic acid fragments, usually less than about 100 nucleotides in length.

A "primer" is typically a highly purified, isolated polynucleotide that is designed for use in specific annealing or hybridization methods that involve thermal amplification. A pair of primers may be used with template DNA, such as a sample of cotton genomic DNA, in a thermal amplification, such as polymerase chain reaction (PCR), to produce an amplicon, where the amplicon produced from such reaction would have a DNA sequence corresponding to sequence of the template DNA located between the two sites where the primers hybridized to the template. As used herein, an "amplicon" is a piece or fragment of DNA that has been synthesized using amplification techniques. A "probe" is an isolated nucleic acid that is complementary to a strand of a target nucleic acid. Probes according to the present disclosure include not only deoxyribonucleic or ribonucleic acids but also polyamides and other probe materials that bind specifically to a target DNA sequence and the detection of such binding can be useful in diagnosing, discriminating, determining, or confirming the presence of that target DNA sequence in a particular sample. A probe may be attached to a conventional detectable label or reporter molecule, e.g., a radioactive isotope, ligand, chemiluminescent agent, or enzyme. Probes and primers according to the present disclosure may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed.

When nucleic acid fragments are to be used to express part or all of an encoded protein sequence, the nucleic acid fragments are typically about 100, 250, 500, 750, 1000, 1500, 2000 or more contiguous nucleotides in length. Likewise, polypeptide fragments typically are at least about 5, about 6, about 7, about 8, about 9 or about 10 amino acids long, at least about 15 amino acids long, at least about 20, about 30, about 40, or about 50 amino acids long, at least about 75 amino acids long, or at least about 100, about 150, about 200, about 300, about 500, or more amino acids long. A nucleic acid or polypeptide fragment can retain one or more of the biological activities of the reference nucleic acid or polypeptide. Further, fragments can include a sub-fragment of a specific region, which sub-fragment retains a function of the region from which it is derived.

II. Plant Transformation Constructs

In certain aspects, the disclosure provides vectors for plant transformation and/or expression. Vectors used for plant transformation may include, for example, plasmids, cosmids, YACs (yeast artificial chromosomes), BACs (bacterial artificial chromosomes), or any other suitable cloning system, as well as fragments of DNA therefrom. Thus when the term "vector" or "expression vector" is used, all of the foregoing types of vectors, as well as nucleic acid sequences isolated therefrom, are included. Vectors may be used to express or overexpress a gene coding sequence such as an CGF1, CGF2 and/or CGF3 coding sequence or an RNA sequence such as sequence complementary to all or part of an CGF1, CGF2 and/or CGF3 gene sequence.

As used herein, the term "operably linked" refers to a first molecule joined to a second molecule, wherein the molecules are so arranged that the first molecule affects the function of the second molecule. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. A leader, for example, is operably linked to coding sequence when it is capable of serving as a leader for the polypeptide encoded by the coding sequence.

It is contemplated that utilization of cloning systems with large insert capacities will allow introduction of large DNA sequences comprising more than one selected gene. In accordance with the present disclosure, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for *Agrobacterium*-mediated transformation was disclosed by Hamilton, et al. (*Proc. Natl. Acad. Sci. USA* 93:9975-9979, 1996).

Particularly useful for transformation are expression cassettes that have been isolated from such vectors. DNA segments used for transforming plant cells will, of course, generally comprise the cDNA, gene, or genes which one desires to introduce into and have expressed in the host cells. These DNA segments can further include structures such as promoters, enhancers, polylinkers, or even regulatory genes as desired. The DNA segment or gene chosen for cellular introduction will often encode a protein that will be expressed in the resultant recombinant cells resulting in a screenable or selectable trait and/or which will impart an improved phenotype to the resulting transgenic plant. However, this may not always be the case, and the present disclosure also encompasses transgenic plants incorporating non-expressed transgenes. Preferred components likely to be included with vectors used in the current disclosure are as follows.

A. Regulatory Elements

Exemplary promoters for expression of a nucleic acid sequence include plant promoters such as the CaMV 35S promoter (Odell, et al., *Nature* 313:810-812, 1985), or others such as CaMV 19S (Lawton, et al., *Plant Mol. Biol.* 9:315-324, 1987), nos (Ebert, et al., *Proc. Natl. Acad. Sci. USA* 84:5745-5749, 1987), Adh (Walker, et al., *Proc. Natl. Acad. Sci. USA* 84:6624-6628, 1987), sucrose synthase (Yang and Russell, *Proc. Natl. Acad. Sci. USA* 87:4144-4148, 1990), a-tubulin, actin (Wang, et al., *Mol. Cell. Biol.* 12:3399-3406, 1992), cab (Sullivan, et al., *Mol. Gen. Genet.* 215:431-40, 1989), PEPCase (Hudspeth and Grula, *Plant Mol. Biol.* 12:579-589, 1989), RUBISCO, or those associated with the R gene complex (Chandler, et al., *Plant Cell.* 1:1175-1183, 1989). Tissue-specific promoters such as seed-specific promoters (Sunilkumar, et al., *Transgenic Res.* 11:347-359, 2002; U.S. Pat. No. 7,626,081, the entire disclosure of which is specifically incorporated herein by reference), root cell promoters (Conkling, et al., *Plant Physiol.* 93:1203-1211, 1990) and tissue-specific enhancers are also contemplated to be useful, as are inducible promoters such as ABA- and turgor-inducible promoters. The PAL2 promoter may also be useful with the present disclosure (U.S. Patent Application Publication No. 2004/0049802, the entire disclosure of which is specifically incorporated herein by reference).

Certain embodiments of the present disclosure involve overexpression of a CGF1, CGF2 and/or a CGF3 coding sequence in particular tissues of a cotton plant, for example using leaf-specific or green tissue-specific promoters to overexpress a CGF1, CGF2 and/or a CGF3 coding sequence in the leaves of the cotton plant. This leads to increased number of glands in the leaves, which provides increased amounts of gossypol, and thereby extra protection against pests and diseases.

The DNA sequence between the transcription initiation site and the start of the coding sequence, i.e., the untranslated leader sequence, can also influence gene expression. One may thus wish to employ a particular leader sequence with a transformation construct of the present disclosure. Preferred leader sequences are contemplated to include those that comprise sequences predicted to direct optimum expression of the attached gene, i.e., to include a preferred consensus leader sequence that may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is contemplated that vectors for use in accordance with the present disclosure may be constructed to include an ocs enhancer element. This element was first identified as a 16-bp palindromic enhancer from the octopine synthase (ocs) gene of *Agrobacterium* (Ellis, et al., *EMBO J.* 6:3203-3208, 1987), and is present in at least 10 other promoters (Bouchez, et al., *EMBO J.* 8:4197-4204, 1989). The use of an enhancer element, such as the ocs element and particularly multiple copies of the element, may act to increase the level of transcription from adjacent promoters when applied in the context of plant transformation.

It is envisioned that CGF1, CGF2 and/or CGF3 coding sequences may be introduced under the control of novel promoters or enhancers, etc., or homologous or tissue-specific promoters or control elements. Vectors for use in tissue-specific targeting of genes in transgenic plants will typically include tissue-specific promoters and may also include other tissue-specific control elements such as enhancer sequences. Promoters that direct specific or enhanced expression in certain plant tissues will be known to those of skill in the art in light of the present disclosure. These include, for example, the rbcS promoter, specific for green tissue; the ocs, nos, and mas promoters, which have higher activity in roots or wounded leaf tissue.

In some embodiments of the presently disclosed subject matter, the presently disclosed sequences are expressed in a seed-specific fashion in a cotton plant. Seed-specific promoters can include those promoters associated with genes involved with the production of seed storage proteins, which typically are expressed at high levels during seed development and for which expression is tightly controlled both spatially and temporally in the developing seed.

As such, regulatory sequences from genes encoding seed storage proteins can represent a valuable source of promoters that can be utilized to drive the expression of transgenes in a seed-specific manner. The promoters from the cotton α-globulin gene B (Sunilkumar, et al., *Transgenic Res.* 11:347-359, 2002; U.S. Pat. No. 7,626,081) soybean β-conglycinin genes, the French bean phaseolin gene, the sunflower helianthinin gene, and the carrot Dc3 promoter are examples of some of the well-characterized seed-specific promoters from dicots (see U.S. Patent Application Publication No. 2003/0154516 and references cited therein, the entire disclosures of which are incorporated by reference herein). Additional promoters that have been shown to be seed-specific in cotton include the soybean (*Glycine max*) lectin promoter described in Townsend and Llewellyn, *Funct. Plant Biol.* 29:835-843, 2002, and the Gh-sp promoter that was derived from a seed protein gene and is described in Song, et al., *J. Cotton Sci.* 4:217-223, 2000.

In some embodiments, a seed-specific promoter comprises a promoter from the cotton seed-specific α-globulin gene B. The 5' regulatory region of this gene, or subsequences thereof, when operably linked to either the coding sequence of a transgene comprising a CGF1, CGF2 and/or CGF3 sequence, direct expression of the CGF1, CGF2 and/or CGF3 sequence in a plant seed. Sequences that can direct seed-specific transgene expression include SEQ ID NOs:1-3 of PCT International Patent Application Publication No. WO 2003/052111, the entire disclosure of which is incorporated herein by reference.

B. Terminators

Transformation constructs prepared in accordance with the present disclosure will typically include a 3' end DNA sequence that acts as a signal to terminate transcription and allow for the poly-adenylation of the mRNA produced by coding sequences operably linked to a promoter. In one embodiment of the disclosure, the native terminator of a CGF1, CGF2 and/or CGF3 coding sequence is used. Alternatively, a heterologous 3' end may enhance the expression of sense or antisense CGF1, CGF2 and/or CGF3 coding sequences. Examples of terminators that may be useful in this context include those from the nopaline synthase gene of *Agrobacterium tumefaciens* (nos 3' end) (Bevan, et al., *Nucleic Acids Res.* 11:369-385, 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis, et al., *Genes Dev.* 1:1183-1200, 1987), sucrose synthase intron (Vasil, et al., *Plant Physiol.* 91:1575-1579, 1989) or TMV omega element (Gallie and Kado, *Proc. Natl. Acad. Sci. USA* 86:129-132, 1989), may further be included where desired.

C. Transit or Signal Peptides

Sequences that are joined to the coding sequence of an expressed gene, which are removed post-translationally from the initial translation product, and that facilitate the transport of the protein into or through intracellular or extracellular membranes, are termed transit (usually into vacuoles, vesicles, plastids, and other intracellular organelles) and signal sequences (usually to the endoplasmic reticulum, Golgi apparatus, and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Many examples of suitable marker proteins are known to the art and can be employed in the practice of the present disclosure.

Included within the terms "selectable" or "screenable" markers also are genes which encode a "secretable marker" whose secretion can be detected as a means of identifying or selecting for transformed cells. Examples include markers that are secretable antigens that can be identified by antibody interaction, or even secretable enzymes that can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase), and proteins that are inserted or trapped in the cell wall (e.g., proteins that include a leader sequence such as that found in the expression unit of extensin or tobacco PR-S).

Many selectable marker coding regions are known and could be used with the present disclosure including, but not limited to, neo (also called nptII) (Potrykus, et al., *Mol. Gen. Genet.* 199:169-177, 1985), which provides kanamycin resistance and can be selected for using kanamycin, G418, paromomycin, etc.; bar, which confers bialaphos or phosphinothricin resistance; an EPSP synthase protein (Jordan and McHughen, *Plant Cell Rep.* 7:281-284, 1988) or mutant EPSP synthase protein, which confer glyphosate resistance; a nitrilase such as bxn from *Klebsiella ozaenae* which confers resistance to bromoxynil (Stalker, et al., *Science* 242:419-423, 1988); a mutant acetolactate synthase (ALS) which confers resistance to imidazolinone, sulfonylurea, or other ALS inhibiting chemicals (European Patent Application No. 154, 204, 1985); a methotrexate resistant DHFR (Thillet, et al., *J. Biol. Chem.* 263:12500-12508, 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues; a β-lactamase gene (Sutcliffe, *Proc. Natl. Acad. Sci. USA* 75:3737-3741, 1978), which encodes an enzyme for which various chromogenic substrates are known (e.g., PADAC, a chromogenic cephalosporin); a xylE gene (Zukowski, et al., *Proc. Natl. Acad. Sci. USA* 80:1101-1105, 1983), which encodes a catechol dioxygenase that can convert chromogenic catechols; an α-amylase gene (Ikuta, et al., *Biotechnology* 8:241-242, 1990); a tyrosinase gene (Katz, et al., *J. Gen. Microbiol.* 129:2703-2714, 1983), which encodes an enzyme capable of oxidizing tyrosine to DOPA and dopaquinone, which in turn condenses to form the easily-detectable compound melanin; a β-galactosidase gene, which encodes an enzyme for which there are chromogenic substrates; a luciferase (lux) gene (Ow, et al., *Science* 234:856-859, 1986), which allows for bioluminescence detection; an aequorin gene (Prasher, et al., *Biochem. Biophys. Res. Commun.* 126:1259-1268, 1985), which may be employed in calcium-sensitive bioluminescence detection; or a gene encoding for green fluorescent protein (GFP) (WO 97/41228). Expression of GFP may be visualized in a cell or plant as fluorescence following illumination by particular wavelengths of light.

III. Antisense and RNAi Constructs

Antisense and RNAi treatments represent one way of inhibiting gland formation in accordance with the present disclosure (e.g., by down-regulation of CGF1, and in certain embodiments CGF2 and/or CGF3, gene expression). In particular, constructs comprising a CGF1, CGF2 and/or a CGF3 coding sequence, including fragments thereof, in antisense orientation, or combinations of sense and antisense orientation, may be used to decrease or effectively eliminate the expression of a CGF1, CGF2 and/or a CGF3 gene in a cotton plant and obtain reduction in gland formation in cotton seeds, and thereby reduction in gossypol levels in cotton seeds, as is described herein. Accordingly, this may be used to "knock-out" or "knock-down" the function of a CGF1, CGF2 and/or a CGF3 coding sequence or homologous sequences thereof.

Techniques for RNAi are well-known in the art. The technique is based on the fact that double-stranded RNA is capable of directing the degradation of messenger RNA with sequence complementary to one or the other strand (Fire, et al., *Nature* 391:806-811, 1998). Therefore, by expression of a particular coding sequence in sense and antisense orientation, either as a fragment or longer portion of the corresponding coding sequence, the expression of that coding sequence can be down-regulated.

Antisense, and in some aspects RNAi, methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense oligonucleotides, when introduced into a target cell, specifically bind to their target polynucleotide and interfere with transcription, RNA processing, transport, translation and/or stability. Antisense and RNAi constructs, or DNA encoding such RNA's, may be employed to inhibit gene transcription or translation, or both, within a host cell, either in vitro or in vivo, such as within a host plant cell. In certain embodiments of the disclosure, such an oligonucleotide may comprise any unique portion of a CGF1, CGF2 and/or a CGF3 nucleic acid sequence provided herein. In certain embodiments of the disclosure, such a sequence comprises at least 18, 30, 50, 75, or 100 or more contiguous nucleic acids of the CGF1, CGF2 and/or a CGF3 nucleic acid sequence, and/or complements thereof, which may be in sense and/or antisense orientation. By including sequences in both sense and antisense orientation, increased suppression of the corresponding CGF1, CGF2 and/or a CGF3 coding sequence may be achieved.

Constructs may be designed that are complementary to all or part of the promoter and other control regions, exons, introns, or even exon-intron boundaries of a gene. It is contemplated that the most effective constructs may include regions complementary to intron/exon splice junctions. Thus, it is proposed that a preferred embodiment includes a construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences that are completely complementary will be sequences that are entirely complementary throughout their entire length and have no base mismatches. Other sequences with lower degrees of homology also are contemplated. For example, an RNAi or antisense construct that has limited regions of high homology, but also contains a non-homologous region (e.g., ribozyme; see above) could be designed. Methods for selection and design of sequences that generate RNAi are well known in the art. These molecules, though having less than 50% homology, bind to target sequences under appropriate conditions.

It may be advantageous to combine portions of genomic DNA with cDNA or synthetic sequences to generate specific constructs. For example, where an intron is desired in the ultimate construct, a genomic clone can be used. The cDNA or a synthesized polynucleotide may provide more convenient restriction sites for the remaining portion of the construct and, therefore, would be used for the rest of the sequence. Constructs useful for generating RNAi may also comprise concatemers of sub-sequences that display gene regulating activity.

IV. Genome Modification and Control of Gene Expression

Many desirable traits can be introduced directly into a plant by the use of molecular techniques. One aspect of the disclosure includes cotton plants with a genome that has been changed by any method using site-specific genome modification techniques. Techniques of site-specific genome modification include the use of enzymes such as endonucleases, recombinases, transposases, helicases and any combination thereof. In one aspect, an endonuclease is selected from a meganuclease, a zinc-finger nuclease (ZFN), a transcription activator-like effector nucleases (TALEN), an Argonaute, and an RNA-guided nuclease, such as a CRISPR associated nuclease.

In another aspect, the endonuclease is a dCas9-recombinase fusion protein. As used herein, a "dCas9" refers to a Cas9 endonuclease protein with one or more amino acid mutations that result in a Cas9 protein without endonuclease activity, but retaining RNA-guided site-specific DNA binding. As used herein, a "dCas9-recombinase fusion protein" is a dCas9 with a protein fused to the dCas9 in such a manner that the recombinase is catalytically active on the DNA.

Non-limiting examples of recombinase include a tyrosine recombinase attached to a DNA recognition motif provided herein is selected from the group consisting of a Cre recombinase, a Gin recombinase a Flp recombinase, and a Tnp 1 recombinase. In an aspect, a Cre recombinase or a Gin recombinase provided herein is tethered to a zinc-finger DNA-binding domain, or a TALE DNA-binding domain, or a Cas9 nuclease. In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

Site-specific genome modification enzymes, induce a genome modification such as a double-stranded DNA break (DSB) or single-strand DNA break at the target site of a genomic sequence that is then repaired by the natural processes of homologous recombination (HR) or non-homologous end-joining (NHEJ). Sequence modifications then occur at the cleaved sites, which can include deletions or insertions that result in gene disruption in the case of NHEJ, or integration of exogenous sequences by homologous recombination.

In addition to genome modification, targeted silencing of transcription can also be used in certain embodiments of the present disclosure. One example of such targeted silencing is termed CRISPR interference (CRISPRi), wherein expression of a catalytically inactive Cas9 protein (or dCas9) and a single guide RNA (sgRNA) designed to bind to a target transcript in a cell results in a block of transcript elongation, resulting in repression of the target gene (Qi, et al., *Cell* 152:1173-1183, 2013; Larson, et al., *Nat. Protoc.* 8:2180-2196, 2013). Another example of targeted silencing utilizes the Class 2 type VI-A CRISPR-Cas effector C2c2 RNase function, which is guided by a single crRNA that can be designed to bind to a target transcript (ssRNA), leading to cleavage of the target transcript and repression of the target gene (Abudayyeh, et al., *Science* 353:aaf5573. doi: 10.1126/science.aaf5573, 2016).

V. Methods for Genetic Transformation

Suitable methods for transformation of plant or other cells for use with the current disclosure are well-known to the person of skill in the art, and are believed to include virtually any method by which DNA can be introduced into a cell, such as by direct delivery of DNA such as by PEG-mediated transformation of protoplasts, by desiccation/inhibition-mediated DNA uptake, by electroporation (U.S. Pat. No. 5,384,253, specifically incorporated herein by reference in its entirety), by agitation with silicon carbide fibers (U.S. Pat. No. 5,302,523, specifically incorporated herein by reference in its entirety; and U.S. Pat. No. 5,464,765, specifically incorporated herein by reference in its entirety), by *Agrobacterium*-mediated transformation (U.S. Pat. Nos. 5,591,616 and 5,563,055; both specifically incorporated herein by reference) and by acceleration of DNA coated particles (U.S. Pat. Nos. 5,550,318; 5,538,877; and 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described in U.S. Pat. No. 5,563,055, specifically incorporated herein by reference in its entirety. *Agrobacterium*-mediated transformation is most efficient in dicotyledonous plants, such as cotton, and is the preferable method for transformation of dicots.

Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. Current vectors have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus, or alternatively, one may transform immature embryos or other organized tissue directly. In this technique, one partially degrades the cell walls of the chosen cells by exposing them to pectin-degrading enzymes (pectolyases) or mechanically wounding in a controlled manner. One also may employ protoplasts for electroporation transformation of plants.

C. Microprojectile Bombardment

Another method for delivering transforming DNA segments to plant cells in accordance with the present disclosure is microprojectile bombardment (U.S. Pat. Nos. 5,550,318; 5,538,880; 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species that have been transformed by microprojectile bombardment include cotton (Finer and McMullen, *Plant Cell Rep.* 8:586-589, 1990).

D. Other Transformation Methods

Transformation of protoplasts can be achieved using methods based on calcium phosphate precipitation, polyethylene glycol treatment, electroporation, and combinations of these treatments. Application of these systems to different plant strains depends upon the ability to regenerate that particular plant species/genotype from protoplasts.

To transform plant species/genotypes that cannot be successfully regenerated from protoplasts, other ways to introduce DNA into intact cells or tissues can be utilized. For example, silicon carbide fiber-mediated transformation may be used with or without protoplasting (U.S. Pat. No. 5,563,055, specifically incorporated herein by reference in its entirety). Transformation with this technique is accomplished by agitating silicon carbide fibers together with cells in a DNA solution. DNA passively enters as the cells are punctured.

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. BACTOAGAR, GELRITE, and GELGRO, among others, are specific types of solid support that are suitable for growth of plant cells in tissue culture.

Some cell types will grow and divide either in liquid suspension or on solid media. Plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos, and gametic cells such as microspores, pollen, sperm, and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells that may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques that may be employed to select target cells include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators, and vitamins. Most of the media employed in the practice of the present disclosure will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described, and are well-known to the person of skill in the art. Examples of these media include, but are not limited to, N6 medium and MS media.

VI. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the present disclosure. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes, one may employ a means for selecting those cells that are stably transformed. One exemplary embodiment of such a method is to introduce into the host cell a marker gene that confers resistance to some normally inhibitory agent, such as an antibiotic or herbicide. Examples of antibiotics that may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide that constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism. Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT), which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*. In the bacterial source organism, this enzyme acetylates the free amino group of PPT preventing auto-toxicity. The bar gene has been cloned and expressed in a variety of plants.

Another example of a herbicide that is useful for selection of transformed cell lines in the practice of the present disclosure is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103.

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker that may be used in a similar fashion is the gene coding for green fluorescent protein.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D, picloram, kinetin, BAP, 2iP or zeatin, either individually or in any combination. Media improvement in these and similar ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 weeks, then transferred to media conducive to initiation and maturation of embryoids. Cultures are transferred every 2 weeks on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 weeks to 10 months after a transformant is identified, depending on the species and initial tissue. During regeneration, cells are grown on solid media in tissue culture vessels. Illustrative embodiments of such vessels are Petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 week on media containing the above ingredients along with $10^{-5}$ M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and northern blotting and PCR™; "biochemical" assays, such as detecting the presence of a protein product, e.g., by immunological means (ELISAs and western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note that intact sequences will not always be present, presumably due to rearrangement or deletion of sequences in the cell. The presence of DNA elements introduced through the methods of this disclosure may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques, it would be possible to clone fragments of the host genomic DNA adjacent to an introduced gene.

Positive proof of DNA integration into the host genome and the independent identities of transformants may be determined using the technique of Southern hybridization. Using this technique, specific DNA sequences that were introduced into the host genome and flanking host DNA sequences can be identified. Hence the Southern hybridization pattern of a given transformant serves as an identifying characteristic of that transformant. In addition, it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization, which are modifications of Southern hybridization techniques, one could obtain the same information that is derived from PCR™, e.g., the presence of a gene.

Both PCR™ and Southern hybridization techniques can be used to demonstrate transmission of a transgene to progeny. In most instances, the characteristic Southern hybridization pattern for a given transformant will segregate in progeny as one or more Mendelian genes, indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™, it is first necessary to reverse-transcribe RNA into DNA, using enzymes such as reverse transcriptase, and then amplify the DNA through the use of conventional PCR™ techniques. In most instances, PCR™ techniques, while useful, will not demonstrate integrity of the RNA product. Further information about the nature of the RNA product may be obtained by northern blotting. This technique will demonstrate the presence of an RNA species and give information about the integrity of that RNA. The presence or absence of an RNA species also can be determined using dot or slot blot northern hybridizations. These techniques are modifications of northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression. In addition, silencing of CGF1, CGF2 and/or a CGF3 gene expression can be evaluated by Northern blots for the target gene, for the siRNA (target gene) or qRT-PCR. However, as above, confirmation of gene silencing relies on evaluation of the phenotypic changes brought about by silencing of gene expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting, in which antibodies are used to locate individual gene products that have been separated by electrophoretic techniques. Additional techniques may be employed to absolutely confirm the identity of the product of interest, such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently, the expression of a gene product is determined by evaluating the phenotypic results of its expression. These assays also may take many forms including, but not limited to, analyzing changes in the chemical composition, morphology, or physiological properties of the plant. Chemical composition may be altered by expression of genes encoding enzymes or storage proteins that change amino acid composition and may be detected by amino acid analysis, or by enzymes that change starch quantity that may be analyzed by near infrared reflectance spectrometry. Morphological changes may include greater stature or thicker stalks. Most often changes in response of plants or plant parts to imposed treatments are evaluated under carefully controlled conditions termed bioassays.

VII. Breeding Plants of the Present Disclosure

In addition to direct transformation of a particular plant genotype with a construct prepared according to the current disclosure, transgenic plants may be made by crossing a plant having a selected DNA of the present disclosure to a second plant lacking the construct. For example, a selected CGF1, CGF2 and/or CGF3 coding sequence, or mutated form thereof, can be introduced into a particular plant variety by crossing, without the need for ever directly transforming a plant of that given variety. Therefore, the current disclosure not only encompasses a plant directly transformed or regenerated from cells that have been transformed in accordance with the current disclosure, but also the progeny of such plants.

As used herein the term "progeny" denotes the offspring of any generation of a parent plant prepared in accordance with the instant disclosure, wherein the progeny comprises a selected DNA construct. "Crossing" a plant to provide a plant line having one or more added transgenes relative to a starting plant line, as disclosed herein, is defined as the techniques that result in a transgene of the disclosure being introduced into a plant line by crossing a starting line with a donor plant line that comprises a transgene of the disclosure. To achieve this, one could, for example, perform the following steps:

(a) plant seeds of the first (starting line) and second (donor plant line that comprises a transgene of the present disclosure) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VIII. Definitions

Artificially down-regulated: A gene may be referred to as artificially down-regulated if the normal or natural expression level of the gene is reduced as a result of a non-natural occurrence, such as by RNA-interference, CRISPR or C2c2-mediated transcript destruction, induced mutation or genetic modification.

Down-regulated: As used herein, down-regulation of a gene refers to a reduction in its expression, whether by natural means or as a result of genetic modification.

Expression: The combination of intracellular processes, including transcription and translation achieved by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence that is not normally present in a given host genome in the genetic context in which the sequence is currently found. In this respect, the sequence may be native to the host genome but be rearranged with respect to other genetic sequences within the host sequence. For example, a regulatory sequence may be heterologous in that it is linked to a different coding sequence relative to the native regulatory sequence.

Normal expression: As used herein, "normal expression" is the level of expression of a gene such as FPGS1 that is measured in a non-transgenic or wild-type plant.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an T0 transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

T0 transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule that is designed for introduction into a host genome by genetic transformation. In certain embodiments of the instant disclosure, transformation constructs will comprise all of the genetic elements necessary to direct the expression of one or more exogenous genes. In particular embodiments of the instant disclosure, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation that was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences that are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors are capable of replication in a host cell. A plasmid is an exemplary vector, as are expression cassettes isolated therefrom.

As used herein the terms "encode" or "encoding" with reference to a nucleic acid are used to make the disclosure readily understandable by the skilled artisan, however these terms may be used interchangeably with "comprise" or "comprising" respectively.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects. As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

Other objects, features and advantages of the present disclosure will become apparent from the following detailed description. It should be understood, however, that the detailed description and the specific examples, while indicating preferred embodiments of the present disclosure, are given by way of illustration only, since various changes and modifications within the spirit and scope of the present disclosure will become apparent to those skilled in the art from this detailed description.

EXAMPLES

The following examples are included to demonstrate preferred embodiments of the present disclosure. It should be appreciated by those of skill in the art that the techniques disclosed in the examples which follow represent techniques discovered by the inventor to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Example 1

Plant Materials and Embryo Isolation

Near-isogenic lines of tetraploid cotton (*Gossypium hirsutum* L.) cultivar Stoneville 7A, designated Stoneville 7A glanded (STV GL; GVS4; G12G12 G13G13) and Stoneville 7A glandless (STV gl; GVS5; $gl_2gl_2gl_3gl_3$) (Scheffler and Romano, *J. Plant Regist.* 6:190-194, 2012) were used for comparative RNA-seq analysis to identify the genes that are involved in gland formation. A glanded cultivar, Coker 312, was used to conduct VIGS experiments, CRISPR-Cas9 experiments, and CGF3 overexpression studies to validate the function of the candidate genes.

Example 2

Embryo Isolation

Fully opened flowers were tagged on the greenhouse grown plants of GVS4 and GVS5. Bolls at 14, 16, 32 days post-anthesis (dpa) were collected and embryos were carefully dissected from the developing seeds under a stereo microscope.

Example 3

RNA Isolation

Total RNA was extracted from three independent biological replicates of each embryo sample using the Spectrum Plant Total RNA Kit (Sigma-Aldrich) following manufacturer's instructions. After on-column, DNase I treatment to remove the DNA from samples, RNA was eluted with nuclease-free water. RNA quantity was measured using micro spectrophotometer (Nano-Drop Technologies, Inc.), and quality was assessed with Agilent 2100 Bioanalyzer (Agilent Technologies, Inc.). Only the samples with RNA integrity number (RIN) above 8.0 were used for the analysis.

Example 4

Library Preparation and RNA-Sequencing

Library preparation and RNA-seq was performed by Texas A&M AgriLife Genomics and Bioinformatics Services. Poly-A enriched mRNA from each replicate sample was used for the library preparation, 125-bp paired-end sequencing was performed using Illumina HiSeq 2500. Sequence cluster identification, quality pre-filtering, base calling and uncertainty assessment were done in real time using Illumina HCS 2.2.58 and RTA 1.18.64 software with default parameter settings.

Example 5

Bioinformatics Analysis

RNA-seq data was further processed using Trimmomatic software to filter out the low-quality reads (Bolger, et al., *Bioinformatics* 30:2114-2120, 2014) using LEADING:20 TRAILING:20 SLIDINGWINDOW:5:20 MINLEN:100 as parameters. Filtered reads were then aligned to the *G. hirsutum* (Texas Marker-1) reference genome (Zhang, et al., *Nat. Biotech.* 33:531-537, 2015) using HISAT2 program (Kim, et al., *Nat. Meth.* 12:357-360, 2015) and gene annotation in GFF3 format (NBI_*Gossypium*_hirsutum_v1.1.gene.gff3) (Yu et al., *Nucl. Acids Res.* 42:D1229-D1236, 2014). The allotetraploid cotton *G. hirsutum* L. acc. Texas Marker-1 (TM-1) is widely used as a genetic standard and its genome was sequenced in 2015. The output from the Hisat2 program was then analyzed to quantify the reads per gene using the HTSeq-count program (Anders, et al., *Bioinformatics* 31:166-169, 2015). Only the known mRNA sequences were quantified. The differentially expressed genes were identified using DESeq2 (Love, et al., *Genome Biol.* 15:550, 2014). The False Discovery Rate was set to ≤0.05 and the log fold change value to ≥2 to determine differentially expressed genes.

Example 6

Virus Induced Gene Silencing (VIGS)

VIGS vector construction and infiltration were performed as described (Dinesh-Kumar, et al., Virus-Induced Gene Silencing. In: Grotewold E (ed) Plant Functional Genomics. Humana Press, Totowa, N.J., pp 287-293, 2003; Gao and Shan, *Methods Mol. Biol.* 975:157-165, 2013) with slight modifications. A segment of the coding sequence of the target gene was amplified using the primers containing appropriate restriction enzyme sequence (Table 1), and cloned into TRV2 binary vector. Each vector was then mobilized into *A. tumefaciens* cells (GV3101). The cotyledons of 12-days-old cotton (*G. hirsutum*, cv. Coker 312, a glanded cultivar) seedlings were infiltrated with GV3101 strains containing TRV1 (pYL192) and GV3101 strains containing TRV2 (pYL156 carrying the target gene sequence selected to silence a particular gene) in a ratio of 1:1 (v/v). After infiltration, the plants were covered with Humidome™ and kept in dark for 24 h. Next day, the plants were transferred to a growth chamber at 12 h light/12 h dark cycle at 23° C. The second true leaf from each plant was harvested three weeks after infiltration for gland counting and terpenoid analyses. Glands were counted on the scanned image of the leaf using ImageJ software.

TABLE 1

| oligo | 5' to 3' sequence | Size (bp) |
| --- | --- | --- |
| GhA01G0267 EcoRI-F | CGgaattcCTGGGATCTCCCGAAAGCTAGC (SEQ ID NO: 9) | 634 |
| GhA01G0267 SacI-R | ACGCgagctcCTCATTCTATCTGTAACATGCCATTGGC (SEQ ID NO: 10) | |
| GhA10G0388 EcoRI-F | CGgaattcATGAGACGAAACTGCAACTTGGAG (SEQ ID NO: 11) | 357 |
| GhA10G0388 SacI-R | ACGCgagctcGTAAGGAGAGGTAGCTTGGATTCG (SEQ ID NO: 12) | |
| GhA12G2172 EcoRI-F | CGgaattcATGTCTTCCTCTTCTTCGTCTTCTC (SEQ ID NO: 13) | 600 |
| GhA12G2172 SacI-R | ACGCgagctcCGATTTAGTGAGTTGAAGGGTGC (SEQ ID NO: 14) | |
| GhA12G1233 XbaI-F | GCtctagaATGTGCAAAGGTTTACAACAAGGAAG (SEQ ID NO: 15) | 366 |
| GhA12G1233 XmaI-R | TCCCcccgggGGTTGTTGAAGACTCGGTTTCCGTG (SEQ ID NO: 16) | |
| GhD07G2328 XbaI-F | GCtctagaTCAAATGTTCTTCCCTATCTCGG (SEQ ID NO: 17) | 491 |
| GhD07G2328 XmaI-R | TCCCcccgggTCAGAAGGGAGTGTAAATCTGCA (SEQ ID NO: 18) | |
| GhD11G1055 XbaI-F | GCtctagaATGGAAGTCCTCATAATGTCTCCCTC (SEQ ID NO: 19) | 628 |
| GhD11G1055 XmaI-R | TCCCcccgggCCAGACCAATGAGATCGGATTC (SEQ ID NO: 20) | |
| GhA05G2973 EcoRI-F | CGgaattcATGGTTGGAGCTGGTGTCCTCAG (SEQ ID NO: 21) | 583 |
| GhA05G2973 SacI-R | ACGCgagctcCAACAGGGAAGTAGCACAAGGCC (SEQ ID NO: 22) | |
| GhA06G1947 XbaI-F | GCtctagaATGGAAGATGTGGAGATGGAGA (SEQ ID NO: 23) | 505 |
| GhA06G1947 XmaI-R | TCCCcccgggCTTCAAAGTTGTCTTTGGCATG (SEQ ID NO: 24) | |
| GhD05G0292 XbaI-F | GCtctagaATGGGCAGGAAATGCTCACATTG (SEQ ID NO: 25) | 614 |
| GhD05G0292 XmaI-R | TCCCcccgggAATCAATGCATCCGTACTGCAAC (SEQ ID NO: 26) | |
| GhD12G1160 XbaI-F | GCtctagaATGGAAGAACTAATCATCTCTCCATC (SEQ ID NO: 27) | 587 |
| GhD12G1160 XmaI-R | TCCCcccgggGATCCAAGTTCAAGAACACCACG (SEQ ID NO: 28) | |
| GhA08G2056 XbaI-F | GCtctagaATGAGCATGGTTCCATGGCACCA (SEQ ID NO: 29) | 630 |
| GhA08G2056 XmaI-R | TCCCcccgggTATCTTAACGATGGCTGCATGAACC (SEQ ID NO: 30) | |

Example 7

Terpenoid Estimation in the Leaves of VIGS-Infiltrated Seedlings

The second true leaf was harvested three weeks after *Agrobacterium* infiltration and frozen in liquid Nitrogen. The CGF2 and CGF3 knockout lines were grown in the greenhouse for about two months. One or two young, expanding leaves were harvested and immediately frozen in liquid nitrogen. At four months following transformation with an ACGF3 overexpression vector, callus lines representing individual events were segregated based on their light or dark colored appearance and frozen in liquid nitrogen. The leaves and callus tissues were freeze-dried for 60 h at −20° C. Each leaf sample was ground to a fine powder and 100 mg was used for extraction using acetonitrile:water:phosphoric acid (80:20:0.1). A 50 µL fraction of the extract was analyzed on a LC-1200 (Agilent Technology) High Pressure Liquid Chromatograph equipped with diode array detector for compound spectral identification as described by Stipanovic, et al., *J. Agric. Food Chem.* 36:509-515, 1988. Results are reported as µg terpenoid per mg dry weight of tissue.

Example 8 cDNA Amplification and qRT-PCR

Eight hundred nanograms of total RNA was reverse transcribed in 20 µl volume using an oligo poly-T primer and MultiScribe™ Reverse Transcriptase (Taqman RT kit; Applied Biosystems, Foster City, Calif.) following manufacturer's instructions. The cDNA amplification conditions were as follows: 25° C. for 10 min, 48° C. for 30 min, and 95° C. for 5 min. The cDNA was diluted to 100 µl, PCR was performed to check the cDNA amplification using Histone3 gene specific primers and then good quality cDNA was used for real-time PCR. cDNA was mixed with 2×SYBR Green PCR Master Mix (Applied Biosystems) with gene specific primers listed in Table 2. Histone3 was used as internal control. qRT-PCR reactions were carried out using Bio-Rad C1000 Touch™ Thermal Cycler (Bio-Rad Laboratories, Inc.) with the following conditions: 95° C. for 10 min followed by 40 cycles of 95° C. for 15 s, 60° C. for 1 min and plate read. Melting curve analysis was performed at the end of reaction to ensure a single product. Three biological replicates and three technical replicates were used for each type of sample. Relative expression levels were quantified using $2^{-\Delta\Delta C_T}$ method as described (Livak and Schmittgen, *Methods* 25:402-408, 2001).

TABLE 2

| Primer | Sequence 5' to 3' |
|---|---|
| A11CGF1-QF | CCAGCTTCGGTCCAGTTCCTTA (SEQ ID NO: 43) |
| A11CGF1-QR | GAGGAATCTTTCTTGGTTTGGTTATTGTTA (SEQ ID NO: 44) |
| D11CGF1-QF | AACCCCAGCTTCGATCCAGTTTCTTG (SEQ ID NO: 45) |
| D11CGF1-QR | AGGAATCTTTCTTGGTTTGGTTATTGCTG (SEQ ID NO: 46) |

TABLE 2 -continued

| Primer | Sequence 5' to 3' |
|---|---|
| A01CGF2-QF | CAGATAGAATGAGTAGTGCTGCAAT (SEQ ID NO: 47) |
| A01CGF2-QR | GGCCTCAGTGAAGAAATCATCG (SEQ ID NO: 48) |
| D01CGF2-QF | CAGATAGAATGAGTAGTGCTGCAAC (SEQ ID NO: 49) |
| D01CGF2-QR | CAATTGGCCTCAGTGAAGAAATCATCA (SEQ ID NO: 50) |
| A12CGF3-QF | TGTGAAGATAGTAGGATCCGAAGCT (SEQ ID NO: 51) |
| A12CGF3-QR | GTAGGGACTCTGACAACAACATCC (SEQ ID NO: 52) |
| D12CGF3-QF | TGTGAAGATAGTAGGATCCGAAGCC (SEQ ID NO: 53) |
| D12CGF3-QR | GTAGGGACTCTGACAACAACATCT (SEQ ID NO: 54) |

Example 9

Sequencing of CGF Genes in Both a and D Genomes of GVS4 and GVS5

PCR was performed using Phusion polymerase (NEB), on genomic DNA isolated from GVS4 and GVS5 lines using gene specific primers (Table 3) which can also differentiate between the homeologs of A and D genomes.

TABLE 3

| Primer | Sequence 5' to 3' | Purpose |
|---|---|---|
| A11GhCGF-prom-3F | CTCTCCAAAATCAACCATACTCACAAA TGCCTAC (SEQ ID NO: 31) | To amplify CGF1 from A genome |
| A11GhCGF-term-R | CTCCATGGCATCCTCAAGTCACAG (SEQ ID NO: 32) | |
| GhCGFD11-prom-F | ATCTTCTCACTCCGAAACCGACC (SEQ ID NO: 33) | To amplify CGF1 from D genome |
| D11GhCGF-term-R | TGGAAGAAACAAGATCGGATGTGGC (SEQ ID NO: 34) | |
| A01CGF2-P-F | GGCTGTCAGATGTAGTAAAATCAGTAT TGGT (SEQ ID NO: 35) | To amplify CGF2 from A genome |
| A01CGF2-T-R | CAAATATATATGGGTCTGATATGCATG TCTCC (SEQ ID NO: 36) | |
| D01CGF2-P-F | CAAAGTGTTGATTTCAGCAATAACTTG TAGC (SEQ ID NO: 37) | To amplify CGF2 from D genome |
| D01CGF2-T-R | CGTAACAAAATGGTTTTCGTATGTTAC GTATC (SEQ ID NO: 38) | |
| A12CGF-prom-F | CATCCCATACAAACTATTAACAAGATT ACGTCGGATG (SEQ ID NO: 39) | To amplify CGF3 from A genome |
| A12CGF-term-R | GTGATCATCATCAAGCACAGGCTACTG (SEQ ID NO: 40) | |
| D12CGF-Prom-F | CAAACCATCAACAAGACTACGTTGGACA (SEQ ID NO: 41) | To amplify CGF3 from D genome |
| D12CGF-term-R | CTAATTTAAGTGATCATCATCAAGCACA GTCTAATC (SEQ ID NO: 42) | |

Amplified products were gel-eluted and sequenced by the Sanger method, using the primers shown in Table 4, below. Obtained sequences were aligned and analyzed to identify the mutations using SnapGene software. Four other glandless lines, Acala glandless, NM13P1088, NM13P1115 and NM13P1118 were used to determine the cause of glandless phenotype in each. PCR reactions were performed on genomic DNA from each of the four glandless lines to amplify the CGF3 gene from both A and D subgenomes, using primers specific to each homeolog (Table 3, above). Amplified fragments were gel eluted and sequenced using the primers shown in Table 4, below. Sequences obtained were analyzed with SnapGene software.

TABLE 4

| Primer | Sequence 5' to 3' | Purpose |
|---|---|---|
| A11GhCGF-P-4F | GTTATTTGATTGCTTCGTCAGTTACG (SEQ ID NO: 55) | to sequence CGF1 gene both homeologs |
| GhCGF-prom1.6kb-R | GTTTCCTATACTAAACTCAAGAGG (SEQ ID NO: 56) | |
| GhCGF-R1 | TTACTGCAGATCTAGCCTCCTGAG (SEQ ID NO: 57) | |
| GhCGF-R2 | GAGCGTAGAATCTGTGGTTCAGC (SEQ ID NO: 58) | |
| GhCGF-R3 | GCAACTCATGAGCACCAGTTAACC (SEQ ID NO: 59) | |
| GhCGF-R4 | TCCTGGGAAAAGGAAACCAGAG (SEQ ID NO: 60) | |
| GhCGF_prom1kb-R | TGTCACATTAGCATGAGGTACATGTGG (SEQ ID NO: 61) | |
| D11GhCGF-prom-2F | TAAGGTACACGAGGCACAGCACAC (SEQ ID NO: 62) | |
| CGF2-C-2F | AGAGAGTGAATCGTACTTCTTCTGC (SEQ ID NO: 63) | to sequence CGF2 gene both homeologs |
| CGF2-C-F | ATGATGAACGTCGACGACGTCC (SEQ ID NO: 64) | |
| CGF2-C-R | TCGCTTGAAGATTCGACATATGGTCC (SEQ ID NO: 65) | |
| CGF2-P-2F | GCAACCCTACTCCTATACTTCAATCTAG (SEQ ID NO: 66) | |
| CGF2-P-3F | GCTAGATGTGGTGTTGCCTCAC (SEQ ID NO: 67) | |
| CGF2-P-F | CAAGAATAGTCTAAGCTTCTCTAGCAAATGATC (SEQ ID NO: 68) | |
| CGF2-T-2R | ACTGGAGTACATCCATGTCAGTCTC (SEQ ID NO: 69) | |
| CGF3-cds-2F | AGTTCTGGGATCAACAACAGCCTG (SEQ ID NO: 70) | to sequence CGF3 gene both homeologs |
| CGF3-cds-3F | GGCCAAAGACAGTGGAAGTTGATG (SEQ ID NO: 71) | |
| CGF3-cds-F | ATGTCTTCCTCTTCTTCGTCTTCTC (SEQ ID NO: 72) | |
| CGF3-prom-2F | GGTTTCTTGAATCTAGTGAAGGATTGATTGTTG (SEQ ID NO: 73) | |
| CGF3-prom-3F | TTGCAAATTGAGAGAGTGATCATTGAGAC (SEQ ID NO: 74) | |
| CGF3-prom-4F | CATGAGTGGAGGGGTTAAGACGCC (SEQ ID NO: 75) | |
| CGF3-Tn-2F | TGACACTGCTAGTGCAGTCACTCTG (SEQ ID NO: 76) | to sequence the transposon in the coding region of ACGF3 gene in the glandless GVS5 |
| CGF3-Tn-3F | GACACAAGCATCATAGTCACATCTTGTG (SEQ ID NO: 77) | |
| CGF3-Tn-4F | TAACTGGAAGGTTCTATACCAATGGACTC (SEQ ID NO: 78) | |
| CGF3-Tn-5F | CAAATAACAAGCAGTATTAACAGCTTCAGC (SEQ ID NO: 79) | |
| CGF3-Tn-6F | ATATGCCATAACTTCGTGGTGTCAG (SEQ ID NO: 80) | |
| CGF3-Tn-7F | TTCTTGGACTGCGATCTAGGATGG (SEQ ID NO: 81) | |
| CGF3-Tn-8F | GCAATCCTTGTTGAACCAGCACT (SEQ ID NO: 82) | |
| CGF3-Tn-F | AAGCCATTTCTTAACAAATCTCCACCTTG (SEQ ID NO: 83) | |
| D12.CGF3.epro-F | AGCTCAATTTGGGGAGTTTACTTGC (SEQ ID NO: 84) | to sequence the additional ~2 kb promoter sequence of the DCGF3 in glanded and |
| D12.CGF3.epro-F2 | GTAAGTTCCACAAAGGAAAACTCAACAC (SEQ ID NO: 85) | |
| D12.CGF3.epro-F3 | CATAACCTTCCTTAGGTTGACCTCG (SEQ ID NO: 86) | |
| D12.CGF3.epro-F4 | GAATCACATGGTCTGGATCCTCATAG (SEQ ID NO: 87) | |
| D12.CGF3.epro-F5 | AGAAACACTGATTGGCGGTTC (SEQ ID NO: 88) | |

TABLE 4 -continued

| Primer | Sequence 5' to 3' | Purpose |
|---|---|---|
| D12.CGF3.epro-R | GGAATGTAATACCCTGTCCAACGTAG (SEQ ID NO: 89) | glandless cotton |
| D12.CGF3.epro-R2 | CGATATTGTGTATGTTTGTGTGATGC (SEQ ID NO: 90) | |

Example 10

RNA Isolation and Sequence Analysis of Transcripts

The developing cotton embryos at three different stages of development (14, 16 and 32 dpa), representing the gland formation and active stage of gland filling, were used for transcriptome analysis. Embryos from Stoneville 7A Glanded (GVS4) and glandless (GVS5) near-isogenic lines were compared to find differentially expressed genes. No glands were observed in 14 dpa embryos of GVS4, however, at 16 dpa some glands were seen in the embryos from this line. Gossypol, the major storage terpenoid of seed-glands, can be detected in the embryos of glanded cotton plants around 24 dpa and later (Scheffler, et al., J. Cotton Sci. 18:420-429, 2014). No glands were detected in line GVS5 embryos at any stage of development. RNA was isolated from three replicate samples of 14, 16, and 32 dpa embryos each from these glanded and glandless lines. RNA-seq was performed on these six tissues and a total 377 million clean paired reads were obtained. Out of these, 273 million unique reads (72.13%) were mapped to the reference genome (Zhang, et al., Nat. Biotech. 33:531-537, 2015), 22.82% of them mapped more than one time, and 5.05% reads were not mapped to the reference genome. Overall, 94.95% of reads were mapped to the reference genome. Only the uniquely mapped reads were used to measure transcript abundance. Tissue-wise data for the mapped reads is given in Table 5, which shows RNA-seq reads for glanded (GL; GVS4) and glandless (gl; GVS5) embryos at 14, 16 and 32 days post-anthesis and their mapping to the reference genome.

Example 11

Differential Gene Expression Analysis

To ascertain transcript abundance, the uniquely mapped reads were quantified using Hisat2 program to obtain read count values for all the known 70,478 genes in G. hirsutum (Zhang, et al., Nat. Biotech. 33:531-537, 2015). Of these, 57,510 genes were expressed in at least one of the six tissue types analyzed. Genes that have >1 read count value in any one of the tissues were considered to be expressed. At least, 30 million unique reads were obtained for each tissue (every replicate had 10 million or more read counts). DEseq2 program was used for differential gene expression analysis (log fold change≥2 and FDR<0.05). FIG. 1 shows the number of genes that are up or down regulated between glanded and glandless embryos at different time points. At 14 dpa, a small number of genes were differentially expressed, with only 33 genes up-regulated in the glanded embryos and seven down-regulated. Table 6 shows the 33 genes that were down-regulated in the 14 dpa embryos of glandless cotton plant. This stage of development was focused on to identify the genes that are responsible for and involved in gland formation. A similar time frame for gland initiation was identified in other studies (Reeves and Beasley, J. Agric. Res. 51:935-944, 1935; Scheffler, et al., J. Cotton Sci. 18:420-429, 2014). Genes encoding transcription factors and a transporter protein were tested for their role in gland formation using virus induced gene silencing (VIGS). Note that because of a high degree of homology between the two homeologs, the same VIGS construct will silence both the copies in A and D genomes. At 16 dpa, 178 genes were expressed at higher levels and 73 genes at lower levels in the glanded embryos. At 32 dpa, 894 genes were expressed at higher levels and 240 genes at lower levels in the glanded embryos.

TABLE 5

| Tissue Type | Quality Filtered Paired Reads | Uniquely Mapped Reads | Reads Mapped More Than 1 Time | Total Mapped reads | Reads Not Mapped | % Not Mapped | % Mapped 1 Time | % Mapped >1 Time | % Total Mapped |
|---|---|---|---|---|---|---|---|---|---|
| 14GL | 57,526,347 | 41,539,721 | 13,219,522 | 54,759,243 | 2,767,104 | 4.81 | 72.21 | 22.98 | 95.19 |
| 14gl | 55,574,944 | 39,411,172 | 13,043,137 | 52,454,309 | 3,120,635 | 5.62 | 70.92 | 23.47 | 94.38 |
| 16GL | 45,027,488 | 31,957,244 | 10,240,975 | 42,198,219 | 2,829,269 | 6.28 | 70.97 | 22.74 | 93.72 |
| 16gl | 58,872,534 | 41,914,607 | 13,567,579 | 55,482,186 | 3,390,348 | 5.76 | 71.20 | 23.05 | 94.24 |
| 32GL | 78,953,741 | 57,667,091 | 18,523,395 | 76,190,486 | 2,763,255 | 3.50 | 73.04 | 23.46 | 96.50 |
| 32gl | 81,721,688 | 60,837,058 | 17,351,295 | 78,188,353 | 3,533,335 | 4.32 | 74.44 | 21.23 | 95.68 |
| | 377,676,742 | 273,326,893 | 85,945,903 | 359,272,796 | 18,403,946 | 5.05 | 72.13 | 22.82 | 94.95 |

TABLE 6

| Gene | Laboratory Designation | VIGS | Size bp | Putative Function |
|---|---|---|---|---|
| Gh_A11G0909 | CGF1 | Yes | 1488 | Basic helix-loop-helix (bHLH) DNA-binding family protein |
| Gh_D11G1055 | CGF1 | | 1488 | Basic helix-loop-helix (bHLH) DNA-binding family protein |
| Gh_A01G0267 | CGF2 | Yes | 960 | NAC domain containing protein 42 |
| Gh_D01G0278 | CGF2 | | 963 | NAC (No Apical Meristem) domain transcriptional regulator superfamily protein |
| Gh_A12G2172 | CGF3 | Yes | 1428 | Basic helix-loop-helix (bHLH) DNA-binding family protein |
| Gh_D12G2351 | CGF3 | | 1428 | Basic helix-loop-helix (bHLH) DNA-binding family protein |
| Gh_A10G0388 | | Yes | 363 | Jasmonate-zim-domain protein 8 |
| Gh_D10G0403 | | | 363 | Jasmonate-zim-domain protein 8 |
| Gh_A12G1233 | | Yes | 393 | B-box type zinc finger family protein |
| Gh_D12G1358 | | | 393 | B-box type zinc finger family protein |
| Gh_A01G0135 | | No | 1020 | Zinc finger C-x8-C-x5-C-x3-H type family protein |
| Gh_A04G0546 | | No | 192 | HEAT repeat; WD domain, G-beta repeat protein |
| Gh_A05G0334 | | No | 987 | NAD(P)-binding Rossmann-fold superfamily protein |
| Gh_A05G2973 | | No | 1077 | Lysine histidine transporter 1 |
| Gh_A06G0017 | | No | 555 | Thioredoxin superfamily protein |
| Gh_A06G0018 | | No | 768 | Expansin 11 |
| Gh_A06G0213 | | No | 957 | Uncharacterized protein |
| Gh_A06G1947 | | Yes | 930 | NAC domain containing protein 42 |
| Gh_A08G2056 | | Yes | 867 | NAC domain containing protein 42 |
| Gh_A10G0667 | | No | 2202 | Pectin lyase-like superfamily protein |
| Gh_A12G1784 | | No | 711 | Integrase-type DNA-binding superfamily protein |
| Gh_A12G2056 | | No | 1251 | Uncharacterized protein |
| Gh_A13G0385 | | No | 660 | S-methyl-5-thioribose kinase |
| Gh_D04G0529 | | No | 1251 | Phosphoenolpyruvate (pep)/phosphate translocator 2 |
| Gh_D05G0292 | | Yes | 768 | myb-like transcription factor family protein |
| Gh_D05G0439 | | No | 894 | NAD(P)-binding Rossmann-fold superfamily protein |
| Gh_D06G1859 | | No | 987 | P-loop containing nucleoside triphosphate hydrolases superfamily protein |
| Gh_D07G2328 | | Yes | 501 | WRKY family transcription factor family protein |
| Gh_D08G2336 | | No | 345 | Uncharacterized protein |
| Gh_D11G0631 | | No | 417 | Uncharacterized protein |
| Gh_D11G0996 | | No | 894 | Cytokinin response factor 6 |
| Gh_D12G1160 | | Yes | 1464 | Basic helix-loop-helix (bHLH) DNA-binding family protein |
| Gh_Sca007330G01 | | No | 630 | Plant invertase/pectin methylesterase inhibitor superfamily protein |

Example 12

Figure 2:
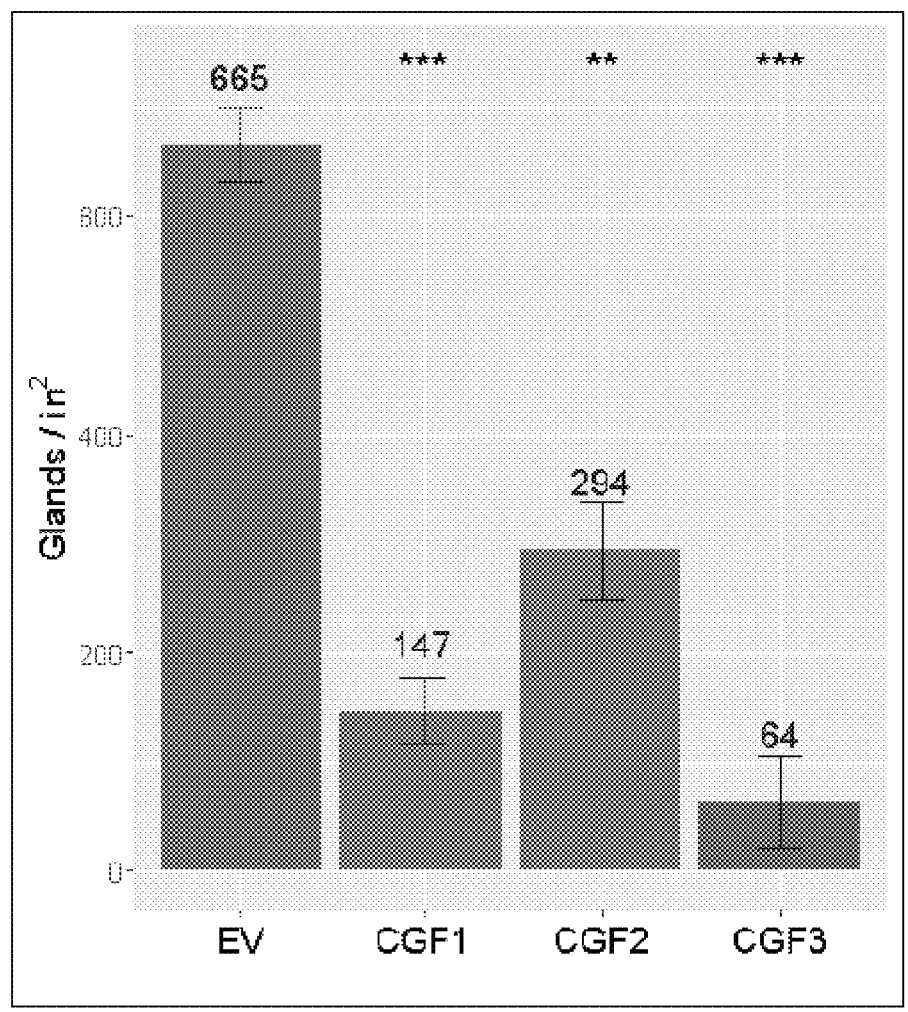
FIG. 2. Effect of Virus-induced Gene Silencing (VIGS) of the CGF1, CGF2, and CGF3 genes on gland number in the leaf. EV: empty vector control. Note that the same VIGS construct will target the homeologous copies of the respective gene in both A and D genomes. The plots were generated using the R software. p<0.01, *p<0.001 as tested by the t-test.

Virus-Induced Gene Silencing (VIGS) to Identify Genes Involved in Gland Formation VIGS is a simple, yet powerful method to silence a target gene in the young emerging leaves of a plant in a temporary manner. Therefore, VIGS was used to target individual genes for silencing in the new emerging leaves of a cotton seedling in order to understand their role in gland development. With the exception of a gene that encodes a transporter, the rest of the genes examined encode transcription factors as one or more of these genes are likely to be responsible for gland development. In case of a gene that was found to be differentially expressed in A as well as D subgenomes, a single VIGS construct was used that will target both the homeologs (Table 6). Of the ten genes targeted in this manner, negative effects on the formation of glands were only observed in case of three genes that encode transcription factors. The term: "Cotton Gland Formation" (CGF) is used herein for these genes. A dramatic reduction was seen in the number of glands in response to silencing of two genes, Gh_A11G0909/Gh_D11G1055 (CGF1; 78% reduction) and Gh_A12G2172/Gh_D12G2351 (CGF3; 90% reduction) (FIG. 2). The reduction of glands in the newly emerging leaves was observed starting at 2-weeks post-infiltration. At 21 days post-infiltration, the leaves were scanned to document the results and the gland number was quantified. VIGS silencing of another gene, Gh_A01G0267/Gh_D01G0278 (CGF2), did not show such a dramatic reduction in the number of glands compared to that for CGF1 and CGF3. However, the visual and microscopic appearance of the glands was qualitatively different in terms of color intensity and structure, as though their development was adversely affected. No effects on gland number/formation were observed with the remaining seven VIGS constructs.

Figure 3:
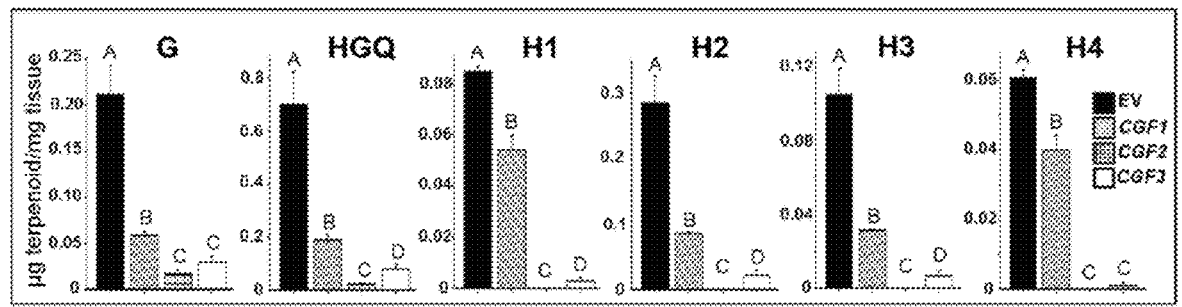
FIG. 3. Effect of Virus-induced Gene Silencing (VIGS) of the CGF1, CGF2, and CGF3 genes on terpenoid levels in the leaves. EV: empty vector control; G: gossypol; HGQ: hemigossypolon; H: heliocides. Note that the same VIGS construct will target the homeologous copies of the respective gene in both A and D subgenomes. The plots were generated using the R software. The values indicated by bars within a group are significantly different at p<0.05 if labeled with different letters.

Unlike the glands in cottonseed that contain mainly the gossypol, the glands in the leaves of a cotton plant contain not only gossypol, but also hemigossypolon and heliocides that are derived from the same biosynthesis pathway. Thus, a lower number of functional glands would be expected to result in lower amounts of these terpenoids in the leaves of cotton plants that have undergone VIGS against the CGF genes. Therefore, HPLC analysis was conducted to measure the levels of these terpenopids in the leaves. Results from this analysis are shown in FIG. 3. A significant reduction in the level of gossypol and related terpenoids (hemigossypolon and heliocides) was observed in the leaves of plants that were subjected to VIGS-mediated silencing of CGF1, CGF2 or CGF3 genes. Since the terpenoids are usually produced and stored in the glands, the reduced levels of these compounds are likely a result of lower gland numbers or lesser number of functional glands. Thus, based on the results from RNA-seq analysis and VIGS experiments, three genes and their homeologs (encoding transcription factors) have been identified that play a very important role in the formation of glands in the cotton plant. The CGF gene homeologs of the A subgenome will be referred to as ACGF and those of the D subgenome as DCGF.

Example 13

Gene Expression Analysis of Selected CGF Genes

Figure 4:
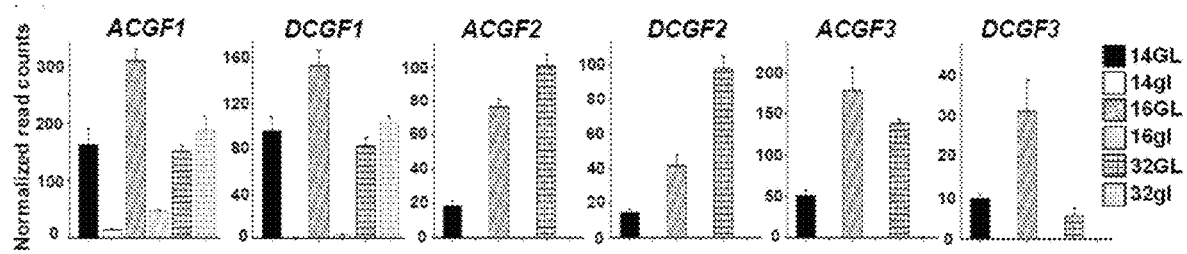
FIG. 4. Mean normalized read counts of three biological replicates, based on RNA-seq analysis, for the three CGF genes in A and D subgenomes at 14, 16 and 32 day post-anthesis embryos from glanded (GL) and glandless (gl) cotton plants.
Figure 5:
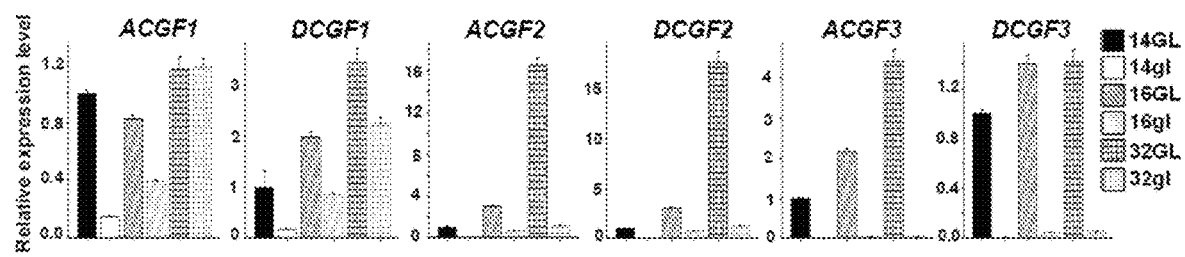
FIG. 5. qRT-PCR results showing relative expression levels for the three CGF genes in A and D subgenomes at 14, 16, and 32 day post-anthesis embryos from glanded (GL) and glandless (gl) cotton plants. This analysis was conducted to validate RNA-seq results.

Transcript abundance for the CGF genes (and the respective homeologs) in glanded and glandless embryos at different developmental stages is provided as normalized read counts in Table 7 and FIG. 4. Table 7 shows the mean normalized read count values of three biological replicates, based on RNA-seq analysis for the three CGF genes in A and D subgenomes at 14, 16 and 32 day post-anthesis embryos from glanded (GL) and glandless (gl) cotton plants. To validate the expression profile of these genes, qRT-PCR was performed using the same set of RNA samples that were used to perform RNA-seq analysis. Results obtained from this analysis validated the expression profile of the three CGF genes that was observed with RNA-seq analysis (FIG. 5). Expression of these genes in the glandless embryos was lower at 14 and 16 dpa compared to that in the glanded embryos at that stage of development.

region (4.2 kb in case of DCGF3), UTRs, introns (if present), exons, and terminator. No sequence differences were found between glanded and glandless cotton plants with regards to CGF1 genes in the A (SEQ ID NO:1) or D (SEQ ID NO:2) genome or the CGF2 genes in the A (SEQ ID NO:3) or D (SEQ ID NO:4) genome and the respective homeologs.

Figure 6:
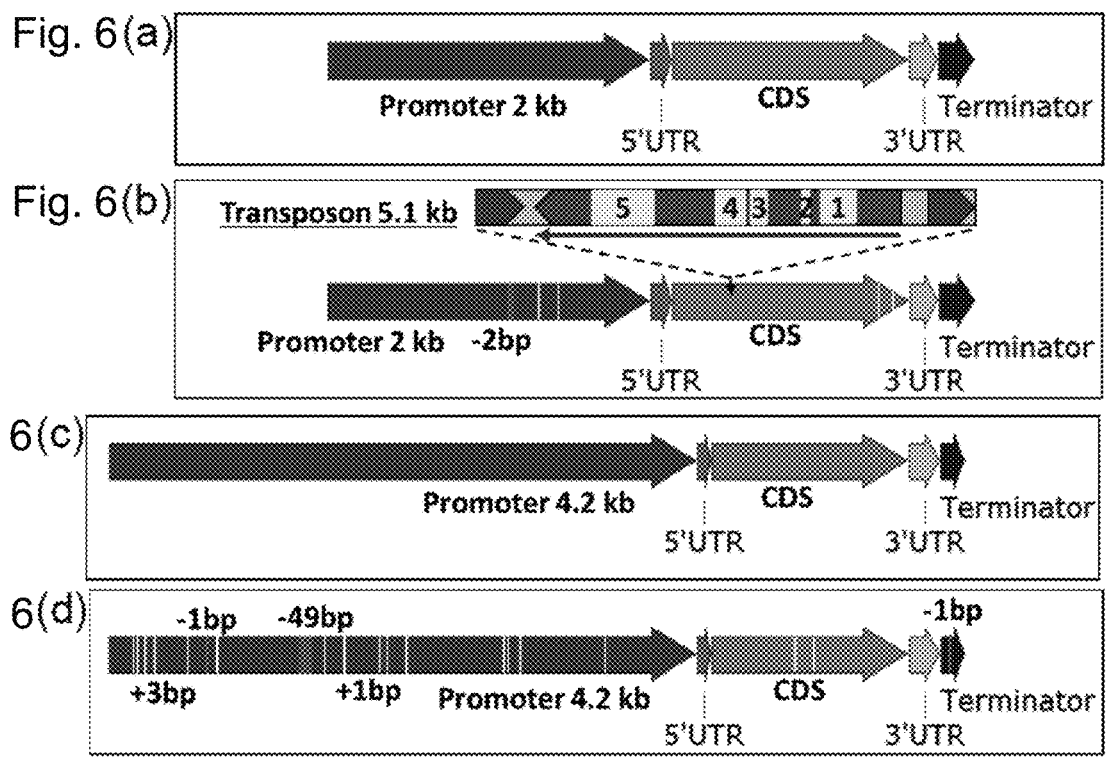
FIG. 6A, FIG. 6B, FIG. 6C and FIG. 6D. Illustration showing differences between glanded and glandless cotton for CGF3 gene in A- and D-subgenome.

Major sequence differences between the glanded and glandless cotton plants were observed in both CGF3 gene homeologs. The glandless line (GVS5) showed a 5.1 kb transposon insertion between 362 and 363 bp of the coding sequence of the ACGF3 gene (Gh_A12G2172; FIG. 6B; SEQ ID NO:6) compared to the wild-type glanded cotton (GVS4; FIG. 6A; SEQ ID NO:5). In addition, there were two SNPs and a 2-bp deletion in the promoter sequence, and two SNPs in the coding sequence of Gh_A12G2172 gene in the glandless GVS5 (SEQ ID NO:6) compared to the wild-type glanded cotton (GVS4; SEQ ID NO:5). The coding sequence of the DCGF3 gene (Gh_D12G2351) of the glandless mutant (GVS5; SEQ ID NO:8) has two SNPs (one synonymous and one nonsynonymous) compared to the wild-type glanded cotton (GVS4; SEQ ID NO:7). In addition, the terminator sequence of the DCGF3 from the glandless mutant line (GVS5; SEQ ID NO:8) has one base pair deletion compared to the wild-type glanded cotton (GVS4; SEQ ID NO:7). However, the significant differences in the DCGF3 gene between glanded and glandless cotton were in the promoter. The ~4.2 kb promoter region of this gene in the glandless mutant (GVS5; FIG. 6D; SEQ ID NO:8) had fifteen SNPs, two deletions (1 and 49 bp long), and two insertions (1 and 3 bp) compared to the glanded cotton (GVS4; FIG. 6C; SEQ ID NO:7).

Example 15

Sequencing of CGF Genes

There are some genes in an allotetraploid such as *G. hirsutum* in which one homeolog for a particular gene is expressed while the other remains silent in a given tissue

TABLE 7

| Gene | Designation | 14GL | 14gl | 16GL | 16gl | 32GL | 32gl |
|---|---|---|---|---|---|---|---|
| Gh_A11G0909 | CGF1 | 162.42 | 13.76 | 308.94 | 47.3 | 150.77 | 187.34 |
| Gh_D11G1055 | CGF1 | 97.07 | 0.25 | 156.41 | 2.88 | 83.26 | 104.18 |
| Gh_A01G0267 | CGF2 | 18.96 | 0 | 76.39 | 0 | 100.81 | 0 |
| Gh_D01G0278 | CGF2 | 14.64 | 0 | 41.68 | 0 | 97.74 | 0 |
| Gh_A12G2172 | CGF3 | 51.7 | 0 | 178.37 | 0 | 138.09 | 0.35 |
| Gh_D12G2351 | CGF3 | 9.86 | 0 | 30.98 | 0 | 5.57 | 0 |

Example 14

Sequencing of CGF Genes

The results for the expression profile of CGF genes show that these genes have little or no activity in the glandless embryos, especially at 14 dpa stage. In order to understand the reasons for these differences, each of these genes was sequenced and their homeologs from glanded and glandless cotton plants. Large PCR fragments were amplified from the genomic DNA of glanded and glandless cotton plants using specific primers (Table 3) that can differentiate between the A and D subgenome homeologs of each of the CGF genes. These amplicons included approximately 2 kb of promoter (Adams et al., *Proc. Natl. Acad. Sci. USA* 100:4649-4654, 2003; Grover et al., *New Phytologist* 196:966-971, 2012). As detailed above, RNA-seq results showed that while both the A- and D-subgenome homeologs of the CGF3 gene were expressed in the developing embryos of the glanded cotton, the DCGF3 was less active (FIG. 4). In order to further confirm whether both the homeologs of the CGF3 gene are expressed in the embryos of glanded cotton, a PCR amplicon was generated with a primer set which can amplify both A and D-subgenome homeologs using the cDNA from 14-dpa embryos. Direct sequencing of this amplicon clearly showed the expected SNPs, thus confirming the results from RNA-seq analysis and qRT-PCR showing that both the CGF3 homeologs are expressed in the embryos of glanded cotton.

Example 16

Sequence and Activity Analysis of Promoter of DCGF3

As described earlier, the CGF3 homeologs in both the A and D subgenomes show no expression in the embryos of glandless GVS5 (FIG. 4 and FIG. 5). The undetectable level of expression of the CGF3 gene in the A subgenome is likely due the insertion of the 5.1 kb transposon (FIG. 6B). Initially only ~2 kb of the promoter (2,009 bp), 5'-UTR (97 bp), the coding sequence, 3'-UTR and 182 bp of the terminator region of the DCGF3 gene was amplified from glanded and glandless cotton. Four SNPs were detected in the promoter region and two SNPs in the coding sequence between glanded and glandless cotton. To investigate whether these SNPs in the promoter region were responsible for the lack of transcripts in the glandless GVS5, we assembled promoten: gusA constructs using longer promoter fragments.

Approximately 2.1 kb and 4.2 kb upstream sequences from the transcription start codon of the D subgenome CGF3 gene were PCR amplified from both glanded and glandless cotton plants using the primers listed in Table 8 (the reverse primer is the same for both promoter sizes). The templates used in these PCR reactions were amplicons that were specific to the D subgenome of either the glanded or glandless CGF3 gene, previously generated for sequencing of the CGF3 gene including promoter, coding sequence and the terminator. Each of the 'promoter' amplicons was then cloned into pCAMBIA 2301 vector to replace the CaMV 35S promoter that drove the expression of the reporter gene gusA. This cloning was done using the NEBuilder® HiFi DNA assembly cloning kit (#E5520S; NEB) as per manufacturer instructions. Each of these binary vectors was introduced into *A. tumefaciens* strain LBA4404. The pCAMBIA 2301 vector, wherein gusA is under the control of CAMV 35S promoter was used as a control. Each of the *Agrobacterium* strains were used individually to infect cotton seedling explant to obtain stable transformed callus cultures (Rathore, et al., In: *Agrobacterium Protocols: Volume* 2 (Wang, K. ed) pp. 11-23. New York, N.Y.: Springer New York, 2015). Histochemical GUS assays were performed on the stably transformed callus tissue and GUS activity was examined at five weeks after transformation of cotyledon, hypocotyl and cotyledonary petiole explants (Jefferson, *Plant Mol. Biol. Rep.* 5:387-405, 1987; Jefferson, et al., *EMBO J.* 6:3901-3907, 1987).

TABLE 8

| Promoter fragment | Primer | Sequence 5' to 3' |
|---|---|---|
| ~2.1 kb promoter | 2301-DCGF3_pro_frag1-F | TCGAGCTCGGTACCCGGGGATCCTCTAGA GTCGACCTGCAGCAAACCATCAACAAGA CTACGTTGGAC (SEQ ID NO: 91) |
| | DCGF3_promoter_frag1-R | GAAGGAGAAAAACTAGAAATTTACCCTC AGATCTACCATAAGCTTTATTGAATATGA TAGTGTGTACTACTGTTTTTCAAAGAGAA AAAAG (SEQ ID NO: 92) |
| ~4.2 kb promoter | DCGF3_1.pro.F1-F | TCGAGCTCGGTACCCGGGGATCCTCTAGA GTCGACCTGCAGCTTCCCTATAACACCCC AATCCACG (SEQ ID NO: 93) |
| | DCGF3_promoter_frag1-R | SEQ ID NO: 92 |

Promoter::gusA constructs using ~2.1 kb long promoter (including 5'-UTR) sequences from the DCGF3 gene of GVS4 and GVS5 were prepared. *Agrobacterium tumefaciens* cells containing the reporter gene construct were used to transform hypocotyl segments of cotton seedlings. Callus tissue growing on hypocotyl segments following transformation were examined histochemically for GUS activity, 30 days after transformation. The results show clearly that the D subgenome CGF3 gene promoter sequences (~2.1 kb) from the glanded and glandless cotton were equally active. It is possible that the ~2.1 kb sequence does not fully represent the entire promoter region of this gene and that important regulatory elements reside further upstream. Therefore a longer, ~4.2 kb of the promoter region of the DCGF3 gene was isolated from glanded (GVS4) and glandless (GVS5) cotton. As described earlier, the ~4.2 kb promoter region of this gene in the glandless mutant (GVS5) showed significant mutations, including fifteen SNPs, two deletions (1 and 49 bp long), and two insertions (1 and 3 bp) compared to the glanded cotton (GVS4).

In order to examine whether these sequence differences in the glandless cotton were responsible for the lack of expression of the DCGF3 gene, reporter gene constructs were assembled as described above. Callus tissues growing from the transformed cotyledon, hypocotyl and petiole explants were examined histochemically for GUS activity, five weeks after *Agrobacterium*-mediated transformation with each of the constructs. The results showed that while the tissue transformed with a construct wherein the gusA gene was under the control of DCGF3 promoter from glanded cotton showed strong GUS activity, the callus originating from explants following transformation with glandless DCGF3 promoter construct showed drastic reduction in reporter gene activity. The results suggest that the lack of DCGF3 transcripts in the glandless (GVS5) cotton is due to the attenuation of the activity of its heavily mutated promoter.

Example 17

Sequencing CGF3 Gene from Four Additional Glandless Lines

In order to further explore the genetic basis of the glandless phenotype in cotton germplasm, four additional glandless cotton cultivars developed by other breeders [Acala cultivar, NM-13P1088, NM-13P1115 and NM-13P1117 strains; (Bowman et al., *Mississippi Agricultural & Forestry Experiment Station Bulletin* 1155, 2006; Zhang et al., *Euphytica* 198:59-67, 2014)] were examined for allelic variation in the CGF3 gene pair by PCR amplification and sequencing. PCR reactions were performed on genomic DNA from each of the four glandless lines to amplify the CGF3 gene from both A and D subgenomes, using primers specific to each homeolog. Amplified fragments were gel eluted and sequenced. The amplification and sequencing primers are shown in Table 3 and Table 4, above. Sequences obtained were analyzed with SnapGene software.

The results showed that the glandless Acala GLS and NM-13P1088 had the same transposon insertion in the ACGF3 gene found in the GVS5 line. Based on written and oral pedigree information, both the GVS5 and the Acala glandless lines have the Hopi Moencopi glandless source in their ancestries that was discovered and described during the mid-twentieth century. The other two glandless cottons (NM-13P1115 and NM-13P1117) had a total of three SNPs in the coding region of ACGF3 gene, including two synonymous and one nonsynonymous, at residue 43, which alters an alanine to valine. Thus, these two lines have the same dominant mutation Gle2 obtained through irradiation to create the Egyptian glandless cotton as reported previously (Kohel and Lee, *Crop Sci.* 24:1119-1121, 1984; Ma et al., *Nat. Commun.* 7:10456, 2016).

Example 18

CRISPR/Cas9-Mediated Knockout of CGF2 and CGF3 Genes

The CRISPR/Cas9 system was used to knockout CGF2 and CGF3 genes in order to validate their role in gland formation. Two separate sgRNAs were used to target each of the CGF genes to improve the chances of getting a total knockout (given that cotton is a tetraploid, even a single-copy gene will have four targets in its genome). To design the guide sequences, sgRNAScorer (Chari et al., *Nat. Meth.* 12:823-826, 2015) and WU-CRISPR (Wong et al., *Genome Biol.* 16:1, 2015) were used. Based on the predicted scores from these tools, two guide RNA sequences were selected for CGF2 gene (Table 9). For CGF3 gene, WU-CRISPR did not predict any guide sequence in the desired region. However, using the sgRNAScorer, three potential guide sequences were identified (Table 9).

TABLE 9

| Target Name | Sequence 5' to 3' |
|---|---|
| CGF2-guide-1 | GCTCAAACAGGTGATCATCA (SEQ ID NO: 94) |
| CGF2-guide-2 | GATTGGAAAAGGCGACGACAG (SEQ ID NO: 95) |
| CGF3-guide-1 | AATTGGGGTCCAGTTTCGAG (SEQ ID NO: 96) |

TABLE 9 -continued

| Target Name | Sequence 5' to 3' |
|---|---|
| CGF3-guide-2 | AGTGATGGACGTGGACCGTA (SEQ ID NO: 97) |
| CGF3-guide-3 | GCTTCTCTAACACGCTCACAC (SEQ ID NO: 98) |

Initially, each guide sequence was cloned into either pTC241 or pTC242 plasmid. The promoters regulating the expression of sgRNA in these vectors are AtU6 and At7SL, respectively. The two sgRNA cassettes were incorporated into plasmid pCGS754. The final assembled vector contains nptII expression cassette for selection, a Cas9 expression cassette and two sgRNA cassettes. The binary vector LCT236 contains CGF2-guide-1, CGF2-guide-2 as guide sequences and targeted CGF2 genes, while LCT237 contains CGF3-guide-1, CGF3-guide 2 as guide sequences, and LCT238 contains CGF3-guide-2, CGF3-guide-3 as guide sequences and targeted CGF3 genes. Thus, one of the two sgRNAs used in assembling LCT237 and LCT238 was common between them. Each construct was mobilized into *Agrobacterium tumefaciens*, strain LBA4404 that was used to transform and generate cotton plants as described herein.

Targeted disruption of the CGF genes was expected to have a negative impact on the formation of glands and terpenoids that accumulate within them. Selected plants showing such a phenotype were sequenced to characterize mutations in their respective target genes. A PCR amplicon that encompasses the two target sites in each gene was generated from the genomic DNA isolated from the leaves of selected T0 plants. Each set of PCR primers contained a unique combination of barcodes for identification purposes (Table 10).

TABLE 10

| Primer | Sequence 5' to 3' |
|---|---|
| A_CGF2.Ampseq-F | gtactcAAGTTGATGATGTGTGTTGGTGATG (SEQ ID NO: 99) |
| B_CGF2.Ampseq-F | tctagcAAGTTGATGATGTGTGTTGGTGATG (SEQ ID NO: 100) |
| C_CGF2.Ampseq-F | gagtcaAAGTTGATGATGTGTGTTGGTGATG (SEQ ID NO: 101) |
| D_CGF2.Ampseq-F | gctagtAAGTTGATGATGTGTGTTGGTGATG (SEQ ID NO: 102) |
| E_CGF2.Ampseq-F | atgctaAAGTTGATGATGTGTGTTGGTGATG (SEQ ID NO: 103) |
| F_CGF2.Ampseq-F | ctgcgaAAGTTGATGATGTGTGTTGGTGATG (SEQ ID NO: 104) |
| G_CGF2.Ampseq-R | cgactgATAACATTGATTAACCCAACTTGAGC (SEQ ID NO: 105) |
| H_CGF2.Ampseq-R | tgatagATAACATTGATTAACCCAACTTGAGC (SEQ ID NO: 106) |
| I_CGF2.Ampseq-R | gtcacgATAACATTGATTAACCCAACTTGAGC (SEQ ID NO: 107) |
| J_CGF2.Ampseq-R | atgatgATAACATTGATTAACCCAACTTGAGC (SEQ ID NO: 108) |
| K_CGF2.Ampseq-R | cagtcaATAACATTGATTAACCCAACTTGAGC (SEQ ID NO: 109) |
| L_CGF2.Ampseq-R | acgtcaATAACATTGATTAACCCAACTTGAGC (SEQ ID NO: 110) |
| A_CGF3.Ampseq-F | gtactcCTTCAAGGGATGTTGATGGTCG (SEQ ID NO: 111) |
| B_CGF3.Ampseq-F | tctagcCTTCAAGGGATGTTGATGGTCG (SEQ ID NO: 112) |
| C_CGF3.Ampseq-F | gagtcaCTTCAAGGGATGTTGATGGTCG (SEQ ID NO: 113) |
| D_CGF3.Ampseq-F | gctagtCTTCAAGGGATGTTGATGGTCG (SEQ ID NO: 114) |
| E_CGF3.Ampseq-F | atgctaCTTCAAGGGATGTTGATGGTCG (SEQ ID NO: 115) |
| F_CGF3.Ampseq-F | ctgcgaCTTCAAGGGATGTTGATGGTCG (SEQ ID NO: 116) |

TABLE 10 -continued

| Primer | Sequence 5' to 3' |
|---|---|
| G_CGF3.Ampseq-RcgactgATCGATTTAGTGAGTTGAAGGGTGC | (SEQ ID NO: 117) |
| H_CGF3.Ampseq-RtgatagATCGATTTAGTGAGTTGAAGGGTGC | (SEQ ID NO: 118) |
| I_CGF3.Ampseq-RgtcacgATCGATTTAGTGAGTTGAAGGGTGC | (SEQ ID NO: 119) |
| J_CGF3.Ampseq-RatgatgATCGATTTAGTGAGTTGAAGGGTGC | (SEQ ID NO: 120) |
| K_CGF3.Ampseq-RcagtcaATCGATTTAGTGAGTTGAAGGGTGC | (SEQ ID NO: 121) |
| L_CGF3.Ampseq-RacgtcaATCGATTTAGTGAGTTGAAGGGTGC | (SEQ ID NO: 122) |

PCR amplifications were performed using Phusion polymerase (NEB), on genomic DNA isolated from regenerated lines targeted with LCT236 and LCT237 constructs. PCR amplification conditions were as follows: 95° C. for 5 min, then 35 cycles of 95° C. for 30 sec, 58° C. for 30 sec, 72° C. for 45 sec, and finally 10 min at 72° C. PCR products were loaded on agarose gel, purified using gel extraction kit and amplicons were pooled in equimolar ratio. These pooled amplicons were paired-end sequenced (2×250 bp) on 1Ilumina HiSeq2500 platform. After sequencing, reads were trimmed and filtered using Trimmomatic software to filter out the low-quality reads, paired sequences were merged using FLASH2 (Maga and Salzberg, Bioinformatics 27:2957-2963, 2011) with default parameters and demultiplexed using internal barcodes, and CRISPResso (Pinello et al., Nat. Biotechnol. 34:695, 2016) was used to ascertain the nature of mutations in the amplicons.

Four lines from targeting of the CGF2 gene (LCT236 construct) and nine lines from targeting of the CGF3 gene (LCT237 and LCT238 constructs) were recovered. Detailed biochemical and molecular analyses were performed on two lines in each case. The leaves obtained from the regenerated plants were examined for their terpenoid content. Table 11 shows the terpenoid values in the leaves of mutant lines generated by CRISPR/Cas9 mediated knockout of CGF2 (236-8 and 236-10) and CGF3 (237-3 and 237-4) genes in comparison to wild-type control (G: gossypol; HGQ: hemigossypolon; H: heliocides).

TABLE 11

| | Terpenoids (µg terpenoid/mg tissue) | | | | | |
|---|---|---|---|---|---|---|
| | HGQ | G | H1 | H2 | H3 | H4 |
| Wild-type | 0.33 | 0.18 | 0.07 | 0.28 | 0.11 | 0.04 |
| Line 236-8 | 0.01 | 0.02 | 0.00 | 0.00 | 0.00 | 0.00 |
| Line 236-10 | 0.00 | 0.01 | 0.00 | 0.00 | 0.00 | 0.00 |
| Line 237-3 | 0.00 | 0.00 | 0.00 | 0.00 | 0.00 | 0.00 |
| Line 237-4 | 0.00 | 0.00 | 0.00 | 0.00 | 0.00 | 0.00 |

The results show significant reduction in terpenoid levels in the leaf tissues of the CGF2 mutants (236-8 and 236-10). In line with the observations in VIGS experiments, the number of glands was substantially reduced in various parts of the mutant lines. The glands that were present were smaller and appeared abnormal in higher magnification images. Virtually no gossypol was detected in the leaves of CGF3 knockout plants (237-3 and 237-4; Table 11) and all parts of the plants examined were devoid of glands. These results confirm that CGF2 and CGF3 genes play important roles in the development of glands in the cotton plant. Furthermore, a completely glandless phenotype observed in the CGF3 knockout mutants validates the primacy of this gene as a key regulator of gland development.

Example 19

Overexpression of ACGF3 in Cotton Callus Tissue

While glands are present in most parts of the cotton plants, these have never been observed in callus cultures. To examine the impact of overexpressing CGF3 gene under the control of a constitutive promoter, such as the CaMV 35S promoter, an overexpression vector using the ACGF3 coding sequence driven by this promoter was assembled and used to transformed cotton seedling explants using the *Agrobacterium* method. ACGF3 coding sequence was amplified and placed downstream of CaMV 35S promoter by replacing the gusA gene in the binary vector pCAMBIA2301. This ACGF3 overexpression construct was then used to transform various cotton seedling explants as described herein. Individual transgenic events, in the form of small, kanamycin-resistant calli developing on the explants, were excised and further cultured as described herein. After four months, these were examined for terpenoid content as described herein.

Figure 7:
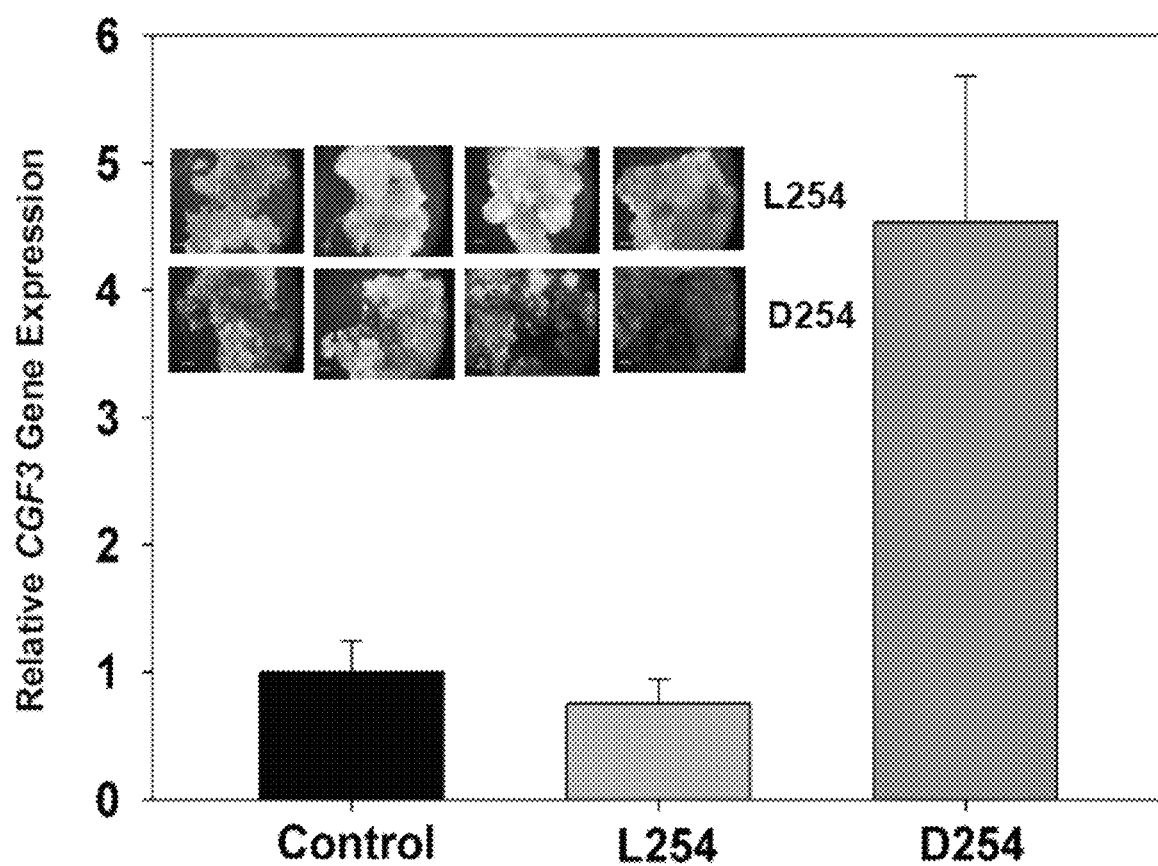
FIG. 7. qRT-PCR analysis of CGF3 transcripts in cotton callus cultures obtained following transformation with ACGF3 overexpression construct. L254: light-colored callus lines; D254 dark-colored callus lines; Control: non transgenic callus.
Figure 8:
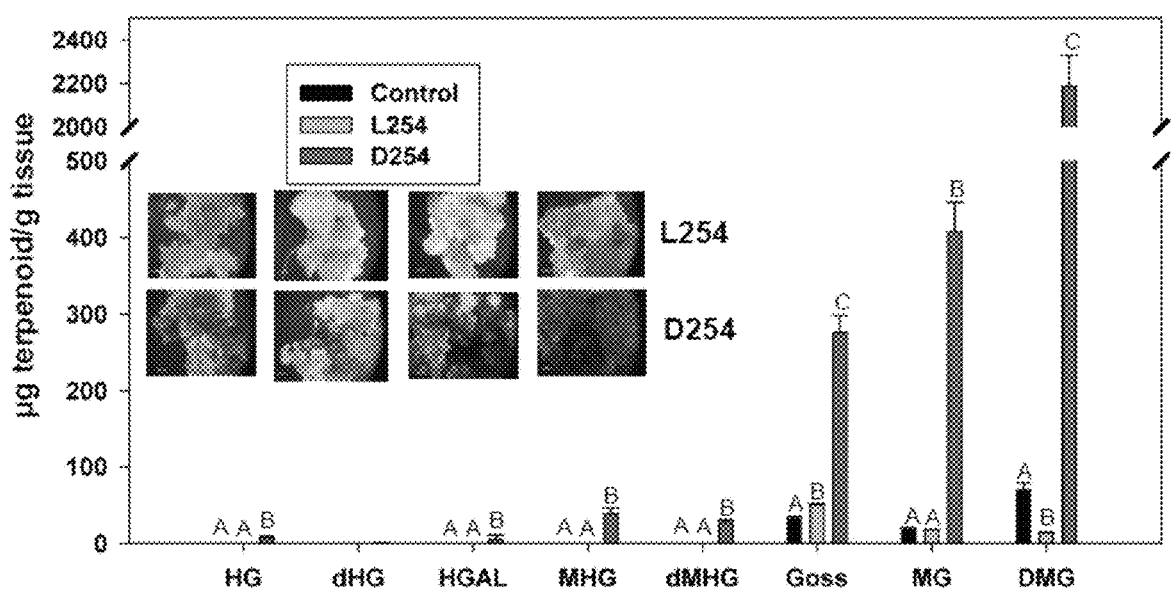
FIG. 8. Terpenoid levels in cotton callus cultures, obtained following transformation with ACGF3 overexpression construct. L254: light-colored callus lines; D254: dark-colored callus lines; Control: nontransgenic callus. HG: Hemigossypol; dHG: Desoxyhemigossypol; HGAL: Hemigossylic acid lactone; MHG: Methoxyhemigossypol; dMHG: Desoxymethoxyhemigossypol; Goss: Gossypol; MG: Methoxygossypol; DMG: Dimethoxygossypol. The values indicated by bars within a group are significantly different at p≤0.05 if labeled with different letters.

When observed after four months, a majority of these events had turned unusually dark brown, while a few events remained light pale-green color similar to what transgenic callus lines, transformed with any other gene, usually appear at this stage. The inventors reasoned that the dark-colored events were expressing the transgenic ACGF3 gene, while the lighter-colored ones were not. In order to examine this possibility, qRT-PCR was performed on these two types of culture lines. Results presented in FIG. 7 show that the dark-colored culture lines indeed showed higher-level transcription of CGF3 gene compared to the lighter-colored lines that showed activities similar to the non-transgenic control cultures. This molecular analysis was followed by an additional biochemical analysis in which we examined the two types of culture lines for their terpenoid content. Terpenoids that are usually found in glands, such as gossypol, were detected at significantly higher levels in the dark-colored cultures compared to the light-colored ones and the non-transgenic callus cultures (FIG. 8). In addition to gossypol, some other terpenoids were found either exclusively (hemigossypol, desoxyhemigossypol, hemigossylic acid lactone, methoxyhemigossypol, and desoxymethoxyhemigossypol) or at significantly higher levels (methoxygossypol and dimethoxygossypol) in the dark-colored culture lines.

The present results indicate that gland formation starts around 15 dpa. No glands were observed in the embryos at the 14-dpa stage in the greenhouse-grown, glanded cotton (STV GL) GVS4, however, at 16-dpa stage, the glands were clearly visible under a microscope in the embryos from this glanded line. No glands were observed in the glandless (STV gl) GVS5 at any stage of embryo development. Based on this information, transcriptome analyses were conducted on embryos at 14-, 16-, 32-dpa stage of development obtained from glanded, GVS4 and glandless, GVS5 near-isogenic cotton lines. RNA-seq analysis revealed that 33 genes were expressed at higher levels in the glanded embryos at 14 dpa compared to their counterparts from the glandless plants. Since no visible glands are present at this stage, the inventors reasoned that comparative transcriptomics at this time-point would reveal the identity of the genes that play an important role in initiating gland formation. The later stages of embryo development are likely to reveal the genes that are involved in gland maturation and biosynthesis of secondary metabolites, including gossypol.

RNA-seq proved to be a rather straightforward and useful technique in identifying a number of genes that were either solely expressed or more highly expressed in the embryos (14 dpa) of glanded cotton compared to those in the glandless cotton. VIGS was used against ten different genes that were predicted to encode proteins with regulatory functions to ascertain their involvement in gland formation. VIGS targeting of three different genes and their homeologs (designated CGF) significantly reduced the number of glands, and the terpenoids that are stored within, in the young emerging leaves of a cotton plantlet. Further, qRT-PCR results on each of these genes validated the RNA-seq analysis in terms of relative expression levels for the homeologs of the three CGF genes.

Sequencing of the respective homeologs of CGF1 and CGF2 did not show any differences between the glanded and glandless cotton. However, the ACGF3 gene in the glandless cotton had a 5.1 kb transposon insertion within its coding sequence, thus accounting for its silencing. The D subgenome homeolog of CGF3 gene in the glandless cotton showed two SNPs in the coding sequence and one SNP in the terminator between glanded and glandless cotton. However, the ~4.2 kb upstream regulatory sequence showed some major differences in the glandless cotton, including fifteen SNPs, two deletions (1 and 49 bp long), and two insertions (1 and 3 bp), compared to the glanded cotton. Comparative promoter activity analysis of this region between glanded and glandless cotton showed that the heavily mutated, DCGF3 gene promoter from the glandless cotton was substantially weakened.

No sequence differences between the glanded and glandless cotton were observed for the CGF1 and CGF2 genes and their respective homeologs. However, the fact that VIGS-mediated down regulation of these genes did have a negative impact on the gland numbers and terpenoid levels indicate that the respective encoded proteins do play an important role in gland formation. Particularly, the importance of CGF2 in gland development is supported by the fact that both VIGS and CRISPR/Cas9-mediated knockout of this gene not only had a negative effect on gland numbers, the glands that were visible appeared abnormal and the terpenoid content of the leaves was greatly reduced. Of the three CGF gene pairs, CGF3 genes seem to play the major role in gland development. Validation for this comes from the following results: 1) complete absence of CGF3 transcripts in the glandless embryos at all stages of development, 2) significant reduction in leaf glands and terpenoids by VIGS treatment, and 3) totally glandless phenotype and absence of terpenoids in the knockout lines created by CRISPR/Cas9-mediated mutations. The two CGF3 homeologs were localized on A12 and D12 chromosomes of G. hirsutum.

The basis for the silencing of the A subgenome CGF3 is likely due to the insertion of a 5.1 kb transposon, while the D subgenome CGF3 gene promoter of the glandless cotton has undergone extensive mutations, thus silencing the gene activity. The ACGF3 is localized on chromosome A12 while its homeolog the DCGF3 is present on chromosome D12. Here, we have provided substantial evidence that these two homeologs are the main genes controlling the development of glands in cotton plants.

While cotton is grown for its fiber, the plant produces ~1.6× more seed by weight. In addition to the oil, cottonseed also contains ~23% protein. Thus, global cottonseed production (~45 million metric tons, MMT) containing ~10 MMT of protein can potentially meet the basic protein requirements of ~550 million people. However, because of the presence of toxic gossypol in the seed glands, this abundant resource cannot be used for food or even as feed for monogastric animals. Whole cottonseed and cottonseed meal are used simply as feed for older cattle that are highly inefficient in converting feed protein into meat protein. Gossypol-free cottonseed meal can be a new source of protein for the more efficient aquaculture species and poultry, or can even be used as human food. The identification of the three CGF genes that play a direct or indirect role in gland formation provides the tools to suppress gland formation by silencing any one or more of these genes. Thus, strict tissue-specific silencing of the CGF gene(s) in the seed kernel should eliminate or significantly reduce its gossypol content. Tissue-specific silencing of a gene represents a powerful approach to examine the effects of silencing a gene in a particular tissue, and the trait created by these methods is stable and heritable.

Tissue specificity of such gene silencing is important because the terpenoid contents of the glands in the rest of the cotton plant provide protection against various pests and pathogens. The expression profile of the three CGF genes in the embryos of glanded and glandless cotton at various stages of development suggests that CGF2 and CGF3 can be safely targeted for silencing as these two genes are not transcribed in the embryos of glandless cotton and thus not necessary for normal embryo development, although in certain embodiments CGF1 can also be targeted. To further eliminate gossypol from the cottonseed, in addition to targeted one, two or all three of these CGF genes, it is also contemplated to also target the δ-cadinene synthase gene for silencing. Silencing of δ-cadinene synthase, which catalyzes a key step in the biosynthesis of gossypol, has been used successfully to significantly reduce gossypol in the cottonseed by 98% (Sunilkumar et al., *Proc. Natl. Acad. Sci. USA* 103:18054-18059, 2006). There are several gene-silencing technologies available such as RNAi, CRISPR interference (CRISPRi) and C2c2 (CRISPR-Cas13a)-mediated destruction of specific transcripts. Any such gene silencing technologies in conjunction with a seed-specific promoter are contemplated for use to eliminate the glands and thus gossypol from the cottonseed only.

While the CaMV35S promoter is typically considered to be too strong to drive a gene encoding a regulatory protein, the present results on the callus cultures overexpressing the ACGF3 gene point to a method of increasing the number of glands in the foliage and floral tissue by driving the expression of this gene (or CGF1 and/or CGF2, or any combinations thereof) under the control of its own promoter or another suitable promoter (i.e., a leaf- or green tissue-specific promoter). The expression of the CGF genes can also be increased using some form of CRISPR/Cas9 technology to enhance the activity of the respective native promoters. Thus, seed-specific silencing of CGF2/CGF3 (and in certain instances CGF1) genes and/or δ-cadinene synthase genes, while overexpressing the CGF3 gene (or CGF1 and/or CGF2, or any combinations thereof) in other organs, by modification of native promoters or transgenic overexpression, can provide a cotton plant that produces gossypol-free seeds, while having greater number of glands (and therefore higher levels of gossypol and related terpenoids) in the rest of the plant for more robust defense against pests and pathogens. There is an increasing need for such a 'natural' defense mechanism against pests because more and more insect species are developing resistance to various forms of Bt-cotton. The cost of refining oil from such gossypol-free cottonseed will be lower, and the meal can be used as a source of protein for the more efficient monogastric animals (poultry, swine and aquaculture species) and even as food, thus enhancing nutrition security in the cotton-producing parts of the world.

Having illustrated and described the principles of the present disclosure, it should be apparent to persons skilled in the art that the present disclosure can be modified in arrangement and detail without departing from such principles. We claim all modifications that are within the spirit and scope of the appended claims.

What is claimed is:

1. A cotton plant exhibiting artificially down-regulated CGF2 gene expression compared to a wild-type control plant exhibiting normal CGF2 expression, wherein the plant exhibits reduced gossypol content in seed compared to a wild-type control plant exhibiting normal CGF2 expression, wherein the CGF2 gene comprises at least 95% identity to SEQ ID NO:3 or SEQ ID NO:4, and wherein:
   a) the plant comprises a mutated genomic CGF2 gene; or
   b) the plant comprises an RNAi, CRISPR, CRISPRi or C2c2 construct directed against the CGF2 gene or a transcript thereof.

2. The plant of claim 1, wherein the RNAi, CRISPR, CRISPRi, or C2c2 construct expresses a RNA molecule that comprises all or a portion of SEQ ID NO:3 or SEQ ID NO:4, or the complement thereof, wherein said RNA molecule is at least 21 nucleotides in length.

3. The plant of claim 1, wherein the RNAi, CRISPR, CRISPRi, or C2c2 construct is operably linked to a seed-specific promoter.

4. The plant of claim 1, wherein said plant further exhibits artificially down-regulated CGF1, CGF3 or δ-cadinene synthase gene expression compared to a wild-type control plant exhibiting normal CGF1, CGF3 or δ-cadinene expression, wherein the CGF1 gene comprises at least 95% identity to SEQ ID NO:1 or SEQ ID NO:2, and wherein the CGF3 gene comprises at least 95% identity to SEQ ID NO:5, SEQ ID NO:6, SEQ ID NO:7 or SEQ ID NO:8.

5. The plant of claim 1, wherein said plant further exhibits increased CGF1 or CGF3 gene expression in leaves of said plant compared to a wild-type control exhibiting normal CGF1 or CGF3 expression, wherein the CGF1 gene comprises at least 95% identity to SEQ ID NO:1 or SEQ ID NO:2, and wherein the CGF3 gene comprises at least 95% identity to SEQ ID NO:5, SEQ ID NO:6, SEQ ID NO:7 or SEQ ID NO:8.

6. The plant of claim 5, wherein said CGF1, CGF2 or CGF3 gene expression is controlled by a leaf-specific or green tissue-specific promoter.

7. The plant of claim 1, wherein the plant is a *Gossypium hirsutum* cotton plant.

8. A plant part of the plant of claim 1, wherein the plant part comprises a cell of said plant.

9. A seed that produces the plant of claim 1.

10. A method of reducing gossypol content in seed in a cotton plant comprising artificially down-regulating expression of a CGF2 gene in seed in the plant compared to plant exhibiting normal CGF2 expression, wherein the gossypol content in seed of the plant is reduced when compared to a plant exhibiting normal CGF2 expression wherein the CGF2 gene comprises at least 95% identity to SEQ ID NO:3 or SEQ ID NO:4, and wherein:
   a) the plant comprises a mutated genomic CGF2 gene; or
   b) the plant comprises an RNAi, CRISPR, CRISPRi or C2c2 construct directed against the CGF2 gene or a transcript thereof.

11. The method of claim 10, wherein down-regulating the expression of the CGF2 gene comprises expressing in the plant a RNA molecule complementary to all or a portion of SEQ ID NO:3 or SEQ ID NO:4, wherein said RNA molecule is at least 21 nucleotides in length.

12. The method of claim 11, wherein expression of the RNA molecule is regulated by a seed-specific promoter.

13. The method of claim 10, wherein expression of CGF1, CGF3 or δ-cadinene synthase gene expression is also down-regulated.

14. The method of claim 10, wherein said plant further exhibits increased CGF1 or CGF3 gene expression in leaves of said plant.

15. The method of claim 14, wherein said CGF1, CGF2 or CGF3 gene expression is controlled by a leaf-specific or green tissue-specific promoter.

16. The method of claim 10, wherein the plant is a *Gossypium hirsutum* cotton plant.

17. A method of producing food, feed, or oil comprising:
   (a) obtaining a plant of claim 1;
   (b) cultivating said plant to obtain a plant product; and
   (c) preparing food, feed, or oil from said plant or plant product.

18. The method of claim 17, wherein the plant or plant product comprises reduced gossypol relative to a plant or plant product lacking said down-regulated activity of a CGF2 gene product.

* * * * *